US008404236B2

(12) United States Patent
Wu et al.

(10) Patent No.: US 8,404,236 B2
(45) Date of Patent: *Mar. 26, 2013

(54) METHOD OF IDENTIFYING MEMBRANE IG SPECIFIC ANTIBODIES AND USE THEREOF FOR TARGETING IMMUNOGLOBULIN-PRODUCING PRECURSOR CELLS

(75) Inventors: Herren Wu, Boyds, MD (US); Peter Kiener, Potomac, MD (US); Partha S. Chowdhury, Gaithersburg, MD (US); James F. Young, Potomac, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,170

(22) Filed: Feb. 13, 2012

(65) Prior Publication Data

US 2012/0141463 A1    Jun. 7, 2012

Related U.S. Application Data

(63) Continuation of application No. 12/067,396, filed as application No. PCT/US2006/037724 on Sep. 28, 2006, now Pat. No. 8,137,670.

(60) Provisional application No. 60/721,525, filed on Sep. 29, 2005.

(51) Int. Cl.
*A61K 39/00* (2006.01)

(52) U.S. Cl. ............... 424/139.1; 424/133.1; 424/136.1; 424/177.1; 424/805; 424/810; 530/387.3; 530/387.9; 530/388.25; 530/862; 530/868

(58) Field of Classification Search .................. None
See application file for complete search history.

(56) References Cited

U.S. PATENT DOCUMENTS

| | | | |
|---|---|---|---|
| 5,079,344 A | 1/1992 | Chang et al. | |
| 5,089,603 A | 2/1992 | Chang et al. | |
| 5,091,313 A | 2/1992 | Chang | |
| 5,231,026 A | 7/1993 | Chang | |
| 5,252,467 A | 10/1993 | Chang | |
| 5,254,671 A | 10/1993 | Chang | |
| 5,260,416 A | 11/1993 | Chang | |
| 5,274,075 A | 12/1993 | Chang | |
| 5,281,699 A | 1/1994 | Chang | |
| 5,292,867 A | 3/1994 | Chang | |
| 5,298,420 A | 3/1994 | Chang | |
| 5,310,875 A | 5/1994 | Chang | |
| 5,342,924 A | 8/1994 | Chang | |
| 5,362,643 A | 11/1994 | Chang | |
| 5,420,251 A | 5/1995 | Chang et al. | |
| 5,422,258 A | 6/1995 | Chang | |
| 5,428,133 A | 6/1995 | Chang | |
| 5,449,760 A | 9/1995 | Chang | |
| 5,484,907 A | 1/1996 | Chang et al. | |
| 5,514,776 A | 5/1996 | Chang | |
| 5,543,144 A | 8/1996 | Chang | |
| 5,614,611 A | 3/1997 | Chang | |
| 5,690,934 A | 11/1997 | Chang et al. | |
| 5,759,808 A | 6/1998 | Casterman et al. | |
| 5,866,129 A | 2/1999 | Chang et al. | |
| 5,958,708 A * | 9/1999 | Hardman et al. | 435/7.21 |
| 5,994,511 A * | 11/1999 | Lowman et al. | 530/387.3 |
| 6,037,453 A * | 3/2000 | Jardieu et al. | 530/387.3 |
| 6,685,939 B2 * | 2/2004 | Jardieu et al. | 424/133.1 |
| 6,699,472 B2 * | 3/2004 | Jardieu et al. | 424/133.1 |
| 6,986,889 B2 | 1/2006 | Laffer et al. | |
| 7,371,849 B2 | 5/2008 | Honda et al. | |
| 7,531,169 B2 * | 5/2009 | Singh et al. | 424/130.1 |
| 2002/0172673 A1 | 11/2002 | Klysner et al. | |
| 2003/0175969 A1 * | 9/2003 | Beliard et al. | 435/455 |
| 2004/0132101 A1 * | 7/2004 | Lazar et al. | 435/7.1 |
| 2005/0152892 A1 | 7/2005 | Friede et al. | |

FOREIGN PATENT DOCUMENTS

| | | |
|---|---|---|
| EP | 1972640 A1 | 9/2008 |
| WO | WO 89/06138 | 7/1989 |
| WO | WO 90/15614 | 12/1990 |
| WO | WO 91/04055 | 4/1991 |
| WO | WO 91/11456 | 8/1991 |
| WO | WO 92/07574 | 5/1992 |
| WO | WO 96/12740 | 5/1996 |
| WO | WO 98/53843 | 12/1998 |
| WO | WO 00/50461 | 8/2000 |
| WO | WO 02/20038 A2 | 3/2002 |
| WO | WO 04/000217 A2 | 12/2003 |
| WO | WO 2004/041867 A2 | 5/2004 |
| WO | WO 2008/116149 A2 | 9/2008 |
| WO | WO 2008/123999 A2 | 10/2008 |

OTHER PUBLICATIONS

Chen, Huan Yuan et al., 2001, "Monoclonal Antibodies against the CεmX Domain of Human Membrane-Bound IgE and Their Potential Use for Targeting IgE-Expressing B Cells", International Archives of Allergy and Immunology, 128-315-324.
Diaz et al., 2002, "Structural analysis, selection, and ontogeny of the shark new antigen receptor (IgNAR): identification of a new locus preferentially expressed in early development", Immunogenics 54: 501-12.
International Search Report for PCT/US06/37724 mailed Jul. 1, 2008.
Janeway et al., Immunobiology, 3rd edition, 1997, Garland Press Inc. Chapter 3, pp. 1-11.
Portolano et al., 1993, "Lack of Promiscuity in Autoantigen-Specific H and L Chain Combinations as Revealed by Human H and L Chain Roulette" J. Immunol. 150: 880-887.
Supplementary European Search Report for EP 06 81 5598 dated Sep. 16, 2010.
William E. Paul, M.D., editor, Fundemental Immunology, 3rd edition, 1993, Raven Press. Chapter 8, p. 242.

* cited by examiner

*Primary Examiner* — Michael Szperka
(74) *Attorney, Agent, or Firm* — MedImmune, LLC

(57) ABSTRACT

The present invention relates to the discovery of antibodies that bind to novel epitopes present on membrane-anchored immunoglobulins and which bind to these novel epitopes on the surface of B cells and plasma cells. In addition, the antibodies of the present invention can mediate ADCC and can be useful to deplete those B cells and plasma cells expressing the novel epitopes of the invention. The antibodies of the present invention can be useful for the treatment of B cell-mediated diseases and diseases caused by monoclonal expansion of B cells. Accordingly the present invention also provides compositions and methods for the prevention, management, treatment or amelioration of B cell-mediated diseases and diseases caused by monoclonal expansion of B cells.

17 Claims, 27 Drawing Sheets

IgD: NH2-YLAMTPLIPQSKDENSDDYTTFDDVGS-COOH (7%) (SEQ ID NO: 47)

IgM: NH2-EGEVSADEEGFEN-COOH (31%) (SEQ ID NO: 2)

IgG: NH2-ELQLEESCAEAQDGELDG-COOH (27%) (SEQ ID NO: 48)

IgA: NH2-DWQMPPPYVVLDLPQETLEEETPGAN-COOH (7%) (SEQ ID NO: 49)

IgE: NH2-ELDVCVEEAEGEAPW-COOH (100%) (SEQ ID NO: 1)

Fig 1A

```
IgE:  NH2-ELDVCVEEAEGEAPW-COOH   (SEQ ID NO: 1)
          |:: |::: |    |
IgM:  NH2-EGEVSADEEGFEN-COOH     (SEQ ID NO: 2)
```

Figure 2:
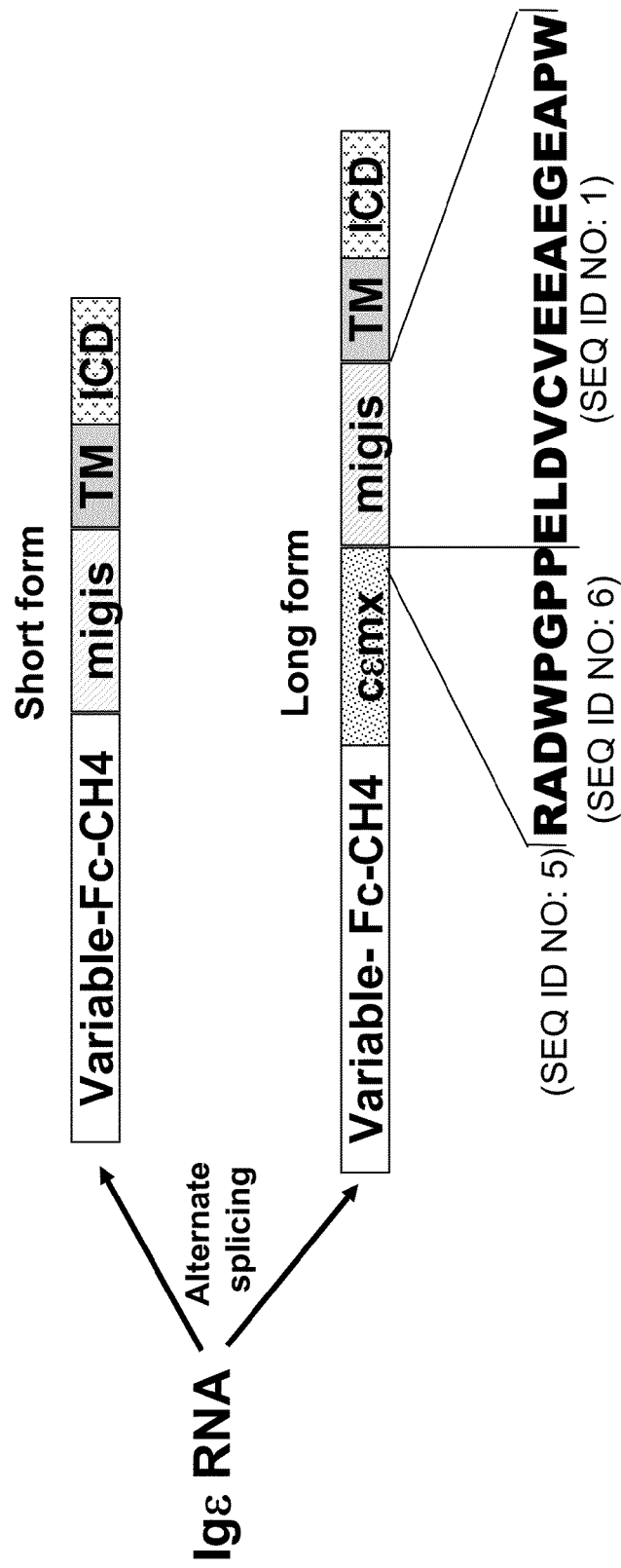

Phosphoinositide binding protein:
(recently identified as the receptor for anthrax PA)

```
NH2- CVEEAEGEAPW -COOH   (portion of SEQ ID NO: 1)
     —— AF —— E ——
```

KIAA1227:
(predicted sequence resembles cell signaling, communication and motility associated proteins)

```
NH2- VEEAEGEAP –COOH   (portion of SEQ ID NO: 1)
     ——— E ——
```

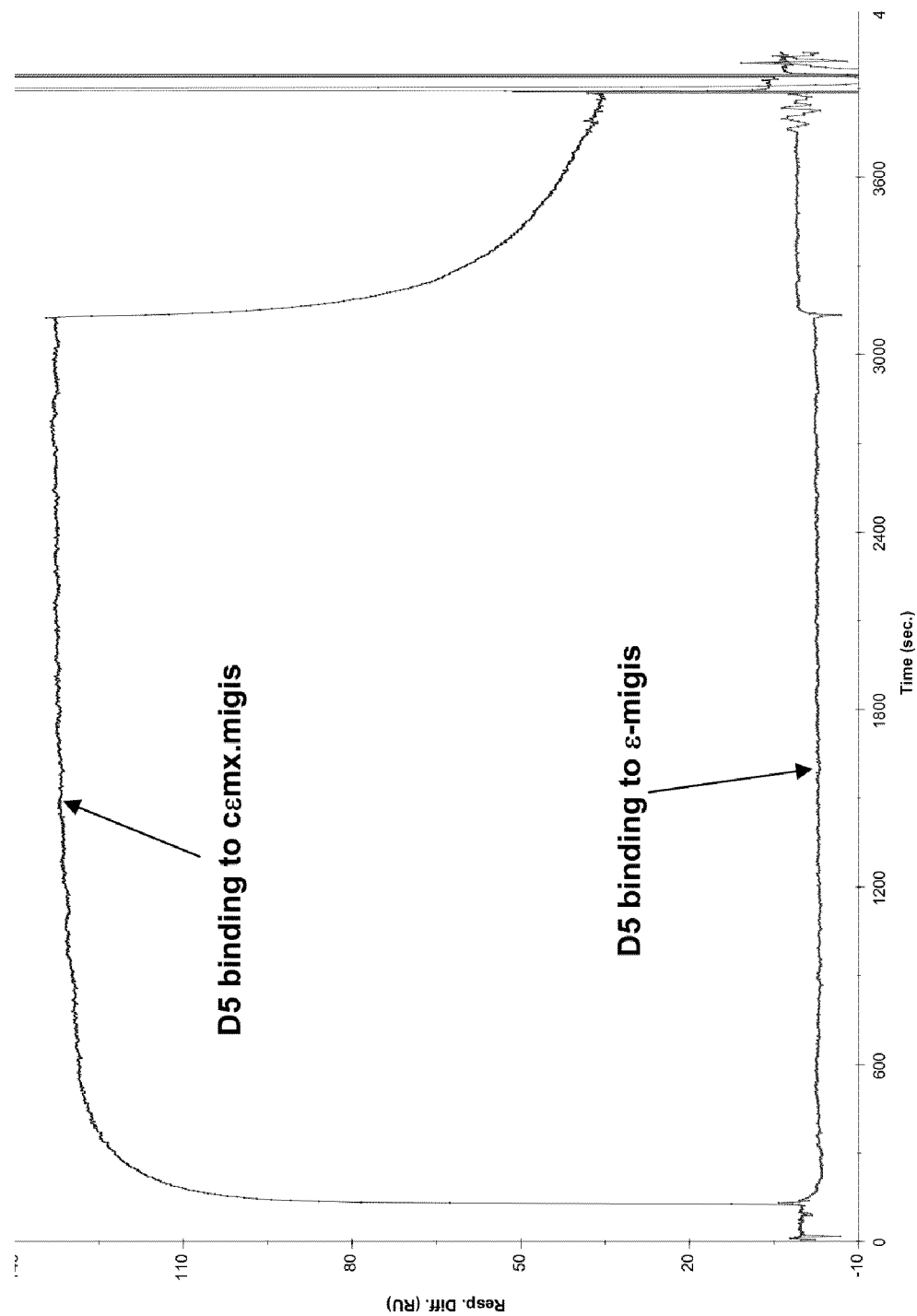

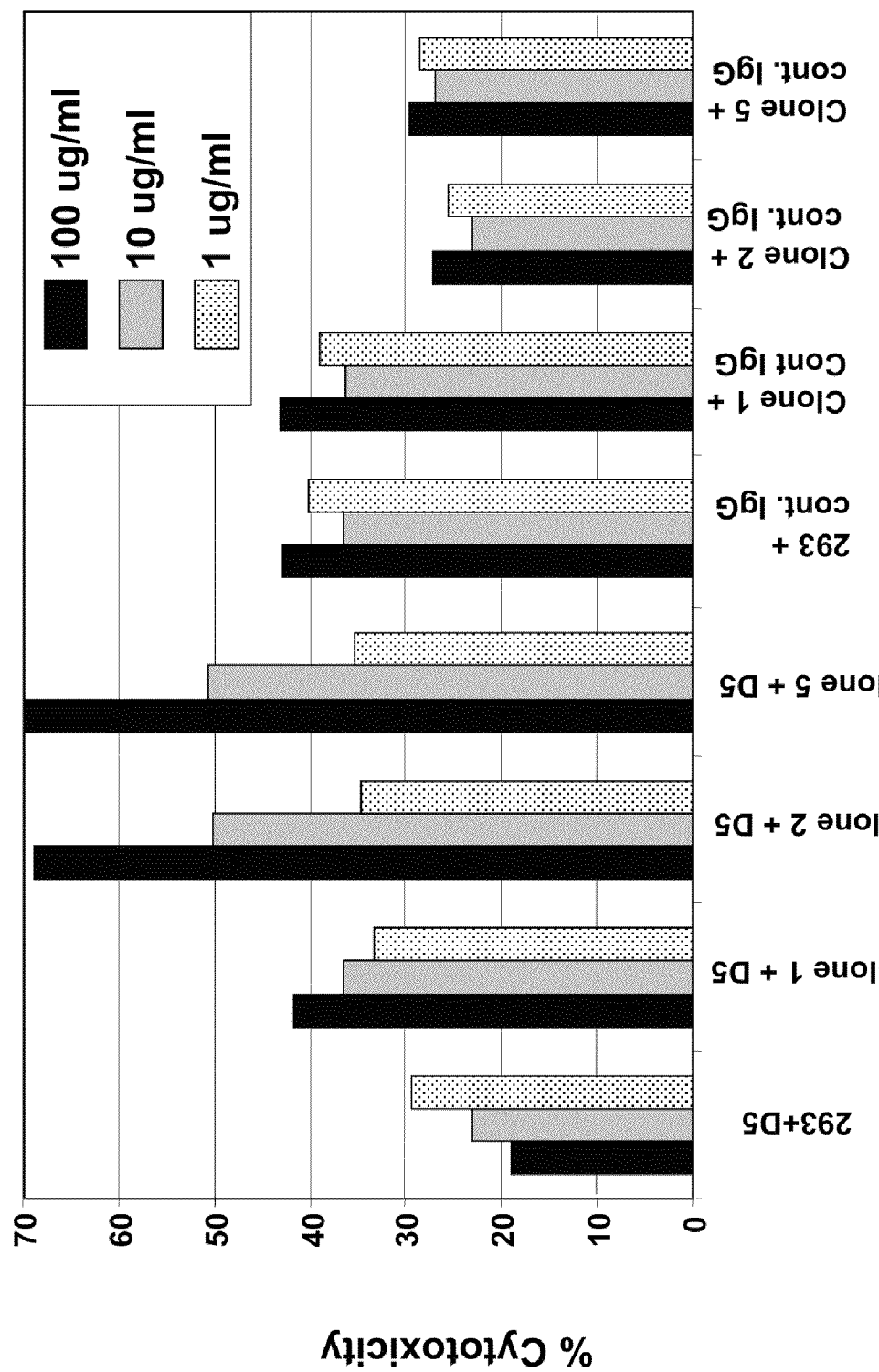

```
GAAGTTCAATTGTTAGAGTCTGGTGGCGGTCTTGTTCAGCCTGGTGGTTCTTTGCGCTGCTTCCGGATT
Glu Val Gln Leu Leu Glu Ser Gly Gly Gly Leu Val Gln Pro Gly Gly Ser Leu Arg Leu Ser Cys Ala Ala Ser Gly Phe
                                                                                                              80
CACTTTCTCTAAGTACCATATGGTTTGGGTTCGCCAAGCTCCTGGTAAAGGTTTGGAGTGGGTTTCTTCTTATCGGTCCTT
Thr Phe Ser Lys Tyr His Met Val Trp Val Arg Gln Ala Pro Gly Lys Gly Leu Glu Trp Val Ser Ser Ile Gly Pro
                    ——CDR1——                                                              ——CDR2
                                                                                                              160
CTGGTGGCAATACTTATTATGCTGACTCCGTTAAAGGTCGCTTCACTATCTCTAGAGACAACTCTAAGAATACTCTCTAC
Ser Gly Gly Asn Thr Tyr Tyr Ala Asp Ser Val Lys Gly Arg Phe Thr Ile Ser Arg Asp Asn Ser Lys Asn Thr Leu Tyr
       ————————————CDR2————————————
                                                                                                              240
TTGCAGATGAACAGCTTAAGGGCTGAGGACACAGCCGTATACTACTGTGCGAGAGCCCTCGGAGCTACCTTTGACTACTG
Leu Gln Met Asn Ser Leu Arg Ala Glu Asp Thr Ala Val Tyr Tyr Cys Ala Arg Ala Leu Gly Ala Thr Phe Asp Tyr Trp
                                                                    ————————CDR3————————
                                                                                                              320
GGGCCAGGGAACCCTGGTCACCGTCTCAAGC      (SEQ ID NO: 8)
Gly Gln Gly Thr Leu Val Thr Val Ser Ser   (SEQ ID NO: 10)
                                                                                                              351
```

Fig 12A

```
GAAGTTCAATTGTTAGAGTCTGGTGGCGGTCTTGTTCAGCCTGGTGGTTCTTTGCGCTGCTTCCGGATT     80
Glu Val Gln Leu Leu Glu Ser Gly Gly Gly Leu Val Gln Pro Gly Gly Ser Leu Arg Leu Ser Cys Ala Ala Ser Gly Phe

CACTTTCTCTTTTTACTCTATGCTTTGGGTTCGCCAAGCTCCTGGAGTGGGTTTCTTTATATCGGTCCTT    160
Thr Phe Ser Phe Tyr Ser Met Leu Trp Val Arg Gln Ala Pro Gly Lys Gly Leu Glu Trp Val Ser Tyr Ile Gly Pro
         CDR1                                                                    CDR2

CTGGTGGCAAGACTTATTATGCTGACTCCGTTAAAGGTCGCTTCACTATCTCTAGAGACAACTCTAAGAATACTCTCTAC   240
Ser Gly Gly Lys Thr Tyr Tyr Ala Asp Ser Val Lys Gly Arg Phe Thr Ile Ser Arg Asp Asn Ser Lys Asn Thr Leu Tyr
              CDR2

TTGCAGATGAACAGCTTAAGGGCTGAGGACACCGCCATGTATTACTGTGCGAGACGCTATTGTAGTGGTGGTAGCTGCTA   320
Leu Gln Met Asn Ser Leu Arg Ala Glu Asp Thr Ala Met Tyr Tyr Cys Ala Arg Arg Tyr Cys Ser Gly Gly Ser Cys Tyr
                                                                                        CDR3

CTTTTGACTACTGGGGCCAGGGCACCCTGGTCACCGTCTCAAGC     (SEQ ID NO: 51)              363
Phe Asp Tyr Trp Gly Gln Gly Thr Leu Val Thr Val Ser Ser     (SEQ ID NO: 53)
     CDR3
```

Fig 13A

```
GCACAAGACATCCAGATGACCCAGTCTCCTTCCACCCTGTCTGCATCTATAGGAGACAGAGTCACCATCACTTGCCGGGC
 Ala  Gln  Asp  Ile  Gln  Met  Thr  Gln  Ser  Pro  Ser  Thr  Leu  Ser  Ala  Ser  Ile  Gly  Asp  Arg  Val  Thr  Ile  Thr  Cys  Arg  Ala
     Extra                                                                                                                            80

CAGTCAGAGTATTAATAGTTGGTTGGCCTGGTATCAGCAGAAACCAGGGAAAGGCCCTAAGCTCCTGATCTATAAGGCGT
 Ser  Gln  Ser  Ile  Asn  Ser  Trp  Leu  Ala  Trp  Tyr  Gln  Gln  Lys  Pro  Gly  Lys  Gly  Pro  Asp  Leu  Leu  Ile  Tyr  Lys  Ala
                    ─── CDR1 ───                                                                                 ── CDR2 ──        160

CTAGTTTACAAAGTGGGGTCCCATCAAGGTTCAGCGGCAGTGGATCTGGGACAGAATTCACTCTCACCATCAGCAGCCTG
 Ser  Ser  Leu  Gln  Ser  Gly  Val  Pro  Ser  Arg  Phe  Ser  Gly  Ser  Gly  Ser  Gly  Thr  Glu  Phe  Thr  Leu  Thr  Ile  Ser  Ser  Leu
     ── CDR2 ──                                                                                                                     240

CAGCCTGATGATTTTGCAACTTATTACTGCCAACAGTATAGTAGTTCCCCCCTCACTTTCGGCGGAGGGACCAAGGTGGA
 Gln  Pro  Asp  Asp  Phe  Ala  Thr  Tyr  Tyr  Cys  Gln  Gln  Tyr  Ser  Ser  Ser  Pro  Leu  Thr  Phe  Gly  Gly  Gly  Thr  Lys  Val  Glu
                                                        ───────────── CDR3 ─────────────                                            320

GATCAAACGA    (SEQ ID NO: 50)
 Ile  Lys  Arg    (SEQ ID NO: 52)                                                                                                   330
```

Fig 13B

GAAGTTCAATTGTTAGAGTCTCTGGTGGCGGTCTTGTTCAGCCTGGTGGTTCTTTACGTCTCTTTGCGCTGCTTCCGGATT
Glu Val Gln Leu Leu Ser Gly Gly Gly Leu Val Gln Pro Gly Gly Ser Leu Arg Leu Ser Cys Ala Ala Ser Gly Phe

CACTTTCTCTAAGTACGGTATGACTTGGGTTCGCCAAGCTCCTGGTAAAGGTTTGGAGTGGGTTTCTTCTATCTATTCTT
Thr Phe Ser Lys Tyr Gly Met Thr Trp Val Arg Gln Ala Pro Gly Lys Gly Leu Glu Trp Val Ser Ser Ile Tyr Ser
                                         CDR1                                                    CDR2

CTGGTGGCCCTACTGAGTATGCTGACTCCGTTAAAGGTCGCTTCACTATCTCTAGAGACAACTCTAAGAATACTCTCTAC
Ser Gly Gly Pro Thr Glu Tyr Ala Asp Ser Val Lys Gly Arg Phe Thr Ile Ser Arg Asp Asn Ser Lys Asn Thr Leu Tyr
                     CDR2

TTGCAGATGAACAGCTTAAGGGCTGAGGACACGGCCGTGTATTACTGTGCGAGAGGTGGGGGTATGGGACGTCTGGGGCCA
Leu Gln Met Asn Ser Leu Arg Ala Glu Asp Thr Ala Val Tyr Tyr Cys Ala Arg Gly Gly Gly Met Gly Asp Val Trp Gly Gln
                                                                                         CDR3

AGGCACCCTGGTCACCGTCTCAAGC (SEQ ID NO: 61)
Gly Thr Leu Val Thr Val Ser Ser  (SEQ ID NO: 63)

Fig 14A

```
GAAGTTCAATTGTTAGAGTCTGGTGGCGGTCTCTTGTTCAGCCTGGTGGTTCTTTGCGCTGCTTCCGGATT       80
Glu Val Gln Leu Val Glu Ser Gly Gly Gly Leu Val Gln Pro Gly Gly Ser Leu Arg Leu Ser Cys Ala Ala Ser Gly Phe

CACTTTCTCTAATTACGGTATGTTTTGGGTTCGCCAAGCTCCTGGTAAAGGTTTGGAGTGGGTTTCTTCTATCTGGCCTT      160
Thr Phe Ser Asn Tyr Gly Met Phe Trp Val Arg Gln Ala Pro Gly Lys Gly Leu Glu Trp Val Ser Ser Ile Trp Pro
                    ———CDR1———                                                      ———CDR2

CTGGTGGCAATACTATGTATGCTGACTCCGTTAAAGGTCGCTTCACTATCTCTAGAGACAACTCTAAGAATACTCTCTAC      240
Ser Gly Gly Asn Thr Met Tyr Ala Asp Ser Val Lys Gly Arg Phe Thr Ile Ser Arg Asp Asn Ser Lys Asn Thr Leu Tyr
                ———CDR2———

TTGCAGATGAACAGCCTTAAGGGCTGAGGACACGGCCGTGTATTACTGTGCGAGAGCTTCTTACTACGGTATGGACGTCTG      320
Leu Gln Met Asn Ser Leu Arg Ala Glu Asp Thr Ala Val Tyr Tyr Cys Ala Arg Ala Ser Tyr Tyr Gly Met Asp Val Trp
                                                                    ———CDR3———

GGGCCAAGGGACCACGGTCACCGTCTCAAGC   (SEQ ID NO: 71)                                     351
Gly Gln Gly Thr Thr Val Thr Val Ser Ser   (SEQ ID NO: 73)
```

Fig 15A

```
GCACAAGACATCCAGATGACCCAGTCTCCATCCTCCCTGTCTGCATCTATAGGCGACAGAGTCACCATCACTTGCCGCGG                    80
 Ala Gln Asp Ile Gln Met Thr Gln Ser Pro Ser Ser Leu Ser Ala Ser Ile Gly Asp Arg Val Thr Ile Thr Cys Arg Gly
 Extra AAGTCAGAATATTTGGTAGATATTTAAATTGGTATCAACAGAAACCAGGGAAAGCCCCTGATCTCCTCGTCTATGCTGCCT                  160
 Ser Gln Asn Ile Gly Arg Tyr Leu Asn Trp Tyr Gln His Lys Pro Gly Lys Ala Pro Asp Leu Leu Val Tyr Ala Ala
                       CDR1                                                                      CDR2

CCAGTTTGCGAAGTGGGGTCCCATCAAGATTCAGTGGCAGTGGATCTGGGACAGATTTCACTCTCACCATCAGCAGTCTT                    240
 Ser Ser Leu Arg Ser Gly Val Pro Ser Arg Phe Ser Gly Ser Gly Ser Gly Arg Asp Phe Thr Leu Thr Ile Ser Ser Leu
     CDR2

CAACCTGGAGATTTTGCAACTTACTACTGTCAGCAGAGTTACAGTGCCCCGTTCACTTTCGGCCCGGGACCAAGGTGGA                     320
 Gln Pro Gly Asp Phe Ala Thr Tyr Tyr Cys Gln Gln Ser Tyr Ser Ala Pro Phe Thr Phe Gly Ala Gly Thr Lys Val Asp
                                                                    CDR3

TGTCAAAACGA   (SEQ ID NO: 70)                                                                        330
 Val Lys Arg   (SEQ ID NO: 72)
```

Fig 15B

```
GAAGTTCAATTGTTAGAGTCTGGTGGCGGTCTTGTTCAGCCTGGTGGTTCTTTACGTCTTTCTTGCGCTGCTTCCGGATT
         +---------+---------+---------+---------+---------+---------+---------+---------+   80
Glu Val Gln Leu Leu Glu Ser Gly Gly Gly Leu Val Gln Pro Gly Gly Ser Leu Arg Leu Ser Cys Ala Ala Ser Gly Phe

CACTTTCTCTACTTACGCTATGCGTTGGGTTCGCCAAGCTCCTGGTAAAGGTTTGGAGTGGGTTTCTGGTATCGGTCCTT
         +---------+---------+---------+---------+---------+---------+---------+---------+   160
Thr Phe Ser Thr Tyr Ala Met Arg Trp Val Arg Gln Ala Pro Gly Lys Gly Leu Glu Trp Val Ser Gly Ile Gly Pro
                     ■————— CDR1 —————                                                      ■————— CDR2

CTGGTGGCAAGACTTCTTATGCTGACTCCGTTAAAGGTCGCTTCACTATCTCTAGAGACAACTCTAAGAATACTCTCTAC
         +---------+---------+---------+---------+---------+---------+---------+---------+   240
Ser Gly Gly Lys Thr Ser Tyr Ala Asp Ser Val Lys Gly Arg Phe Thr Ile Ser Arg Asp Asn Ser Lys Asn Thr Leu Tyr
—————————————————— CDR2

TTGCAGATGAACAGCTTAAGGGCTGAGGACACGGCCGTGTATTACTGTGCGAGAGCTCTGGTATAGTGGGAGCTTATTC
         +---------+---------+---------+---------+---------+---------+---------+---------+   320
Leu Gln Met Asn Ser Leu Arg Ala Glu Asp Thr Ala Val Tyr Tyr Cys Ala Arg Ala Leu Val Gly Ile Val Gly Ala Tyr Ser
                                                                          ■————— CDR3

GTACGGTATGGACGTCTGGGGCCAAGGGACCACGGTCTCAAGCGCCTCC (SEQ ID NO: 80)
         +---------+---------+---------+---------+      375                 (SEQ ID NO: 81)
Tyr Gly Met Asp Val Trp Gly Gln Gly Thr Thr Val Thr Val Ser Ser Ala Ser
————— CDR3
```

Fig 16

METHOD OF IDENTIFYING MEMBRANE IG SPECIFIC ANTIBODIES AND USE THEREOF FOR TARGETING IMMUNOGLOBULIN-PRODUCING PRECURSOR CELLS

CROSS REFERENCE TO RELATED APPLICATIONS

This application is a continuation of U.S. application Ser. No. 12/067,396 filed on Oct. 7, 2008, now U.S. Pat. No. 8,137,670, said application Ser. No. 12/067,396 is a national phase filing of Application No. PCT/US2006/037724, filed with the Patent Corporation Treaty on Sep. 28, 2006, and claims the benefit under 35 U.S.C. §119(e) of U.S. Provisional Application No. 60/721,525, filed Sep. 29, 2005. Each of the above listed applications is hereby incorporated by reference herein in its entirety for all purposes.

REFERENCE TO THE SEQUENCE LISTING

This application incorporates by reference a Sequence Listing submitted with this application as text file entitled "IGE-130US2_ST25" created on Feb. 6, 2012 and having a size of 28 kilobytes.

1. FIELD OF THE INVENTION

The present invention relates to agents that bind membrane-anchored IgE molecules. In one embodiment, the present invention relates to agents that specifically bind to cells with membrane-anchored IgE and mediate antibody-dependent cellular cytotoxicity.

2. BACKGROUND OF THE INVENTION

IgE mediates, among other things, immediate-type hypersensitivity reactions. For an allergic reaction to occur, an individual must have had prior exposure to an allergen. Following the initial antigen exposure, the immune system produces IgE specific for the inciting antigen. The antigen-specific IgE then binds to mast cell membranes via IgE receptors. When re-exposed to the antigen, the antigen-specific IgE antibody binds to the antigen and activates the mast cells. Such mast cell activation causes a release of vasoactive and neuronal stimulatory mediators such as histamines, leukotrienes, prostaglandins, bradykinin, and platelet-activating factor which work in conjunction with cells such as eosinophils, basophils, neutrophils, and CD4 T-lymphocytes. Allergen induced IgE secretion can result in a variety of complications, including death, as may be the case in serious cases of asthma and anaphylaxis. These allergic disorders are prevalent. For example, allergic rhinitis (hay fever) affects 22% or more of the population of the USA, whereas allergic asthma is thought to affect at least 20 million residents of the USA. The economic impact of allergic diseases in the United States, including health care costs and lost productivity, has been estimated to amount to $6.4 billion in the early nineties alone.

IgE is secreted by IgE-producing plasma cells, which differentiate from B cells expressing membrane-bound IgE (mIgE) on their surface. IgE not only has the shortest biologic half-life of all classes of immunoglobulins (Igs), but also is present in serum at the lowest levels. However, IgE concentrations in allergic reactions (atopic) in individuals can be 100- to 1000-fold higher than in normal individuals. IgE is directly involved in mediating many allergic reactions as a result of its ability to bind to and, upon contact with multivalent allergen, activate various effector cells, such as mast cells and basophils, through interactions with FcεRI receptors.

Since IgE plays a central role in mediating most allergic reactions, devising treatments to control IgE levels in the body and regulating IgE synthesis has been of great interest. Several strategies have been proposed to treat IgE-mediated allergic diseases by downregulating IgE levels. One strategy involves neutralizing the IgE molecules by binding the ε-chain of IgE in or near the Fc-receptor binding site. For example, Omalizumab (Xolair) is a recombinant humanized monoclonal anti-IgE antibody that binds to IgE on the same Fc site as FcεRI. Omalizumab causes a reduction in total serum IgE in atopic patients, which attenuates the amount of antigen-specific IgE that can bind to and sensitize tissue mast cells and basophils. This, in turn, leads to a decrease in symptoms of allergic diseases.

While Omalizumab reduces the amount of free IgE (the unbound form present in the circulation) it does not bind to IgE already bound to effector cells nor does it bind to membrane-anchored IgE. Thus, while neutralizing anti-IgE antibodies, like Omalizumab, may reduce the severity of some IgE-mediated allergic diseases they may not be effective for treating patients with very high levels of soluble IgE. Nor will they likely be effective for the treatment of diseases caused by monoclonal expansion of B-cells, such as, Job's disease. Strategies to treat these diseases focus on depleting the B-cells producing IgE for example, by binding membrane-anchored IgE present on the surface of B-cells and targeting these cells for destruction by a variety of mechanisms including the use of cytotoxic agents and mediating cell killing pathways such as antibody dependent cell-mediated cytotoxicity (ADCC) and complement dependent cytotoxicity (CDC). These methods would be efficacious for both the treatment of IgE-mediated allergic disease as well as for disease caused by the expansion of IgE expressing B-cells. Furthermore, these methods could be adapted to treat other diseases caused by monoclonal expansion of B-cells expressing other membrane-anchored immunoglobulins such as, for example, IgM expressing B-cells in Waldenstrom Macroglubulinemia, IgA and IgG expressing B-cells in various myelomas and autoimmune diseases and IgM and IgA expressing B-cells in neuropathy and nephropathy, post transplant lymphoproliferative disorder (PTLD), and monoclonal gammopathy of unknown significance (MGUS).

There are two forms of immunoglobulins: the secreted and the membrane anchored form. The membrane-anchored form differs from the secreted form in that the former has a membrane-anchoring peptide extending from the C terminus of the heavy-chain. Membrane-anchored immunoglobulin on B-cells is critical for B-cell functions. It can transduce signals for resting B cells to differentiate into activated lymphoblasts and Ig-secreting plasma cells. The amino acid sequences of many membrane-anchored immunoglobulins are known. These sequences share certain common features including the presence of a membrane anchoring peptide. The membrane anchoring peptide has three segments that are distinguishable based on their locations in relation to the plasma membrane (extracellular segment, transmembrane segment, and cytoplasmic segment). The N-terminal segment (extracellular segment) of the anchoring peptides is often designated as hydrophilic and highly acidic. This segment can be easily identified by amino acid sequence comparison and analysis and is referred to as the membrane-anchored immunoglobulin isotype specific ("migis") peptide or epitope (see FIG. 1A).

The migis peptides are unique for the different immunoglobulin isotypes. Therefore, the extracellular segment of the ε-chain membrane anchoring peptide forms, in whole or in part, an epitope unique to the B cells which produce IgE. The same is true for each immunoglobulin isotype. Furthermore, the migis peptide is not present on secreted, soluble immunoglobulin because only the immunoglobulin which is bound to the surface of B cells contains the membrane anchoring peptide as part of its heavy chain. Thus, therapeutics which specifically targeted the migis peptides would be useful to target specific classes of B-cells for the treatment of a wide variety of conditions including allergic diseases and those mediated by monoclonal B-cell expansion.

Membrane anchored IgE is found in at least two isoforms as a result of alternative splicing in humans. The ε-chain of both isoforms of human mIgE contains a ε-migis epitope and a membrane-anchoring peptide. One isoform contains only the ε-migis sequence (a 15-amino-acid-long domain) between the membrane anchor sequence and the C4 region, referred to as the short form. Whereas, the second isoform additionally contains an extra 52-amino-acid (a.a.)-long domain, referred to as cεmx, between the CH4 domain and the ε-migis sequence, referred to as the long form (see FIG. 2). Several groups have generated mouse monoclonal antibodies that bind to either the ε-migis peptide (see, e.g., Chang et al. U.S. Pat. Nos. 5,422,258 and 5,091,313) or an 8 amino acid cεmx peptide (Chen et al. 2002, Int Arch Allergy Immunol 128:315-24). However, as demonstrated herein (see Section 6, Example 1), antibodies that recognize the ε-migis peptide alone are likely to cross react with another commonly expressed cell surface protein, while those which interact with a predominant epitope present on the 8 amino acid cεmx peptide may in fact be hidden when the immunoglobulin is present on the membrane. Furthermore, it is not desirable to use mouse antibodies directly as a human therapeutic due to the generation of human-anti-mouse antibodies (HAMA) or HAMA response. Thus, antibodies of non-human origin are preferably engineered to "humanize" them to prevent eliciting a HAMA response. The process of humanization is not only time consuming but often results in an antibody with altered binding characteristics that is not a useful therapeutic. The antibodies disclosed herein are fully human antibodies which bind a unique ε-chain migis epitope not previously described.

Citation or discussion of a reference herein shall not be construed as an admission that such is prior art to the present invention.

3. SUMMARY OF THE INVENTION

The present invention is based in part on the discovery of antibodies that specifically bind novel epitopes comprising at least a portion of an ε-migis peptide and a portion of the cεmx peptide, exemplified by SEQ ID NO: 5. The novel epitopes of the invention are referred to herein, for example, as "cεmx.migis epitope," "cεmx.migis peptide," or simply as "cεmx.migis," and antigenic fragments thereof. The novel epitopes of the invention are also encompassed, for example, by the more expansive terms "cεmx.migis epitopes of the invention," or "cεmx.migis peptides of the invention." Antibodies that specifically bind novel cεmx.migis epitopes of the invention are specifically referred to herein as "cεmx.migis antibodies" and are also encompassed by the more expansive term "antibodies of the invention." The present invention also provides methods for the isolation of antibodies that bind novel epitopes and methods of using the antibodies of the invention, for example, to treat IgE-mediated diseases.

Further, the present invention relates to the isolation of antibodies which specifically bind membrane-anchored Ig molecules (mIgs) including but not limited to membrane-anchored IgE molecules (mIgEs). In a specific embodiment, the epitope recognized by antibodies which specifically bind mIgs include, but are not limited to, those described herein (e.g., SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46).

In another specific embodiment the antibodies which specifically bind mIgs including but not limited to mIgE (referred herein as antibodies of the invention) are human antibodies. In still another specific embodiment, antibodies of the invention mediate ADCC and/or CDC activity.

In yet another specific embodiment, antibodies of the invention are useful for the treatment of IgE-mediated disease and B-cell mediated diseases including, but not limited to, asthma, allergic diseases, and diseases caused by monoclonal expansion of B-cells such as, Job's disease.

4. BRIEF DESCRIPTION OF THE FIGURES

FIG. 1. The Human Migis Peptides. Panel A provides the amino acid sequence of the 5 different human migis peptides the numbers in parenthesis indicate the percent homology of each peptide to that of IgE migis. Panel B depicts the alignment of the ε-migis peptide with the μ-migis peptide. Solid lines indicate identity, dashed lines indicated similarity. The μ-migis peptide share about 31% homology with ε-migis, with 4 identical residues and 5 similar residues over a 12 amino acid stretch. Also shown is the alignment of the ε-migis peptide with peptides from Phosphoinositide binding protein and from the predicted open reading frame of KIAA1227, solid lines represent homology and the non-homologous amino acids are indicated. 8 out of 11 amino acids are identical between the phosphoinositide binding protein peptide and part of the ε-migis peptide, while 8 out of 9 are identical between the KIAA1227 peptide and part of the ε-migis peptide.

FIG. 2. Schematic of The ε-Chain Long And Short Splice Variants. The open box represents the variable region through the CH4 region, the hatched box represents the intracellular domain (ICD), the shaded box represents the transmembrane domain (TM), the striped box represents the ε-migis domain all of which are present in both the long and short forms. The stippled box represents the cεmx region which is present only in the long form. The amino acid sequence of the cεmx.migis peptide used for panning is shown in black and grey indicating those residues derived from the cεmx and ε-migis domains, respectively.

Figure 3:
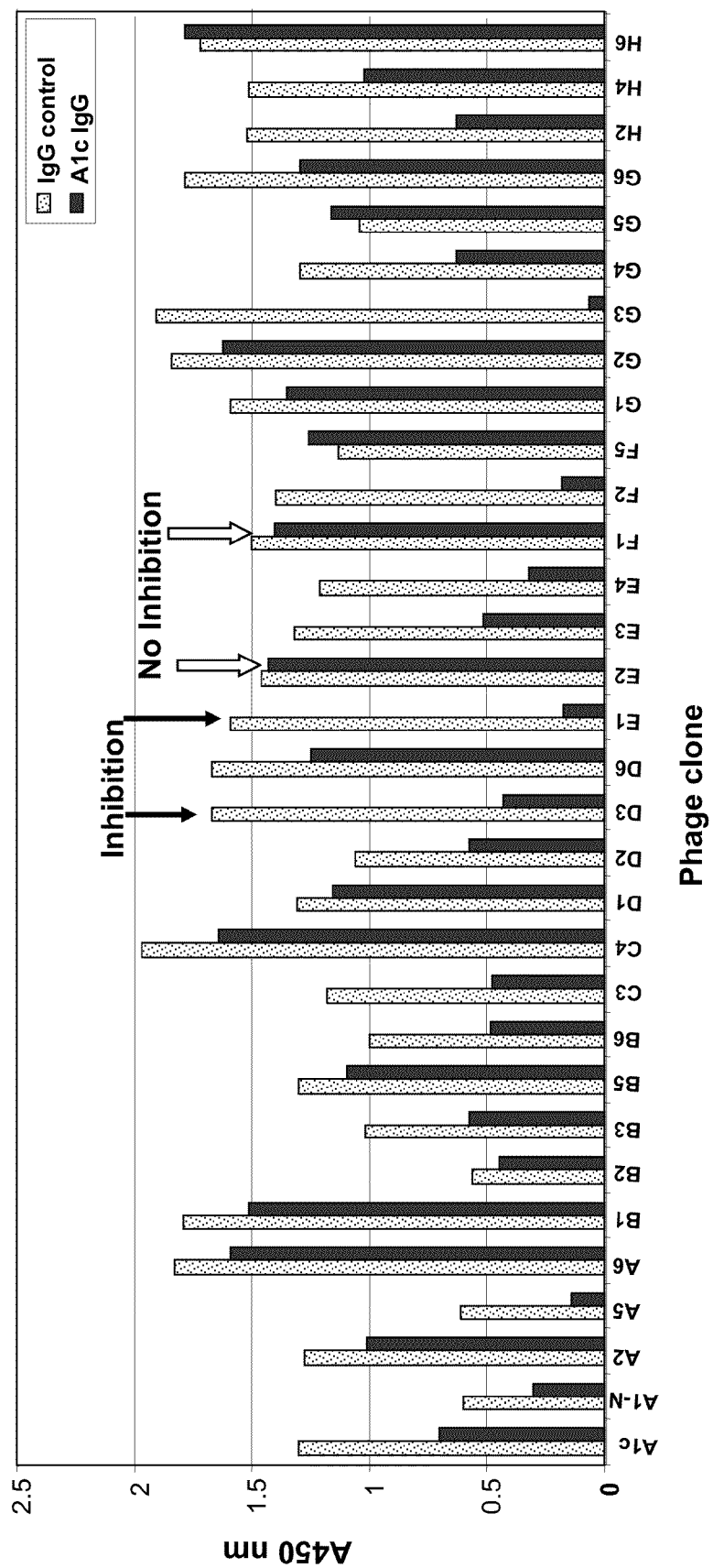

FIG. 3. Phage Binding Inhibition By The A1c Antibody Of Phage Clones Isolated Via cεmx.migis Panning. The amount of binding seen for several phage clones in the presence of an irrelevant isotype control antibody is shown by the stippled boxes. The shaded boxes show the binding of the same clone in the presence of the A1c antibody which is known to bind to the "shared-epitope" of ε-migis. The solid arrows indicate exemplary clones which are inhibited by A1c while the open arrows are exemplary clones which are not inhibited by A1c.

Figure 4:
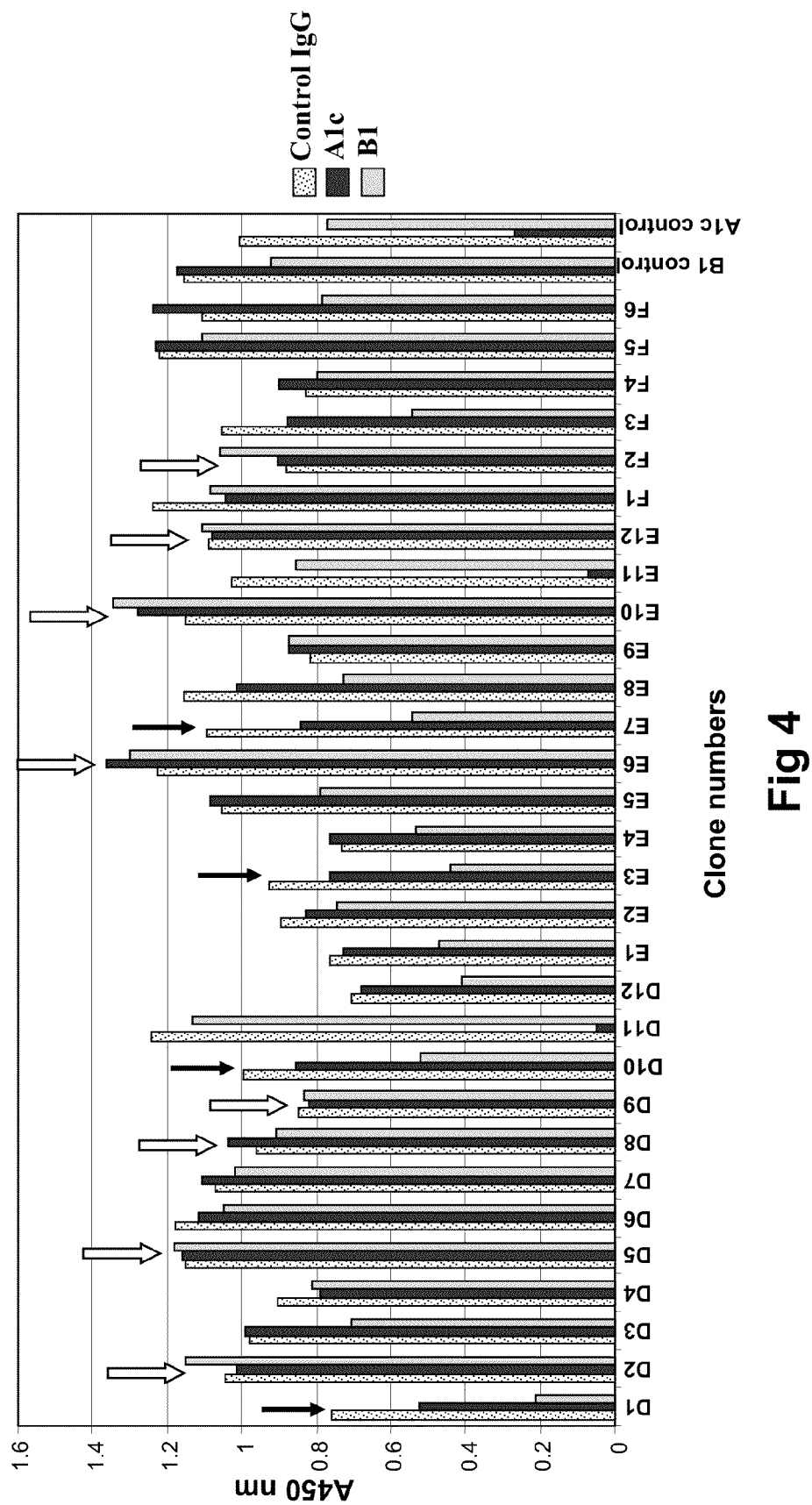

FIG. 4. Phage Binding Inhibition By The A1c and B1 Antibodies Of Phage Clones Isolated Via cεmx.migis Panning. The amount of binding seen for several phage clones in the presence of an irrelevant isotype control antibody is shown by the stippled boxes. The dark shaded boxes show the binding of the same clone in the presence of the A1c antibody which is presumed to bind to the "shared-epitope" of ε-migis. The light shaded boxes show the binding of the same clone in the presence of the B1 antibody which is presumed to bind to an epitope hidden on mIgE (referred to as "hidden-epitope")

of cεmx.migis. The solid arrows indicate clones which are inhibited by both A1c and B1 while the open arrows are clones which are not inhibited by either Ac1 or B1.

Figure 5:
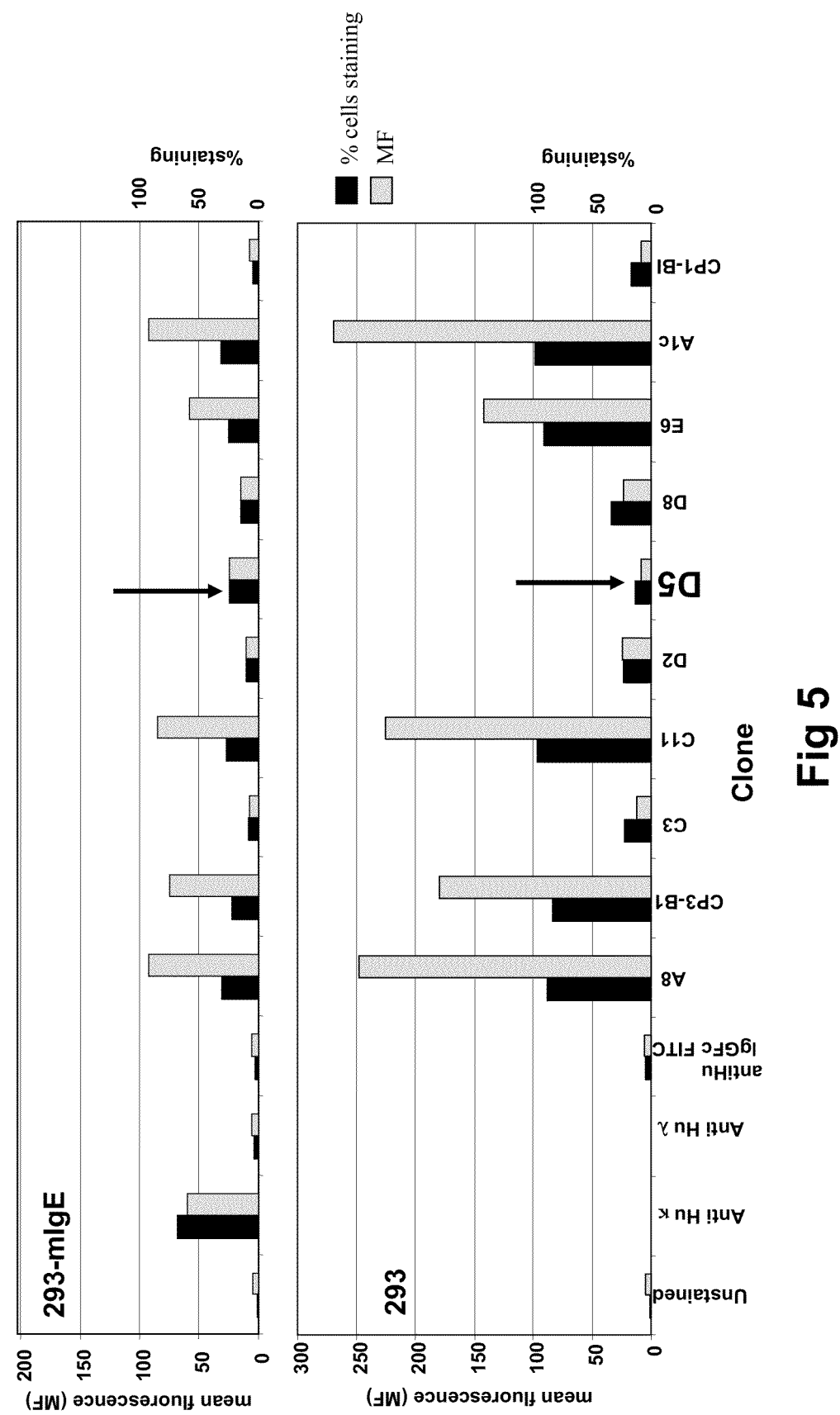

FIG. 5. FACS Analysis of Cell Surface Binding of Full Length IgGs Generated From Non-Inhibited Phage Clones. The solid bars indicated the percent (%) of cell staining while the shaded bars represent the mean channel fluorescence (MCF). For a clone that specifically bound to the ε-chain present only on the cells surface of transfected 293 cells (293-mIgE) both the percent of cells staining and the mean channel fluorescence should go down in untransfected 293 cells. Clone, D5 (indicated by an arrow), shows such a staining pattern.

Figure 6A:
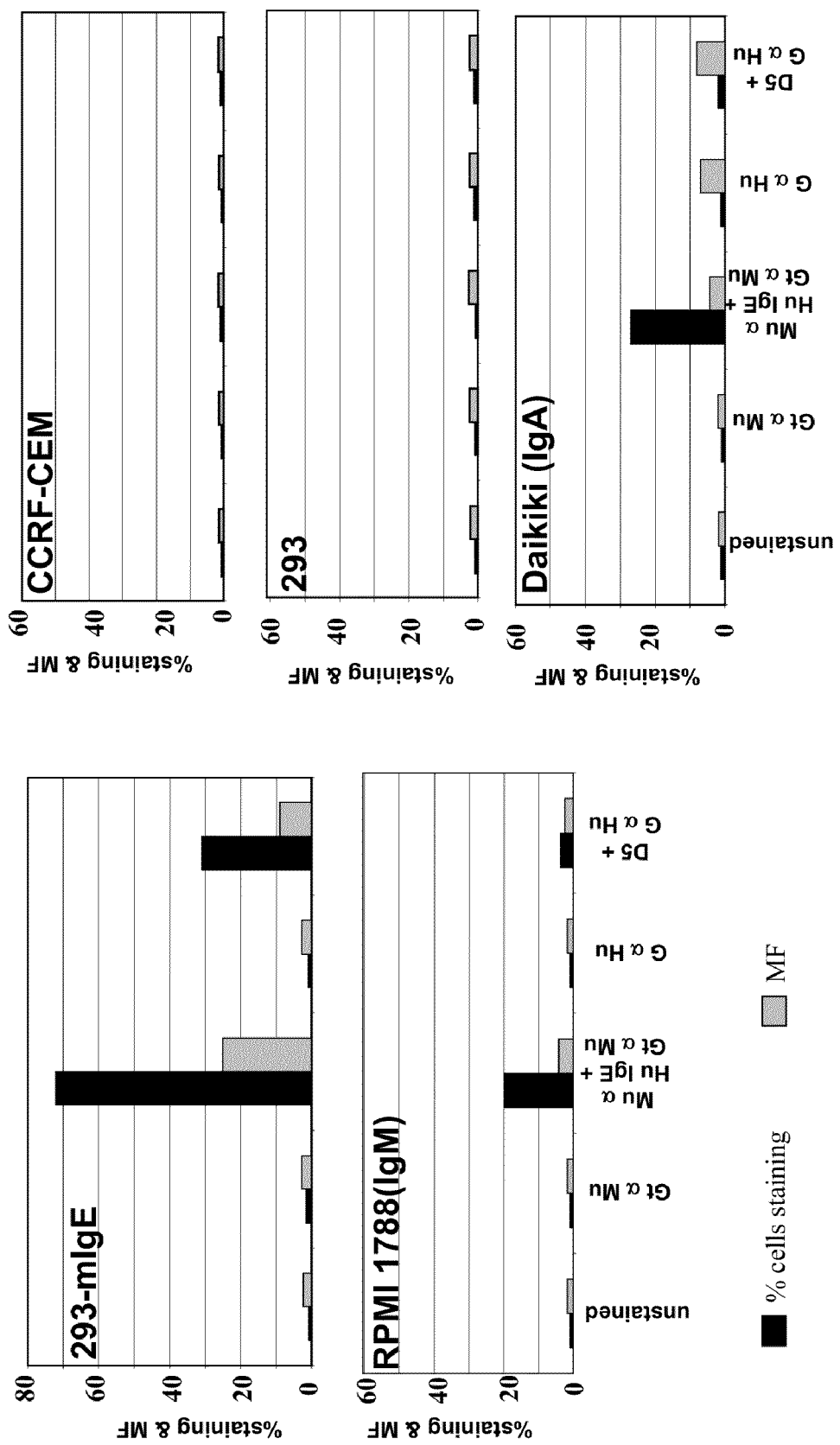

FIG. 6. FACS Analysis of Cell Surface Binding of D5 IgG. Panel A) The solid bars indicated the percent (%) of cell staining while the shaded bars represent the mean channel fluorescence (MCF). Panel B) Plotted is the MCF of unstained cells (grey bars) and cells stained with D5 (dark bars) or a secondary antibody control (speckled bars), several different cell types were examined as described below. Specific staining is indicated by staining (MCF value) with D5 but not by the secondary control antibody. Together these data demonstrate that D5 stains cells which express membrane anchored IgE (239H-mIgE) but does not significantly stain cells expressing other immunoglobulins such as IgA (Daikiki cells) or IgM (RPMI 1788 cells) or cells not expressing any immunoglobulin such as untransfected 293 cells and CCRF-CEM (a T cell line) or RAJI cells. D5 was not seen to stain SKO-007 cells which have been reported to express mIgE but in a rather weak and unstable manner.

Figure 7A:
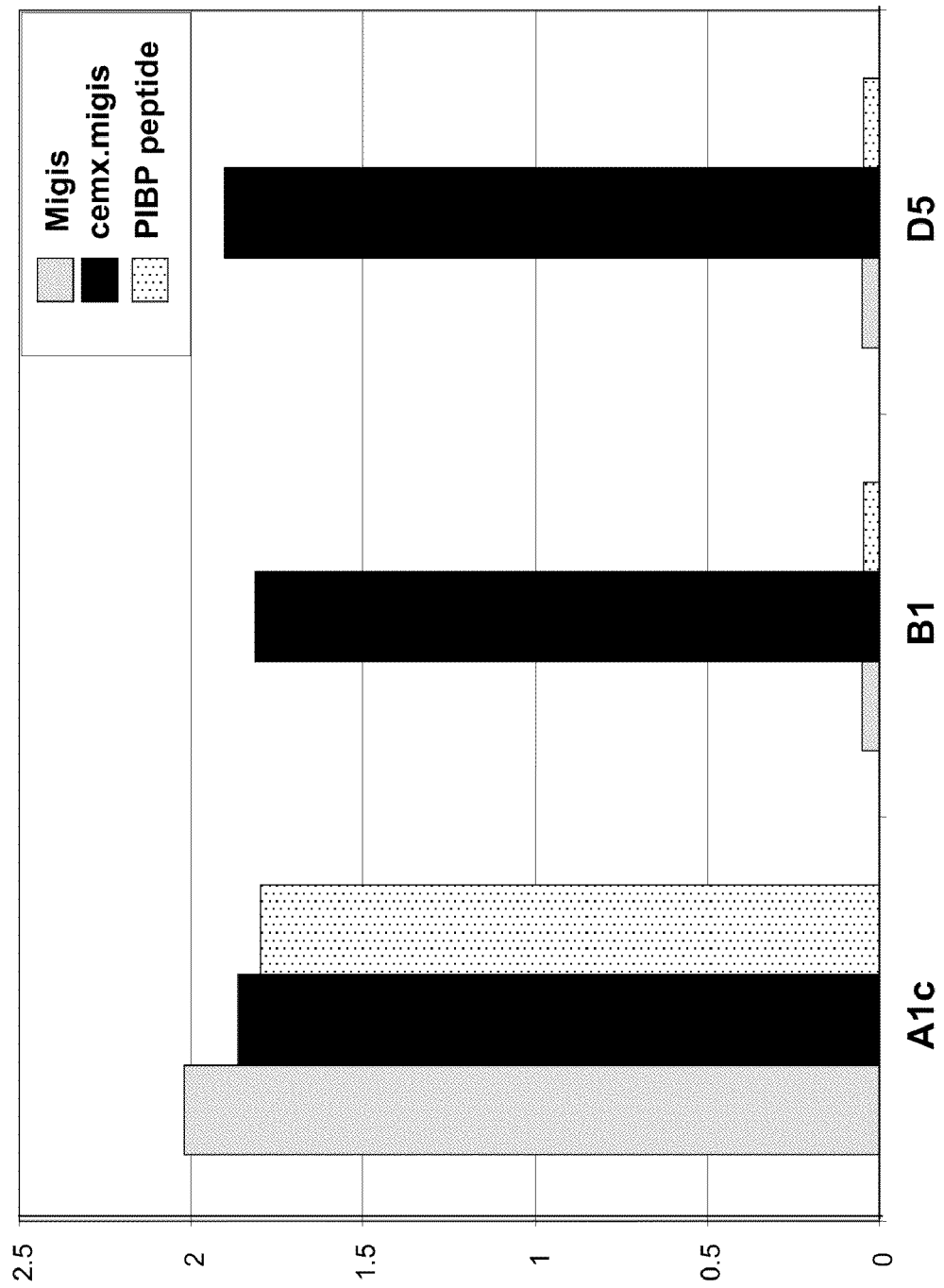
Figure 7B:
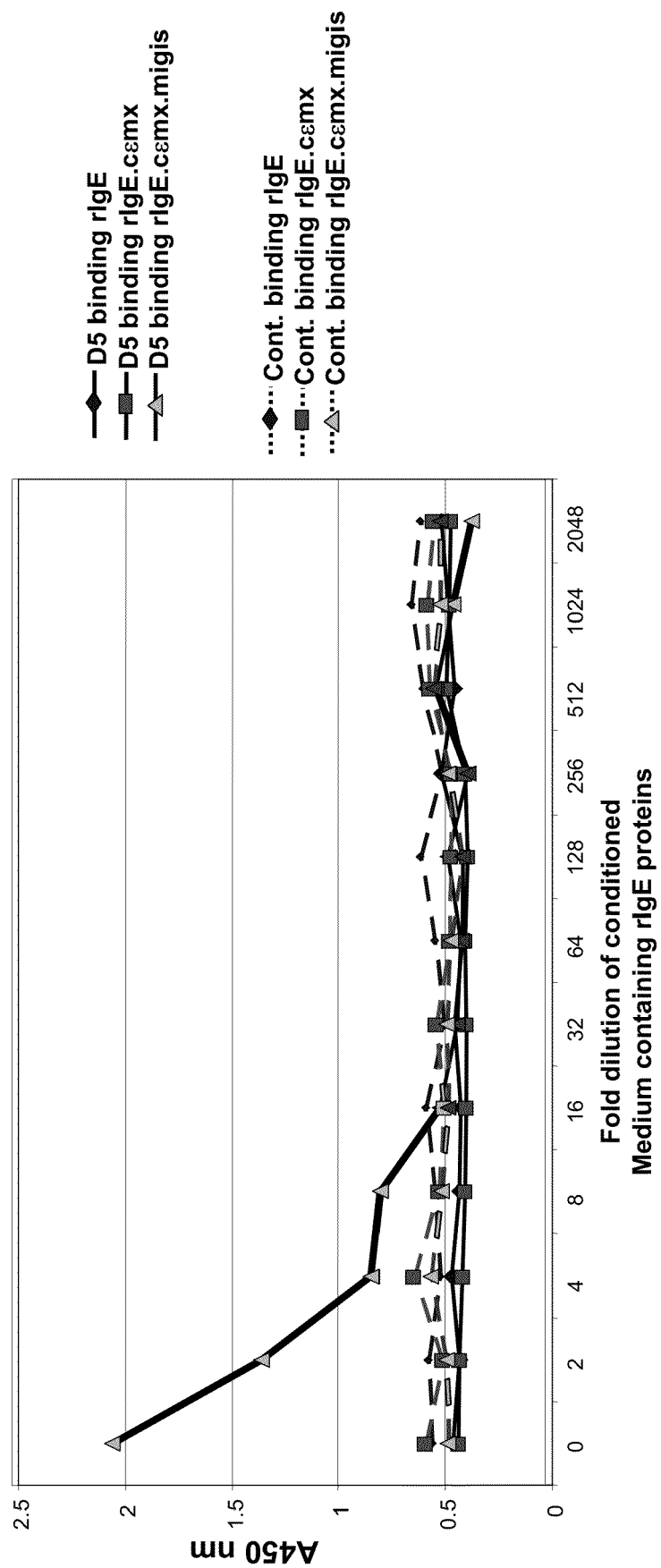
Figure 7C:
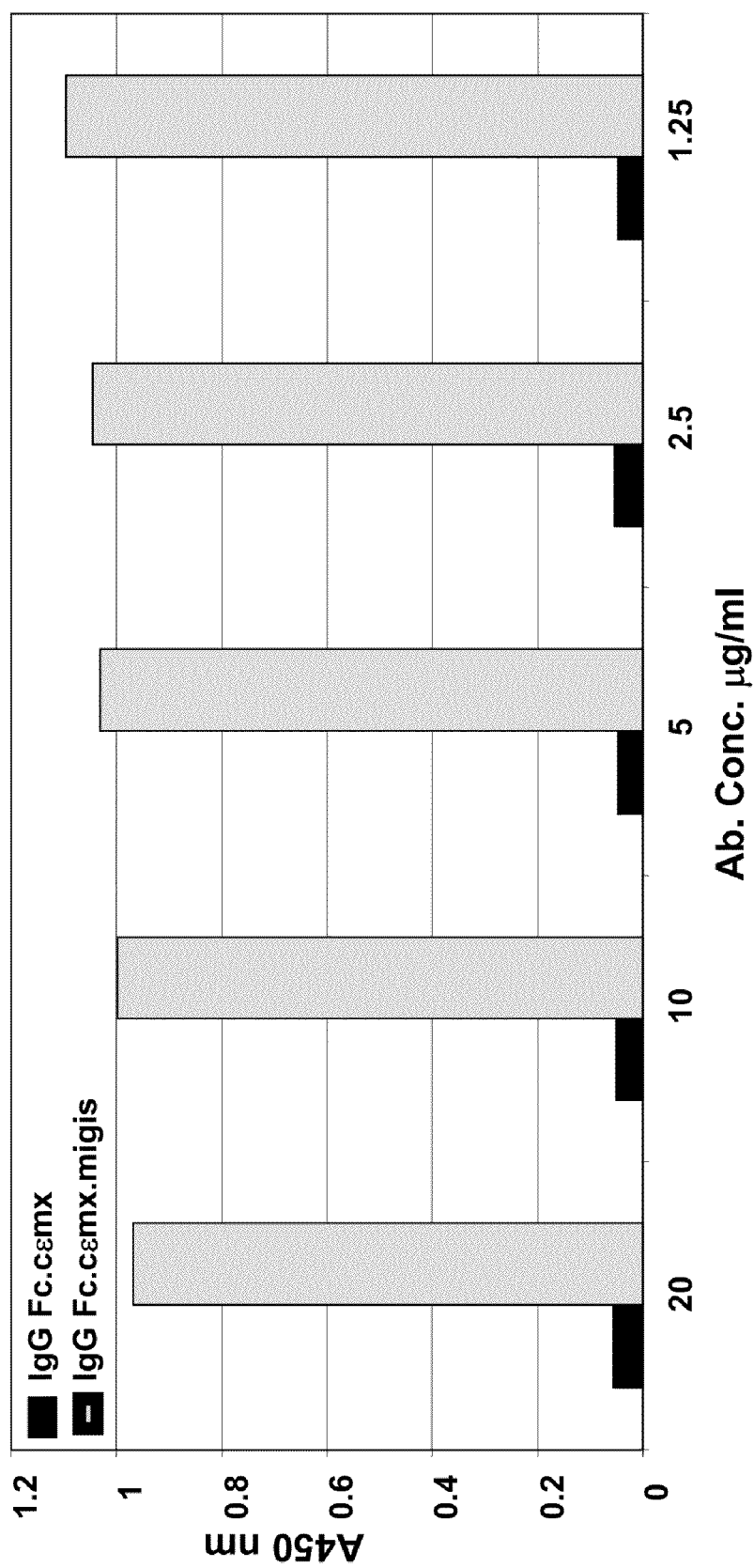

FIG. 7. ELISA Analysis of D5 IgG Binding. Panel A) ELISA binding assay showing that D5 and B1 only bind to the cεmx.migis peptide while A1c binds to an ε.migis peptide, a cεmx.migis peptide and a peptide corresponding to the region of the phosphoionositide binding protein that is similar to ε-migis (PIBP peptide) with nearly equal affinity. Panel B) ELISA binding assay of D5 IgG to Recombinant IgE, IgE.cεmx and IgE.cεmx.migis. The binding curves for serial dilutions of D5 IgG or a control antibody are represented by the solid and dotted lines respectively. The diamonds indicate binding to rIgE, the squares represent biding to rIgE.cεmx and the triangles represent binding to rIgE.cεmx.migis. D5 IgG binds only rIgE.cεmx.migis, the control antibody did not bind to any of the rIgE proteins. Panel C) ELISA Analysis of D5 IgG Binding to Recombinant Full length IgG-Fc fused to either cεmx (IgG.Fc.cεmx) or cεmx.migis (IgG.Fc-.cεmx.migis). Binding of D5 at concentrations of 1.25 to 20 μg/ml to IgG.Fc.cεmx and IgG.Fc.cεmx.migis are shown by the dark and light bars, respectively. D5 IgG only binds to the IgG.Fc.cεmx.migis molecule at each concentration examined.

Figure 8:
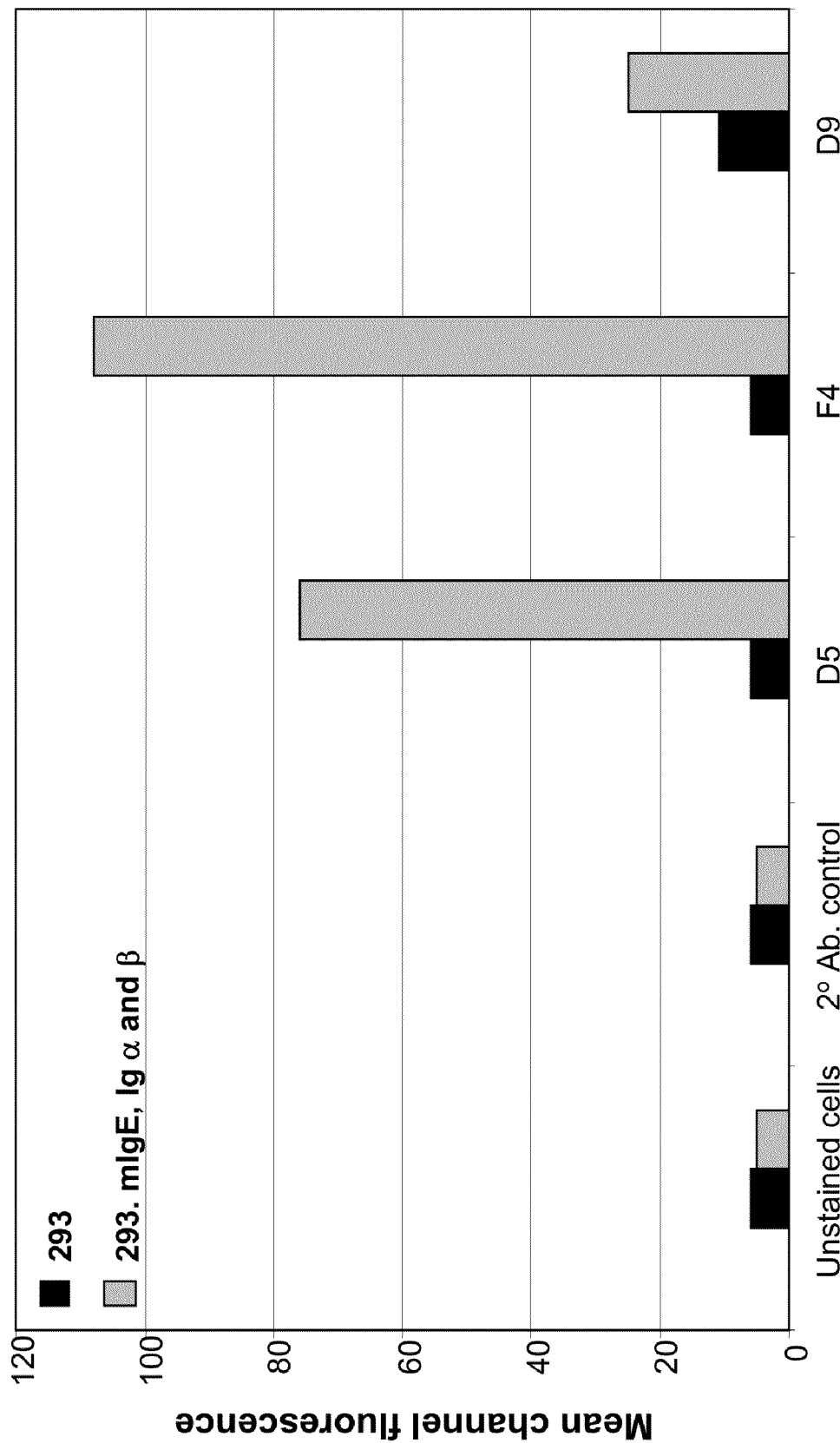

FIG. 8. D5, F4 and D9 Selective Bind to The Cell Surface of Cells Expressing mIgE. The mean channel fluorescence is plotted for unstained cells and cells stained either D5, F4, D9 and a secondary control antibody. The D5, F4 and D9 antibodies each selectively stain only 293 cells expressing mIgE, Igα and Igβ (grey bars) and not untransfected 293 cells (black bars).

FIG. 9. BIAcore Analysis of D5 IgG Binding to the cεmx.migis and ε-migis peptides. The top trace represents the binding of the D5 IgG antibody to cεmx.migis while the bottom trace represents the binding of the D5 antibody to ε-migis. D5 IgG only binds to cεmx.migis.

Figure 10A:
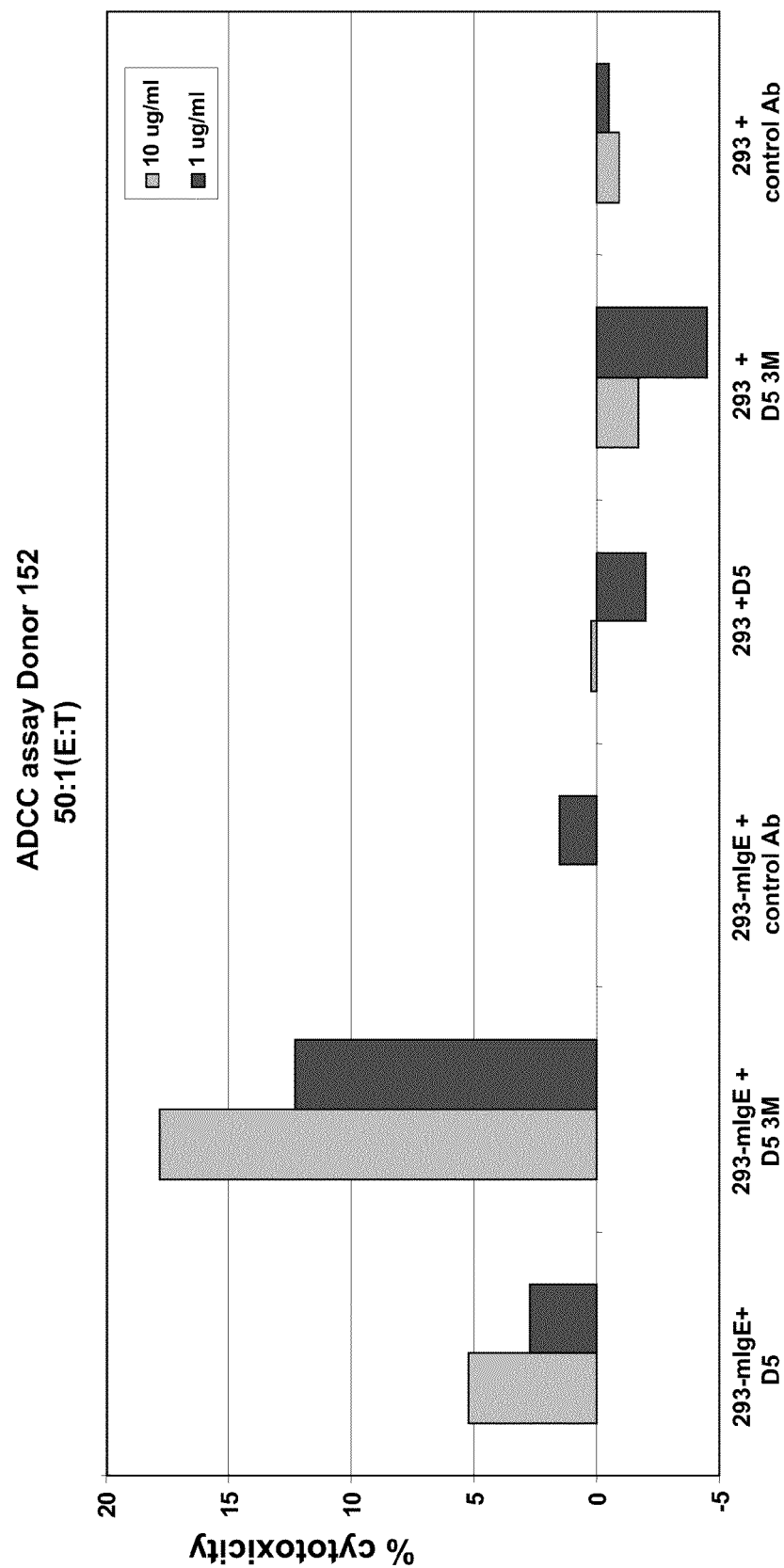
Figure 10B:
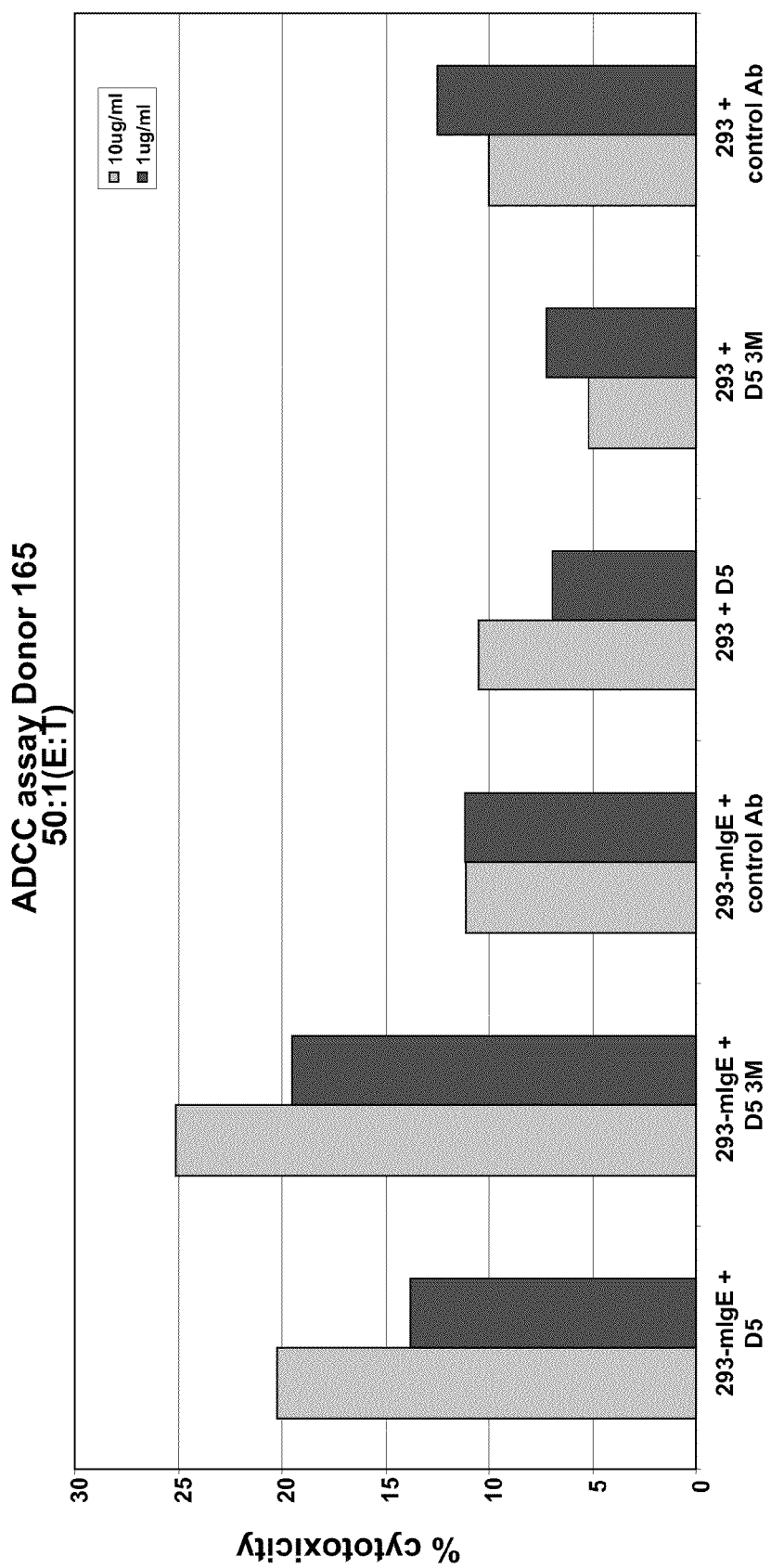

FIG. 10. ADCC activity of D5 IgG and the Fc-variant D53M as Measured by Cell-based ADCC assay. Panel A are the results from donor 152. Panel B are the results from donor 165. D5 IgG was seen to have higher ADCC activity only in cells expressing IgE on their membranes (293-mIgE). The assay was performed using 50:1 ratio of effector to target cells at antibody concentrations of 1 μg/ml and 10 μg/ml (shaded and dark bars respectively). The Fc-variant D53M was seen to have more ADCC activity then D5 IgG. Panel C are the results using three 293 cell line clones (1, 2 and 5) stably expressing mIgE, Igα and Igβ. D5 IgG has higher ADCC activity against all three cell lines expressing mIgE as compared to a control IgG. The assay was performed using antibody concentrations of 1 μg/ml, 10 μg/ml and 100 μg/ml (speckled, shaded and dark bars respectively). D5 was seen to have as much as 70% cytotoxicity was seen for the highest antibody concentrations as compared to ~35% seen for control antibodies. The control antibody does not show any difference in ADCC activity between cells not expressing mIgE (293 cells) and those that do (clones 1, 2 and 5).

Figure 11:
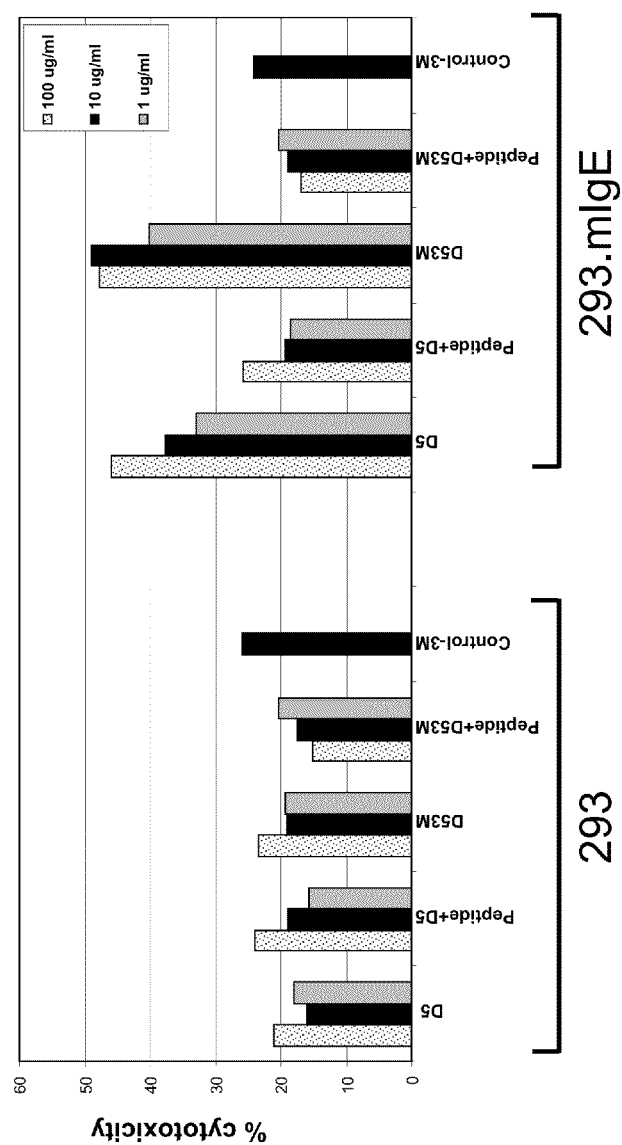

FIG. 11. ADCC activity of D5 IgG and the Fc-variant D53M IgG as Measured by Cell-based ADCC assay. Both D5 IgG and the Fc variant, D53M IgG were seen to specifically enhance ADCC in cells expressing IgE on their membranes. This activity could be specifically competed by the addition of the cεmx.migis peptide. In contrast, the activity of a control Fc-variant antibody did not depend on membrane expression of IgE. Three antibody concentrations were used 1 μg/ml (shaded bars), 10 μg/ml (black bars) and 100 μg/ml (stippled bars). The Fc-variant D53M IgG was seen to have more ADCC activity than D5 IgG.

Figure 12B:
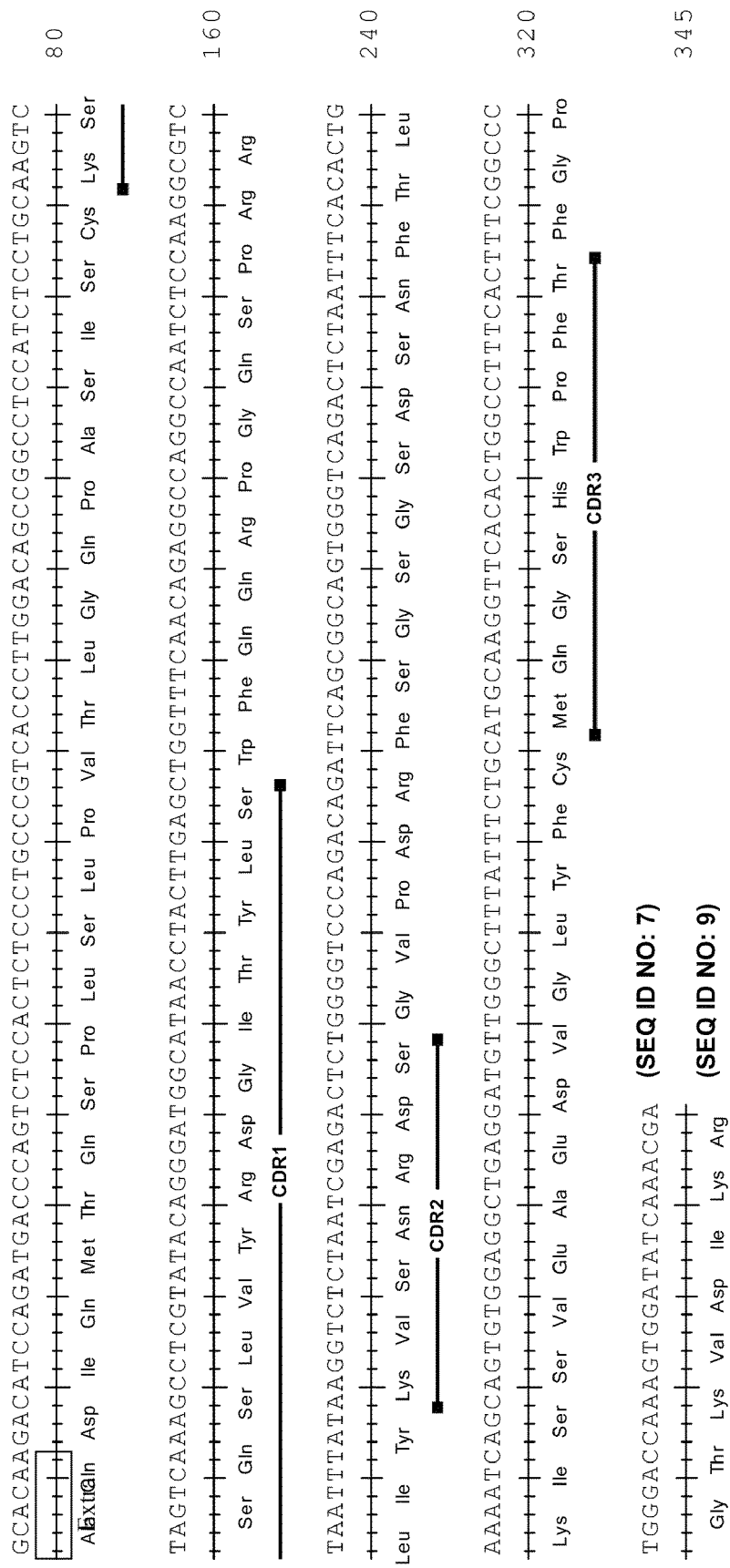

FIG. 12. The nucleotide and deduced amino acid sequence of the variable region of the D5 antibody (A) heavy chain variable region (SEQ ID NO: 8 and SEQ ID NO: 10, respectively) (B) light chain variable region (SEQ ID NO: 7 and SEQ ID NO: 9, respectively). The CDRs are underlined (see Table 1 for corresponding SEQ ID NOS.).

FIG. 13. The nucleotide and deduced amino acid sequence of the variable region of the A1c antibody (A) heavy chain variable region (SEQ ID NO: 51 and SEQ ID NO: 53, respectively) (B) light chain variable region (SEQ ID NO: 50 and SEQ ID NO: 52, respectively). The CDRs are underlined (see Table 1 for corresponding SEQ ID NOS.).

Figure 14B:
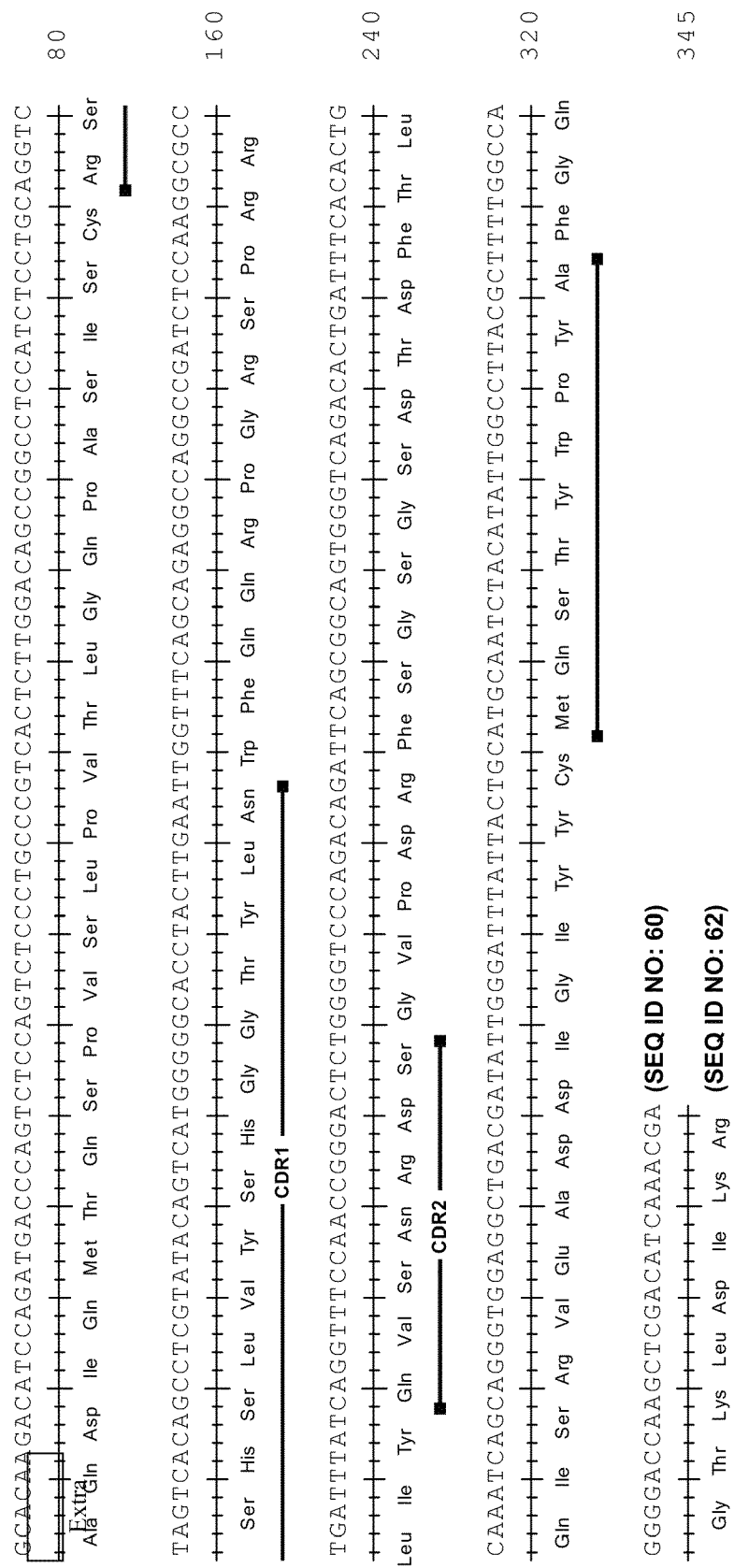

FIG. 14. The nucleotide and deduced amino acid sequence of the variable region of the B1 antibody (A) heavy chain variable region (SEQ ID NO: 61 and SEQ ID NO: 63, respectively) (B) light chain variable region (SEQ ID NO: 60 and SEQ ID NO: 62, respectively). The CDRs are underlined (see Table 1 for corresponding SEQ ID NOS.).

FIG. 15. The nucleotide and deduced amino acid sequence of the variable region of the F4 antibody (A) heavy chain variable region (SEQ ID NO: 71 and SEQ ID NO: 73, respectively) (B) light chain variable region (SEQ ID NO: 70 and SEQ ID NO: 72, respectively). The CDRs are underlined (see Table 1 for corresponding SEQ ID NOS.).

FIG. 16. The nucleotide and deduced amino acid sequence of the variable region of the D9 antibody (A) heavy chain variable region (SEQ ID NO: 80 and SEQ ID NO: 81, respectively). The CDRs are underlined (see Table 1 for corresponding SEQ ID NOS.).

Figure 17:
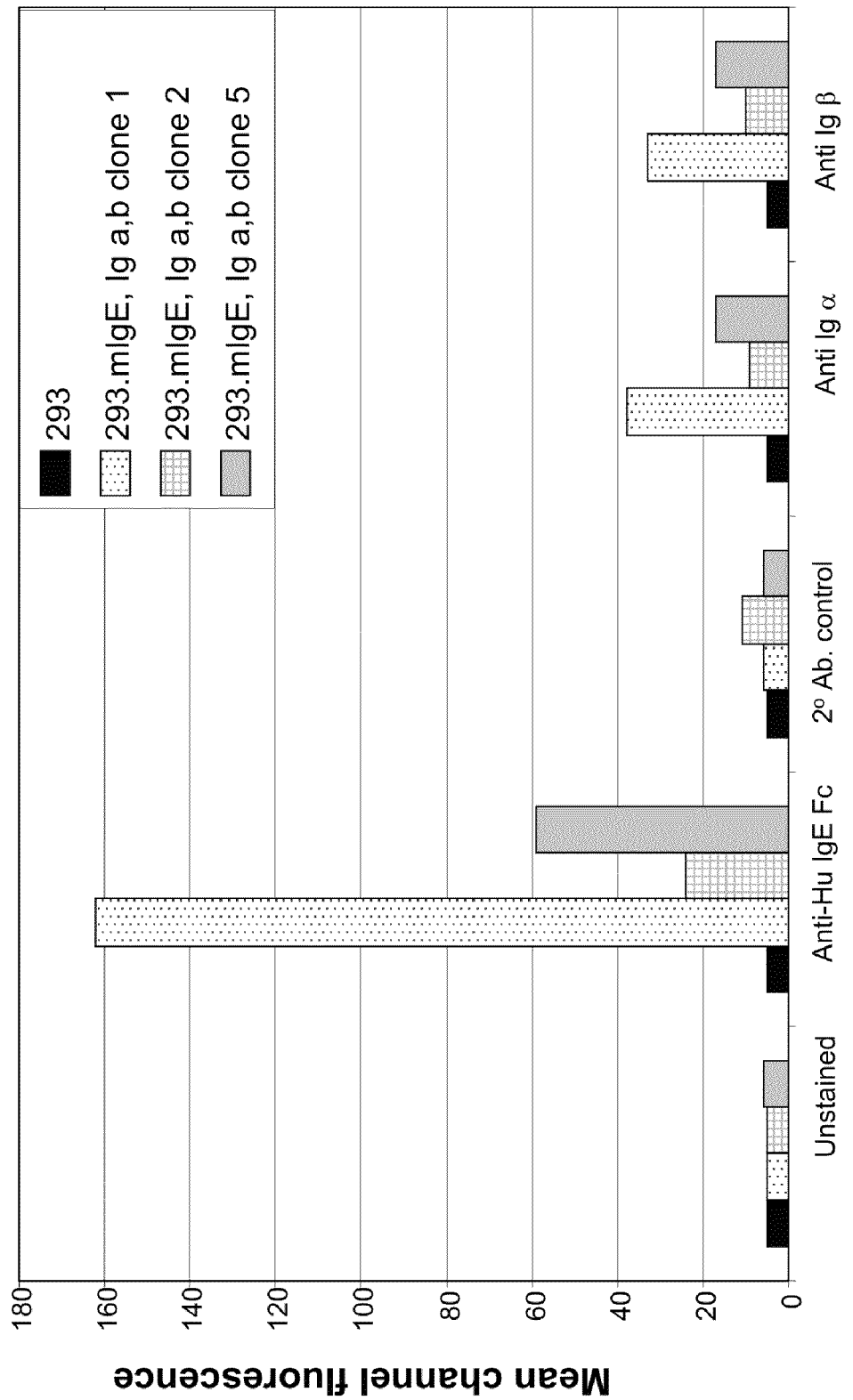

FIG. 17. Stable Transfected 293 Cells Express mIgE, Igα and Igβ On Their Cell Surface. Plotted is the mean channel fluorescence of cell surface staining with anti-hu IgE, anti-Igα, anti-Igβ and a secondary antibody control demonstrating that clones 1, 2 and 5 stain for all three cell surface markers while control cells do not.

5. DETAILED DESCRIPTION

The present invention is based in part on the discovery of antibodies that specifically bind novel epitopes comprising at least a portion of an ε-migis peptide and a portion of the cεmx peptide, exemplified by SEQ ID NO: 5. The novel epitopes of the invention are referred to herein, for example, as "cεmx.migis epitope," "cεmx.migis peptide," or simply as "cεmx.migis," and antigenic fragments thereof. The novel epitopes of the invention are also encompassed by the more expansive terms "migis epitopes of the invention," and "migis epitopes." Antibodies that specifically bind novel cεmx.migis epitopes of the invention are specifically referred to herein as "cεmx.migis antibody(ies)" and are also encompassed by the more expansive term "antibody(ies) of the invention." The present invention also provides methods for the isolation of antibodies that bind novel epitopes and methods of using the antibodies of the invention, for example, to treat IgE-mediated diseases.

The cεmx.migis epitope to which the antibodies of the present invention specifically bind to is present on membrane anchored IgE (abbreviated herein as "mIgE"). In one embodiment, the cεmx.migis antibodies that specifically bind the novel cεmx.migis epitope bind to mIgE. In another embodiment, antibodies of the invention which bind to mIgE mediate ADCC and/or CDC activity.

In one embodiment, an antibody of the invention specifically binds the peptide sequence of human cεmx.migis peptide sequence (SEQ ID NO:5). In another embodiment, an antibody of the invention specifically binds to membrane-anchored IgE (mIgE). In a specific embodiment, an antibody of the invention that specifically binds the peptide sequence of SEQ ID NO:5 does not bind membrane-anchored immunoglobulins (referred to herein jointly as "mIgs", and individually as "mIgG", "mIgA", "mIgE", "mIgM" and "mIgD") other than mIgE. In another specific embodiment, an antibody of the invention that specifically binds the peptide sequence of SEQ ID NO:5 does not bind the peptide sequence of human ε-migis (SEQ ID NO:1) and/or the human cεmx peptide sequence (SEQ ID NO:6). In still another specific embodiment, an antibody of the invention that specifically binds the peptide sequence of SEQ ID NO:5 does not bind the polypeptide of phosphoinositide binding protein epitope (SEQ ID NO:3) and/or the KIAA1227 peptide epitope (SEQ ID NO:4).

In one embodiment, an antibody of the invention that specifically binds the peptide sequence of SEQ ID NO:5 does not bind the same epitope as an antibody that specifically binds the peptide of SEQ ID NO:1. In another embodiment, an antibody of the invention that specifically binds the peptide sequence of SEQ ID NO:5 does not bind the same epitope as an antibody that specifically binds the peptide of SEQ ID NO:6. In still another embodiment, the binding of an antibody of the invention that specifically binds the peptide sequence of SEQ ID NO:5 to mIgE is not inhibited by the peptides of SEQ ID NO:1 and SEQ ID NO:6.

In one embodiment, an antibody of the invention that specifically binds the peptide sequence of SEQ ID NO:5 does not bind the same epitope as antibodies comprising the variable regions of A1c (encoded by SEQ ID NOS: 50 and 51) and B1 (encoded by SEQ ID NOS: 60 and 61). In another embodiment, an antibody of the invention that specifically binds the peptide sequence of SEQ ID NO:5 is not inhibited by antibodies comprising the variable regions of A1c (encoded by SEQ ID NOS: 50 and 51) and B1 (encoded by SEQ ID NOS: 60 and 61).

In one embodiment, an antibody of the invention that specifically binds a migis epitope (e.g., a cεmx.migis epitope) depletes B cells or plasma cells expressing mIgE. Depletion may occur in an in vitro assay designed to measure B cell or plasma cell depletion, or may occur in vivo in a subject. In a more specific embodiment, an antibody of the invention that specifically binds the peptide sequence of SEQ ID NO:5 depletes B cells or plasma cells expressing mIgE. In another specific embodiment, an antibody of the invention that specifically binds the peptide sequence of SEQ ID NO:5 depletes B cells or plasma cells expressing mIgE through ADCC. In still another specific embodiment, an antibody of the invention that specifically binds the peptide sequence of SEQ ID NO:5 depletes B cells or plasma cells expressing mIgE through CDC.

In one embodiment, an antibody of the invention specifically binds a peptide having an amino acid sequence selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46.

Antibodies or fragments that specifically bind to a peptide (e.g., cεmx.migis) can be identified, for example, by immunoassays, BIAcore, or other techniques known to those of skill in the art. An antibody or fragment thereof binds specifically to a migis epitope or a fragment thereof when it binds to a migis epitope or a fragment thereof with higher affinity than to any cross-reactive antigen as determined using experimental techniques, such as radioimmunoassays (RIA) and enzyme-linked immunosorbent assays (ELISAs). See, e.g., Paul, ed., 1989, Fundamental Immunology Second Edition, Raven Press, New York at pages 332-336 for a discussion regarding antibody specificity.

The present invention further encompasses antibodies of the invention that have a high binding affinity for a migis epitope (e.g., a cεmx.migis epitope). In a specific embodiment, an antibody of the invention that specifically binds to a migis epitope has an association rate constant or $k_{on}$ rate of at least $10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$. In another embodiment, an antibody of the invention that specifically binds to a migis epitope has a $k_{on}$ of at least $2 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$. In a particular embodiment, the migis epitope for which an antibody of the invention has a $k_{on}$ as disclosed herein is a cεmx.migis epitope. In another particular embodiment, the migis epitope for which an antibody of the invention has a $k_{on}$ as disclosed herein is a peptide selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46. In a specific embodiment, the migis epitope for which an antibody of the invention has a $k_{on}$ as disclosed herein is a peptide having the amino acid sequence of SEQ ID NO:5.

In another embodiment, an antibody of the invention that specifically binds to a migis epitope has a $k_{off}$ of less than $10^{-1} s^{-1}$, less than $5 \times 10^{-1} s^{-1}$, less than $10^{-2} s^{-1}$, less than $5 \times 10^{-2} s^{-1}$ less than $10^{-3} s^{-1}$ less than $5 \times 10^{-3} s^{-1}$ less than $10^{-4} s^{-1}$ less than $5 \times 10^{-4} s^{-1}$ less than $10^{-5} s^{-1}$ less than $5 \times 10^{-5} s^{-1}$, less than $10^{-6} s^{-1}$ less than $5 \times 10^{-6} s^{-1}$ less than $10^{-7} s^{-1}$ less than $5 \times 10^{-7} s^{-1}$, less than $10^{-8} s^{-1}$, less than $5 \times 10^{-8} s^{-1}$, less than $10^{-9} s^{-1}$, less than $5 \times 10^{-9} s^{-1}$, or less than $10^{-1} M^{-1} s^{-1}$. In another embodiment, an antibody of the invention that specifically binds to a migis epitope has a $k_{off}$ of less than $5 \times 10^{-4} s^{-1}$, less than $10^{-5} s^{-1}$, less than $5 \times 10^{-5} s^{-1}$ less than $10^{-6} s^{-1}$ less than $5 \times 10^{-6} s^{-1}$, less than $10^{-7} s^{-1}$ less than $5 \times 10^{-7} s^{-1}$ less than $10^{-8} s^{-1}$ less than $5 \times 10^{-8} s^{-1}$, less than $10^{-9} s^{-1}$ less than $5 \times 10^{-9} s^{-1}$, or less than $10^{-10} s^{-1}$. In a particular embodiment, the migis epitope for which an antibody of the invention has a $k_{off}$ as disclosed herein is a cεmx.migis epitope. In another particular embodiment, the migis epitope for which an antibody of the invention has a $k_{off}$ as disclosed herein is a peptide selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46. In a specific embodiment, the migis epitope for which an antibody of the invention has a $k_{off}$ as disclosed herein is a peptide having the amino acid sequence of SEQ ID NO:5.

In another embodiment, an antibody of the invention that specifically binds to a migis epitope has an affinity constant or $K_a$ ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$ at least $5 \times 10^8 M^{-1}$, at least $10^9 M^{-1}$ at least $5 \times 10^9 M^{-1}$, at least $10^{10} M^{-1}$ at least $5 \times 10^{10} M^{-1}$, at least $10^{11} M^{-1}$ at least $5 \times 10^{11} M^{-1}$, at least $10^{12} M^{-1}$, at least $5 \times 10^{12} M$, at least $10^{13} M^{-1}$ at least $5 \times 10^{13} M^{-1}$, at least $10^{14} M^{-1}$ at least $5 \times 10^{14} M^{-1}$, at least $10^{15} M^{-1}$ or at least $5 \times 10^{15} M^{-1}$. In a particular embodiment, the migis epitope for which an antibody of the invention has a $k_a$ as disclosed herein is a cεmx.migis epitope. In another particular embodiment, the migis epitope for which an antibody of the invention has a $k_a$ as disclosed herein is a peptide selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46. In a specific embodiment, the migis epitope for which an antibody of the invention has a $k_a$ as disclosed herein is a peptide having the amino acid sequence of SEQ ID NO:5.

In yet another embodiment, an antibody of the invention that specifically binds to a migis epitope has a dissociation constant or $K_d$ ($k_{off}/k_{on}$) of less than $10^{-2} M$, less than $5 \times 10^{-2} M$, less than $10^{-3} M$, less than $5 \times 10^{-3} M$, less than $10^{-4} M$, less than $5 \times 10^{-4} M$, less than $10^{-5} M$, less than $5 \times 10^{-5} M$, less than $10^{-6} M$, less than $5 \times 10^{-6} M$, less than $10^{-7} M$, less than $5 \times 10^{-7} M$, less than $10^{-8} M$, less than $5 \times 10^{-8} M$, less than $10^{-9} M$, less than $5 \times 10^{-9} M$, less than $10^{-10} M$, less than $5 \times 10^{-10} M$, less than $10^{-11} M$, less than $5 \times 10^{-11} M$ less than $10^{-12} M$, less than $5 \times 10^{-12} M$, less than $10^{-13} M$, less than $5 \times 10^{-13} M$, less than $10^{-14} M$, less than $5 \times 10^{-14} M$, less than $10^{-15} M$, or less than $5 \times 10^{-15} M$. In still another embodiment, an antibody of the invention that specifically binds to a migis epitope has a dissociation constant or $K_d$ ($k_{off}/k_{on}$) of between about $10^{-7} M$ and about $10^{-8} M$, between about $10^{-8} M$ and about $10^{-9} M$, between about $10^{-9} M$ and about $10^{-10} M$, between about $10^{-10} M$ and about $10^{-11} M$, between about $10^{-11} M$ and about $10^{-12} M$, between about $10^{-12} M$ and about $10^{-13} M$, between about $10^{-13} M$ and about $10^{-14} M$. In still another embodiment, an antibody of the invention that specifically binds to a migis epitope has a dissociation constant or $K_d$ ($k_{off}/k_{on}$) of between $10^{-7} M$ and $10^{-8} M$, between $10^{-8} M$ and $10^{-9} M$, between $10^{-9} M$ and $10^{-10} M$, between $10^{-10} M$ and $10^{-11} M$, between $10^{-11} M$ and $10^{-12} M$, between $10^{-12} M$ and $10^{-13} M$, between $10^{-13} M$ and $10^{-14} M$. In a particular embodiment, the migis epitope for which an antibody of the invention has a $k_d$ as disclosed herein is a cεmx.migis epitope. In another particular embodiment, the migis epitope for which an antibody of the invention has a $k_d$ as disclosed herein is a peptide selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46. In a specific embodiment, the migis epitope for which an antibody of the invention has a $k_d$ as disclosed herein is a peptide having the amino acid sequence of SEQ ID NO:5.

It is well known in the art that the equilibrium dissociation constant ($K_d$) is defined as $k_{off}/k_{on}$. It is generally understood that a binding molecule (e.g., and antibody) with a low $K_d$ is preferable to a binding molecule (e.g., and antibody) with a high $K_d$. However, in some instances the value of the $k_0$ or $k_{off}$ may be more relevant than the value of the $K_d$. One skilled in the art can determine which kinetic parameter is most important for a given antibody application. In certain embodiments, the antibodies of the invention have a lower $K_d$ for one antigen than for others.

In one embodiment, an antibody of the invention has at least 2, at least 5, at least 10, at least $10^2$, at least $5 \times 10^2$, at least $10^3$, at least $5 \times 10^3$, at least $10^4$, at least $5 \times 10^4$, at least $10^5$, at least $5 \times 10^5$, or at least $10^6$ fold lower Kd for a peptide having the amino acid sequence of SEQ ID NO:5 compared to the Kd for a peptide having the amino acid sequence of SEQ ID NO:1.

In one embodiment, an antibody of the invention has at least 2, at least 5, at least 10, at least $10^2$, at least $5 \times 10^2$, at least $10^3$, at least $5 \times 10^3$, at least $10^4$, at least $5 \times 10^4$, at least $10^5$, at least $5 \times 10^5$, or at least $10^6$ fold lower Kd for a peptide having the amino acid sequence of SEQ ID NO:5 compared to the Kd for a peptide having the amino acid sequence of SEQ ID NO:6.

In one embodiment, an antibody of the invention has at least 2, at least 5, at least 10, at least $10^2$, at least $5 \times 10^2$, at least $10^3$, at least $5 \times 10^3$, at least $10^4$, at least $5 \times 10^4$, at least $10^5$, at least $5 \times 10^5$, or at least $10^6$ fold lower Kd for a peptide having the amino acid sequence of SEQ ID NO:5 compared to the Kd for a peptide having the amino acid sequence of SEQ ID NO:1 and a peptide having the amino acid sequence of SEQ ID NO:6.

The present invention comprises antibodies that specifically bind to a peptide having the amino acid sequence of SEQ ID NO:5. The present invention also provides antibodies that specifically bind to membrane-anchored IgE (mIgE). In certain embodiments, an antibody of the invention binds to a peptide having the amino acid sequence of SEQ ID NO:5 and binds to mIgE. In one embodiment an antibody of the invention that specifically bind to a peptide having the amino acid sequence of SEQ ID NO:5 and/or specifically binds to mIgE comprises a variable light chain ($V_L$) domain of SEQ ID NO:9. In a particular embodiment, an antibody of the invention that specifically bind to a peptide having the amino acid sequence of SEQ ID NO:5 and/or specifically binds to mIgE comprises a $V_L$ domain encoded by the nucleotide of SEQ ID NO: 7. In another embodiment, an antibody of the invention that specifically bind to a peptide having the amino acid sequence of SEQ ID NO:5 and/or specifically binds to mIgE comprises a variable heavy chain ($V_H$) domain of SEQ ID NO:10. In a particular embodiment, an antibody of the invention that specifically bind to a peptide having the amino acid sequence of SEQ ID NO:5 and/or specifically binds to mIgE comprises a $V_H$ domain encoded by the nucleotide of SEQ ID NO: 8. In a specific embodiment, an antibody of the invention that specifically bind to a peptide having the amino acid sequence of SEQ ID NO:5 and/or specifically binds to mIgE comprises a $V_L$ domain of SEQ ID NO:9 and $V_H$ domain of SEQ ID NO:10. In a particular embodiment, an antibody of the invention that specifically bind to a peptide having the amino acid sequence of SEQ ID NO:5 and/or specifically binds to mIgE comprises a $V_L$ domain encoded by the nucleotide of SEQ ID NO: 7 and a $V_H$ domain encoded by the nucleotide of SEQ ID NO: 8.

In one embodiment an antibody of the invention that specifically bind to a peptide having the amino acid sequence of SEQ ID NO:5 and/or specifically binds to mIgE comprises a variable light chain ($V_L$) domain of SEQ ID NO:60. In a particular embodiment, an antibody of the invention that specifically bind to a peptide having the amino acid sequence of SEQ ID NO:5 and/or specifically binds to mIgE comprises a $V_L$ domain encoded by the nucleotide of SEQ ID NO: 62. In another embodiment, an antibody of the invention that specifically bind to a peptide having the amino acid sequence of SEQ ID NO:5 and/or specifically binds to mIgE comprises a variable heavy chain ($V_H$) domain of SEQ ID NO:63. In a particular embodiment, an antibody of the invention that specifically bind to a peptide having the amino acid sequence of SEQ ID NO:5 and/or specifically binds to mIgE comprises a $V_H$ domain encoded by the nucleotide of SEQ ID NO: 61. In a specific embodiment, an antibody of the invention that specifically bind to a peptide having the amino acid sequence of SEQ ID NO:5 and/or specifically binds to mIgE comprises a $V_L$ domain of SEQ ID NO:62 and $V_H$ domain of SEQ ID NO:63. In a particular embodiment, an antibody of the invention that specifically bind to a peptide having the amino acid sequence of SEQ ID NO:5 and/or specifically binds to mIgE comprises a $V_L$ domain encoded by the nucleotide of SEQ ID NO: 60 and a $V_H$ domain encoded by the nucleotide of SEQ ID NO: 61.

The present invention comprises antibodies that specifically binds to membrane-anchored IgE (mIgE). In one embodiment an antibody of the invention that specifically bind to that specifically binds to membrane-anchored IgE (mIgE) comprises a variable heavy chain ($V_H$) domain of SEQ ID NO:81. In a particular embodiment, an antibody of the invention that specifically bind to a peptide having the amino acid sequence of SEQ ID NO:5 comprises a $V_H$ domain encoded by the nucleotide of SEQ ID NO: 80.

In other embodiments, an antibody of the invention that specifically bind to a peptide having the amino acid sequence of SEQ ID NO:5 and/or specifically binds to mIgE comprises at least one, at least 2, at least 3, at least 4, at least 5, or at least 6 CDRs from the antibody D5 or F4. In still other embodiments, an antibody of the invention that specifically binds to mIgE comprises at least one, at least 2, at least 3 CDRs from the antibody D9. The amino acid sequence of the CDRs of antibody D5 are indicated in FIG. 12 and are represented by SEQ ID NOS: 11 ($V_L$ CDR1), 12 ($V_L$ CDR2), 13 ($V_L$ CDR3), 14 ($V_H$ CDR1), ($V_H$ CDR2), and 16 ($V_H$ CDR3). The amino acid sequence of the CDRs of antibody F4 are indicated in FIG. 15 and are represented by SEQ ID NOS: 74 ($V_L$ CDR1), 75 ($V_L$ CDR2), 76 ($V_L$ CDR3), 77 ($V_H$ CDR1), 78 ($V_H$ CDR2), and 79 ($V_H$ CDR3). The amino acid sequence of the CDRs of antibody D9 are indicated in FIG. 16 and are represented by SEQ ID NOS: 82 ($V_H$ CDR1), 83 ($V_H$ CDR2), and 84 ($V_H$ CDR3).

The present invention also encompasses antibodies that specifically bind to a peptide having the amino acid sequence of SEQ ID NO:5 and/or specifically binds to mIgE comprising at least one CDR selected from the group comprising: a CDR that is at least 80% identical to the light chain CDR1 of the D5 antibody, a CDR that is at least 80% identical to the light chain CDR2 of the D5 antibody, a CDR that is at least 80% identical to the light chain CDR3 of the D5 antibody, a CDR that is at least 80% identical to the heavy chain CDR1 of the D5 antibody, a CDR that is at least 80% identical to the heavy chain CDR2 of the D5 antibody, a CDR that is at least 80% identical to the heavy chain CDR3 of the D5 antibody, a CDR that is at least 80% identical to the light chain CDR1 of the F4 antibody, a CDR that is at least 80% identical to the light chain CDR2 of the F4 antibody, a CDR that is at least 80% identical to the light chain CDR3 of the F4 antibody, a CDR that is at least 80% identical to the heavy chain CDR1 of the F4 antibody, a CDR that is at least 80% identical to the heavy chain CDR2 of the F4 antibody, a CDR that is at least 80% identical to the heavy chain CDR3 of the F4 antibody, a CDR that is at least 80% identical to the heavy chain CDR1 of the D9 antibody, a CDR that is at least 80% identical to the heavy chain CDR2 of the D9 antibody, and a CDR that is at least 80% identical to the heavy chain CDR3 of the D9 antibody. Also contemplated are antibodies that specifically bind to a peptide having the amino acid sequence of SEQ ID NO:5 and/or specifically binds to mIgE having at least one CDR that is at least 80%, or at least 85%, or at least 90%, or at least 95%, or at least 98%, or at least 99% identical to a CDR present in an antibody selected from the group consisting of D5, F4 and D9.

The present invention further encompasses nucleotides encoding antibodies of the invention. In one embodiment, an isolated nucleic acid sequence of the invention encodes the amino acid sequence of SEQ ID NO:9 or 10. In a specific embodiment, an isolated nucleic acid sequence of the invention comprises SEQ ID NO: 7 or 8. In another embodiment, an isolated nucleic acid sequence of the invention encodes the amino acid sequence of SEQ ID NO:72 or 73. In a specific embodiment, an isolated nucleic acid sequence of the invention comprises SEQ ID NO: 70 or 71. In still another embodiment, an isolated nucleic acid sequence of the invention encodes the amino acid sequence of SEQ ID NO:81. In a specific embodiment, an isolated nucleic acid sequence of the invention comprises SEQ ID NO: 80. Also encompassed by the present invention are cell comprising at least a nucleic acid sequence of the invention encoding the amino acid sequence of SEQ ID NO:9, 10, 72, 73 or 81.

In another embodiment, an isolated nucleic acid sequence of the invention encodes a polypeptide that is at least 60% identical, or at least 70% identical, or at least 80% identical, or at least 85% identical, or at least 90% identical, or at least 95% identical, or at least at least 97% identical, or at least 99% identical, or 100% identical to the amino acid sequence of SEQ ID NO:9, 10, 72, 73 or 81. In still another embodiment, an isolated nucleic acid sequence of the invention is at least 60% identical, or at least 70% identical, or at least 80% identical, or at least 85% identical, or at least 90% identical, or at least 95% identical, or at least at least 97% identical, or at least 99% identical, or 100% identical to the nucleic acid sequence of SEQ ID NO:7, 8, 70, 71 or 80.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877 (1993). Such an algorithm is incorporated into the BLASTN and BLASTX programs (version 2.2) as described in Schaffer et al., Nucleic Acids Res., 29:2994-3005 (2001). When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10: 3-5 (1994); and FASTA described in Pearson and Lipman, Proc. Natl. Acad. Sci USA, 85: 2444-8 (1988).

In another embodiment, the percent identity between two amino acid sequences can be accomplished using the GAP program in the GCG software package (available at http://www.accelrys.com, as available on Aug. 31, 2001) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (available at http://www.cgc.com), using a gap weight of 50 and a length weight of 3.

It is contemplated that the present invention also encompasses antibodies that bind the same epitope as an antibody comprising the variable regions of D5 (encoded by SEQ ID NO: 7 and 8). Also encompassed are antibodies that compete for binding of the epitope of an antibody comprising the variable regions of D5 (encoded by SEQ ID NO: 7 and 8). The present invention further encompasses antibodies that bind the same epitope as an antibody comprising the variable regions of D5 (encoded by SEQ ID NO: 7 and 8) that have a $K_d$ between about $10^{-7}$M and about $10^{-8}$M, between about $10^{-8}$M and about $10^{-9}$M, between about $10^{-9}$M and about $10^{-10}$M, between about $10^{-10}$M and about $10^{-11}$M, between about $10^{-11}$M and about $10^{-12}$M, between about $10^{-12}$M and about $10^{-13}$M, between about $10^{-13}$M and about $10^{-14}$M.

As disclosed herein (see, e.g., Example 3) the antibodies of the invention can mediate ADCC against target cells expressing mIg, in particular mIgE. Thus, the cεmx.migis antibodies disclosed herein are useful for the treatment of IgE-mediated disorders, including but not limited to, those resulting from or associated with the binding of IgE to FcεRI and those caused by monoclonal expansion of IgE expressing B-cells. An IgE mediated or associated disease or disorder includes, for example, allergic disease caused by IgE antibodies and mast cell mediators including but not limited to atopic diseases such as allergic rhinitis, allergic asthma, including asthma associated with specific antigenic factors such as seasonal pollens (grass: rye, timothy, ragweed) and tree (birch), perennial allergens such as dust mite, animal danders, feathers and fungal spores and occupational antigens such as detergents and metals as well as asthma associated with non-antigen specific factors such as infection, irritants such as smoke, fumes, diesel exhaust particles and sulphur dioxide, asthma associated with airway cooling (exercise, cold air temperatures) and emotional stress; atopic dermatitis and allergic gastroenteropathy as well as anaphylactic diseases including systemic anaphylaxis and reactions to proteins in foods (e.g., peanuts), venom, vaccines, hormones, antiserum, enzymes and latex, reactions to haptens including antibiotics, muscle relaxants, vitamins, cytotoxins and opiates and reactions to polysaccharides such as dextran, iron dextran and polygeline and other anaphylactic diseases or disorders such as urticaria-angioedema, as well as B-cell expansion diseases such as Job's disease, post transplant lymphoproliferative disorder (PTLD), and monocolonal gammopath of unknown significance (MGUS). In addition, the antibodies of the invention are useful for the treatment of IgE-mediated gastro-intestinal inflammatory disorders which can be broadly defined as intractable chronic responses to a broad range of host reaction to a variety of insults, such as those caused by injury or infection which are characterized by, or results from pathology affected by IgE. Particular disorders included within the scope of the term includes inflammatory bowel disease (e.g., Crohn's disease, ulcerative colitis, indeterminate colitis and infectious colitis), gastroenteropathy, enteritis, mucositis (e.g., oral mucositis, gastrointestinal mucositis, nasal mucositis and proctitis), necrotizing enterocolitis and esophagitis).

Accordingly, the present invention provides methods useful for the prevention, management, treatment or amelioration of B-cell mediated diseases and disorders including, those resulting from or associated with monoclonal expansion of B-cells, and in particular those mediated by IgE. In one embodiment, the invention provides methods of treating an IgE-mediated disease in a human comprising administering to an individual in need of such prevention, amelioration, or treatment an effective amount of an antibody of the invention.

In a specific embodiment, the invention provides methods of treating an IgE-mediated disease in a human comprising administering to an individual in need of such prevention, amelioration, or treatment an effective amount of antibody of the invention that specifically binds to a peptide comprising an amino acid sequence selected from the group consisting of SEQ ID NO:5, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46.

In another specific embodiment, the invention provides methods of treating an IgE-mediated disease in a human comprising administering to an individual in need of such prevention, amelioration, or treatment an effective amount of antibody of the invention in combination with other prophylactic or therapeutic agents.

As described above, the migis peptides, which are present only on membrane-anchored immunoglobulins, are unique for the different immunoglobulin isotypes. Therefore, this extracellular segment of the immunoglobulin membrane anchoring peptide forms, in whole or in part, an epitope unique to the B cells expressing a particular membrane-anchored immunoglobulin isotype. Thus, therapeutics, such as antibodies, which specifically target the migis peptides would be useful to target specific classes of B-cells for the treatment of a wide variety of conditions including allergic diseases and those mediated by monoclonal B-cell expansion.

However, as disclosed herein, when identifying antibodies which are both specific for a particular migis peptide and which bind membrane-anchored immunoglobulin, one must account for the presence of predominant epitopes within the migis peptides which may have undesirable characteristics. For example, as demonstrated herein, a predominant migis epitope may be shared with other proteins or may be hidden on the membrane-anchored immunoglobulin. Accordingly, the present invention also provides methods for identification, isolation and use of antibodies which do not bind to predominant epitopes present on any polypeptide of interest (e.g., migis peptides, and peptides comprising migis peptides and fragments thereof).

The present invention encompasses a method of producing an antibody that does not bind to a predominant epitope comprising: (a) screening an antibody library before or after selection for antibodies which bind to a polypeptide comprising a predominant epitope for antibodies which are not inhibited by an antibody recognizing the predominant epitope present on said polypeptide; and (b) isolating at least one antibody from (a). It is contemplated that a predominant epitope is one which is accessible, antigenic and furthermore is an epitope to which antibodies are readily generated, identified, or isolated. A single polypeptide may comprise more than one predominant epitope. A predominant epitope may be a linear polypeptide sequence or may result from the three dimensional confirmation of a polypeptide. It is further contemplated that a predominant epitope is one which will be recognized by multiple antibody binding domains present in an antibody library. Antibodies recognizing a predominant epitope may be antibodies previously isolated from the same library as that used in the methods of the present invention. An antibody may be considered to bind a predominant epitope if, for example, it competes for binding with other antibodies which bind the same polypeptide. In one embodiment, a method of producing an antibody that does not bind to a predominant epitope of a polypeptide comprising a migis peptide (or fragment thereof) is provided herein. For example, a method of producing such antibodies to a mIgE peptide is provided herein.

In one embodiment, the method of producing an antibody that does not bind to a predominant epitope comprises: (a) isolating from an antibody library those clones which bind to a polypeptide comprising the predominant epitope; (b) screening the clones isolated in (a) for those which are not inhibited by an antibody that specifically binds the predominant epitope; and (c) isolating at least one antibody from (b). In one embodiment, a method of producing an antibody that does not bind to a predominant epitope of a polypeptide comprising a migis peptide (or fragment thereof) is provided herein. For example, a method of producing such antibodies to a mIgE peptide is provided herein.

Methods for generating and isolating clones from antibody libraries are well known in the art. Some representative methods are disclosed in Section 5.3 entitled "Methods of Generating Antibodies" and in Section 6.1, Example 1. Methods to screen antibodies for those which do or don't inhibit the binding of another antibody are well known in the art. Several representative methods are disclosed in section 5.5 entitled "Biological Assays" and in Section 6.1, Example 1. The antibody clones identified by the method of the invention may be readily isolated by methods well known in the art. It is contemplated that antibody clones could be isolated from an antibody library in the presence of one or more antibodies which bind predominant epitopes present on the polypeptide comprising the predominant epitope thereby isolating only those antibody clones which are not inhibited by one or more antibodies which bind predominant epitopes. The use of antibodies which bind predominant epitopes during the isolation of antibody clones from an antibody library may reduce the number of clones to be screened for additional desired binding properties (e.g., specificity for mIg).

The methods of the invention may also be useful for the production of antibodies that specifically bind a migis epitope which is not a predominant epitope, is not shared by other proteins and which is not hidden on a membrane-anchored immunoglobulin. In one embodiment, the method for producing antibodies that specifically bind a migis epitope which is not a predominant epitope, is not shared by other proteins and which is not hidden on a membrane-anchored immunoglobulin comprises: (a) isolating from an antibody library those clones which bind to a polypeptide comprising the migis epitope; (b) screening the clones isolated from step (a) for those which are not inhibited by an antibody recognizing the predominant epitope present on said polypeptide comprising the migis epitope; (c) screening the clones which are not inhibited in step (b) for those which specifically bind cells having the membrane anchored immunoglobulin; (d) screening the clones which specifically bound in step (c) for those which do not bind cells not having the membrane anchored immunoglobulin; and (e) isolating at least one antibody from (d).

Accordingly, the methods of the present invention are useful for the production of antibodies which specifically bind membrane-anchored immunoglobulins (referred to herein jointly as "mIgs", and individually as "mIgG", "mIgA", "mIgE", "mIgM" and "mIgD"), do not bind predominant epitopes and do not bind other proteins. In a specific embodiment, the epitope recognized by antibodies which specifically bind mIgs is a migis epitope. Exemplary migis epitopes include, but are not limited to, those shown in FIG. 1A and those described herein as SEQ ID NOS.: 1, 2, 5, 47, 48 and 49. Other exemplary migis epitopes include amino acid residues comprising a migis peptide and one or more amino acid residues of the adjacent heavy chain sequences (e.g., SEQ ID NO:5 and 17 to 49).

In one embodiment, antibodies produced by the methods of the invention specifically bind mIgs. In a specific embodiment, antibodies produced by the methods of the invention are human antibodies. In still another specific embodiment, antibodies produced by the methods of the invention mediate ADCC and/or CDC activity. In yet another specific embodiment, antibodies produced by the methods of the invention are useful for the treatment of B-cell mediated diseases including but not limited to asthma, allergic diseases (e.g., by targeting B-cell expressing mIgE), myelomas, autoimmune and inflammatory diseases such as rheumatoid arthritis, and lupus (e.g., by targeting B-cells expressing mIgG or mIgA), and diseases caused by monoclonal expansion of B-cells such as, Job's disease (e.g., by targeting B-cell expressing mIgE), Waldenstrom macroglubulinemia (e.g., by targeting B-cell expressing mIgM), post transplant lymphoproliferative disorder (PTLD), and monocolonal gammopath of unknown significance (MGUS).

In one specific embodiment, antibodies produced by the methods of the invention specifically bind a migis epitope present on the α-chain. In another specific embodiment, antibodies produced by the methods of the invention specifically bind a migis epitope present on the δ-chain. In still another specific embodiment, antibodies produced by the methods of the invention specifically bind a migis epitope present on the γ-chain. In yet another specific embodiment, antibodies produced by the methods of the invention specifically bind a migis epitope present on the μ-chain. In still another specific embodiment, antibodies produced by the methods of the invention specifically bind a migis epitope present on the ε-chain.

In one embodiment, antibodies produced by the methods of the invention specifically bind to membrane anchored immunoglobulins (mIgs). In another embodiment, antibodies produced by the methods of the invention specifically bind to mIgA but do not bind mIgs other than mIgA. In still another embodiment, antibodies produced by the methods of the invention specifically bind to mIgD but do not bind mIgs other than mIgD. In still another embodiment, antibodies produced by the methods of the invention specifically bind to mIgG but do not bind mIgs other than mIgG. In yet another embodiment, antibodies produced by the methods of the invention specifically bind to mIgM but do not bind mIgs other than mIgM. In still another embodiment, antibodies produced by the methods of the invention specifically bind to mIgE but do not bind mIgs other than mIgE.

In one embodiment, an antibody produced by the methods of the invention which specifically binds a migis epitope depletes B cells or plasma cells expressing mIg. Depletion may occur in an in vitro assay designed to measure B cell or plasma cell depletion, or may occur in vivo in a subject. In a specific embodiment, an antibody produced by the methods of the invention which specifically binds a migis epitope depletes B cells or plasma cells expressing mIg through ADCC. In another specific embodiment, an antibody produced by the methods of the invention which specifically binds a migis epitope depletes B cells or plasma cells expressing mIg through CDC.

In one embodiment, an antibody produced by the methods of the invention which specifically binds a migis epitope depletes B cells or plasma cells expressing mIgA. In a specific embodiment, an antibody produced by the methods of the invention which specifically binds a migis epitope depletes B cells or plasma cells expressing mIgD. In another specific embodiment, an antibody produced by the methods of the invention which specifically binds a migis epitope depletes B cells or plasma cells expressing mIgG. In yet another specific embodiment, an antibody produced by the methods of the invention which specifically binds a migis epitope depletes B cells or plasma cells expressing mIgM.

5.1 Antibodies of the Invention

As used herein, the terms "antibody" and "antibodies" refer to monoclonal antibodies, multispecific antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" specifically include the cεmx.migis antibodies described herein, full length antibodies and Fc variants thereof comprising Fc regions, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH) -Fc fusions, scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Antibodies of the invention may include, but are not limited to, synthetic antibodies, monoclonal antibodies, oligoclonal antibodies, recombinantly produced antibodies, intrabodies, multispecific antibodies, bispecific antibodies, human antibodies, humanized antibodies, chimeric antibodies, synthetic antibodies, single-chain Fv-Fc fusions (scFv-Fc), single-chain Fv (scFv), and anti-idiotypic (anti-Id) antibodies. In particular, antibodies used in the methods of the present invention include immunoglobulin molecules and immunologically active portions of immunoglobulin molecules. The antibodies of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

Antibodies of the invention may be from any animal origin including birds and mammals (e.g., human, rodent, donkey, sheep, rabbit, goat, guinea pig, camel, horse, or chicken). In one embodiment, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

Antibodies like all polypeptides have an Isoelectric Point (pI), which is generally defined as the pH at which a polypeptide carries no net charge. It is known in the art that protein solubility is typically lowest when the pH of the solution is equal to the isoelectric point (pI) of the protein. It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. The pI of a protein may be determined by a variety of methods including but not limited to, isoelectric focusing and various computer algorithms (see for example Bjellqvist et al., 1993, *Electrophoresis* 14:1023-1031). In one embodiment, the pI of the antibodies of the invention is higher than about 6.5, about 7.0, about 7.5, about 8.0, about 8.5, or about 9.0. In one embodiment, substitutions resulting in alterations in the pI of the antibody of the invention will not significantly diminish its binding affinity for a migis epitope. In another embodiment, the pI of the antibodies of the invention is higher then 6.5, 7.0, 7.5, 8.0, 8.5, or 9.0. It is specifically contemplated that the substitution(s) of the Fc region that result in altered binding to FcγR (described supra) may also result in a change in the pI. In another embodiment, substitution(s) of the Fc region are specifically chosen to effect both the desired alteration in FcγR binding and any desired change in pI. As used herein the pI value is defined as the pI of the predominant charge form. The pI of a protein may be determined by a variety of methods including but not limited to, isoelectric focusing and various computer algorithms (see, e.g., Bjellqvist et al., 1993, *Electrophoresis* 14:1023).

The thermal melting temperatures (Tm) of the Fab domain of an antibody, can be a good indicator of the thermal stability of an antibody and may further provide an indication of the shelf-life. A lower Tm indicates more aggregation/less stability, whereas a higher Tm indicates less aggregation/more stability. Thus, antibodies having higher Tm are preferable. In one embodiment, the Fab domain of an antibody of the invention has a Tm value higher than at least 50° C., 55° C., 60° C., 65° C., 70° C., 75° C., 80° C., 85° C., 90° C., 95° C., 100° C., 105° C., 110° C., 115° C. or 120° C. Tm of a protein domain (e.g., a Fab domain) can be measured using any standard method known in the art, for example, by differential scanning calorimetry (see, e.g., Vermeer et al., 2000, *Biophys. J.* 78:394-404; Vermeer et al., 2000, *Biophys. J.* 79: 2150-2154).

Antibodies of the invention may be monospecific, bispecific, trispecific or have greater multispecificity. Multispecific antibodies may immunospecifically bind to different epitopes of desired target molecule or may immunospecifically bind to both the target molecule as well as a heterologous epitope, such as a heterologous polypeptide or solid support material. See, e.g., International Publication Nos. WO 94/04690; WO 93/17715; WO 92/08802; WO 91/00360; and WO 92/05793; Tutt, et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547-1553). In the present case, one of the binding specificities is for a migis epitope (e.g., cϵmx.migis) and the other one is for any other antigen (e.g., CD3, a signaling or effector molecule).

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a migis epitope and the other arm directed against any other antigen. Methods for making bispecific antibodies are known in the art. Traditional production of full-length bispecific antibodies is based on the coexpression of two immunoglobulin heavy chain-light chain pairs, where the two chains have different specificities (Millstein et al., 1983, *Nature*, 305:537-539). Because of the random assortment of immunoglobulin heavy and light chains, these hybridomas (quadromas) produce a potential mixture of different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, *EMBO J.*, 10:3655-3659. A more directed approach is the generation of a Di-diabody a tetravalent bispecific antibody. Methods for producing a Di-diabody are known in the art (see e.g., Lu et al., 2003, J Immunol Methods 279:219-32; Marvin et al., 2005, Acta Pharmacolical Sinica 26:649).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., a migis epitope such as cϵmx.migis), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, *Methods in Enzymology*, 121:210. According to another approach described in WO96/27011, a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089) Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies incorporating at least one hinge modification of the invention are contemplated. For example, trispecific antibodies can be prepared. See, e.g., Tutt et al. J. Immunol. 147: 60 (1991).

The antibodies of the invention encompass single domain antibodies, including camelized single domain antibodies (see e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231: 25; International Publication Nos. WO 94/04678 and WO 94/25591; U.S. Pat. No. 6,005,079.

Other antibodies specifically contemplated are "oligoclonal" antibodies. As used herein, the term "oligoclonal" antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consist of a predetermined mixture of antibodies against one or more epitopes are generated in a single cell. In another embodiment, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule (e.g., mIgE, mIgG, mIgA, mIgD, mIgM). Those skilled in the art will know or can determine what type of antibody or mixture of antibodies is applicable for an intended purpose and desired need.

Antibodies of the present invention also encompass antibodies that have half-lives (e.g., serum half-lives) in a mammal, (e.g., a human), of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311).

In one embodiment, the antibodies of the invention may be chemically modified (e.g., one or more chemical moieties can be attached to the antibody) or be modified to alter its glycosylation, again to alter one or more functional properties of the antibody.

In still another embodiment, the glycosylation of the antibodies of the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861.

Additionally or alternatively, an antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176, 195; PCT Publications WO 03/035835; WO 99/54342.

In still another embodiment, the glycosylation of an antibody of the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714, 350 and 6,350,861.

Additionally or alternatively, an antibody of the invention can be made that has an altered type of glycosylation, such as a hypofucosylated antibody of the invention having reduced amounts of fucosyl residues or an antibody of the invention having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277: 26733-26740; Umana et al. (1999) *Nat. Biotech.* 17:176-1, as well as, European Patent No: EP 1,176,195; PCT Publications WO 03/035835; WO 99/54342.

5.2 Antibody Conjugates And Derivatives

Antibodies of the invention include derivatives that are modified (i.e., by the covalent attachment of any type of molecule to the antibody such that covalent attachment). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413, 622. The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses the use of antibodies or fragments thereof recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

The present invention further includes formulations comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins, e.g., of anti-migis antibodies, may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to a migis epitope may be recombined with one or more components, motifs, sections, parts, domains, fragments, etc. of one or more heterologous molecules.

Moreover, the antibodies or fragments thereof can be fused to marker sequences, such as a peptide to facilitate purification. In specific embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, antibodies of the invention or analogs or derivatives thereof are conjugated to a diagnostic or detectable agent. Such antibodies can be useful for monitoring or prognosing the development or progression of a cancer as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I) carbon ($^{14}$C), sulfur ($^{35}$S), tritium ($^3$H), indium ($^{115}$In, $^{111}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes.

The present invention further encompasses uses of antibodies of the invention or fragments thereof conjugated to a therapeutic agent.

In other embodiments, antibodies of the invention may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), and auristatin E compounds (e.g. monomethyl auristatin E; see for example U.S. Pat. No. 6,884,869). A more extensive list of therapeutic moieties can be found in PCT publications WO 03/075957;

In other embodiments, antibodies of the invention may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, *J. Immunol.*, 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

In other embodiments, antibodies of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA)

which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage (see generally Garnett, 2002, *Adv Drug Deliv Rev* 53:171-216). Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, *Immunol. Rev.* 62:119-58.

Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, *PNAS USA* 88:10535-10539; Zheng et al., 1995, *J Immunol* 154: 5590-5600; and Vil et al., 1992, *PNAS USA* 89:11337-11341. The fusion of an antibody to a moiety does not necessarily need to be direct, but may occur through linker sequences. Such linker molecules are commonly known in the art and described in Denardo et al., 1998, *Clin Cancer Res* 4:2483-90; Peterson et al., 1999, *Bioconjug Chem* 10:553; Zimmerman et al., 1999, *Nucl Med Biol* 26:943-50; Garnett, 2002, *Adv Drug Deliv Rev* 53:171-216.

Alternatively, an antibody can be conjugated to a second antibody to form an antibody heteroconjugate as described by Segal in U.S. Pat. No. 4,676,980.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The therapeutic moiety or drug conjugated to an antibody or fragment thereof that specifically binds to a migis epitope should be chosen to achieve the desired prophylactic or therapeutic effect(s) for a particular disorder in a subject. A clinician or other medical personnel should consider the following when deciding on which therapeutic moiety or drug to conjugate to an antibody or fragment thereof that specifically binds to a migis epitope: the nature of the disease, the severity of the disease, and the condition of the subject.

5.3 Methods of Generating Antibodies

The antibodies of the invention can be produced by any method known in the art for the synthesis of antibodies, in particular, by chemical synthesis or by recombinant expression techniques.

Polyclonal antibodies to a migis epitope (e.g., cεmx.migis) can be produced by various procedures well known in the art. For example, a migis epitope (e.g., cεmx.migis) or immunogenic fragments thereof can be administered to various host animals including, but not limited to, rabbits, mice, rats, etc. to induce the production of sera containing polyclonal antibodies specific for migis epitope (e.g., cεmx.migis). Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with migis epitope (e.g., cεmx.migis) or a fragment thereof and once an immune response is detected, e.g., antibodies specific for migis epitope are detected in the mouse serum, the mouse spleen is harvested and splenocytes isolated. The splenocytes are then fused by well known techniques to any suitable myeloma cells, for example cells from cell line SP20 available from the ATCC. Additionally, a RIMMS (repetitive immunization, multiple sites) technique can be used to immunize an animal (Kilpatrick et al., 1997, *Hybridoma* 16:381-9). Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody wherein, preferably, the hybridoma is generated by fusing splenocytes isolated from a mouse immunized with migis epitope (e.g., cεmx.migis) or immunogenic fragments thereof, with myeloma cells and then screening the hybridomas resulting from the fusion for hybridoma clones that secrete an antibody able to bind a migis epitiope, and more specifically, a migis epitope in the context of a membrane-anchored immunoglobulin molecule, The antibodies of the invention contain novel amino acid residues in their Fc regions. antibodies can be generated by numerous methods well known to one skilled in the art. Non-limiting examples include, isolating antibody coding regions (e.g., from hybridoma) and making one or more desired substitutions in the Fc region of the isolated antibody coding region. Alternatively, the variable regions may be subcloned into a vector encoding an Fc region comprising one or more high effector function amino acid residues. Additional methods and details are provided below.

Antibody fragments that recognize specific migis epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In one embodiment, antibodies that specifically bind a migis epitope may be generated by phage display methods.

In phage display methods, functional antibody domains are displayed on the surface of phage particles that carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to the migis epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108

In a specific embodiment, an antibody specifically binding a migis epitope is produced by screening a library for antibodies that bind SEQ ID NO:5 and bind with at least 2, at least 5, at least 10-fold less affinity to SEQ ID NO:1 and SEQ ID NO:6. In another specific embodiment, an antibody specifically binding a migis epitope is produced by screening a library for antibodies that that bind SEQ ID NO:5 and wherein the binding to SEQ ID NO:5 is not inhibited by an antibodies comprising the variable regions of A1c (encoded by SEQ ID NOS: 50 and 51) and B1 (encoded by SEQ ID NOS: 60 and 61).

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6): 864-869; Sawai et al., 1995, AJRI 34:26-34; and Better et al., 1988, Science 240:1041-1043.

To generate whole antibodies, PCR primers including a portion of the VH or VL nucleotide sequences, a restriction site, and a flanking sequence to facilitate digestion of the restriction site can be used to amplify the VH or VL sequences in scFv clones. Utilizing cloning techniques known to those of skill in the art, the PCR amplified VH domains can be cloned into vectors expressing a VH constant region, e.g., the human gamma constant, and the PCR amplified VL domains can be cloned into vectors expressing a VL constant region, e.g., human kappa or lamba constant regions. In one embodiment, the constant region is an Fc region containing at least one high effector function amino acid. In a specific embodiment, the vectors for expressing the VH or VL domains comprise a promoter, a secretion signal, a cloning site for both the variable and constant domains, as well as a selection marker such as neomycin. The VH and VL domains may also be cloned into one vector expressing the desired constant regions. The heavy chain conversion vectors and light chain conversion vectors are then co-transfected into cell lines to generate stable or transient cell lines that express full-length antibodies, e.g., IgG, using techniques known to those of skill in the art.

In one embodiment, the antibodies of the invention are chimeric antibodies. A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415.

For some uses, including in vivo use of antibodies in humans and in vitro detection assays, it may be preferable to use human or chimeric antibodies. Completely human antibodies are particularly desirable for most therapeutic treatments of human subjects. Human antibodies can be made by a variety of methods known in the art including phage display methods described above using antibody libraries derived from human immunoglobulin sequences. See also U.S. Pat. Nos. 4,444,887 and 4,716,111; and PCT Publication Nos. WO 98/46645, WO 98/50433, WO 98/24893, WO98/16654, WO 96/34096, WO 96/33735, and WO 91/10741. In one embodiment, the antibodies of the invention are human antibodies.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', $F(ab')_2$, Fabc, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG.sub.1. Where such cytotoxic activity is not desirable, the constant domain may be of the IgG.sub.2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119-25 (2002), Caldas et al., Protein Eng. 13(5): 353-60 (2000), Morea et al., Methods 20(3): 267-79 (2000), Baca et al., J. Biol. Chem. 272(16): 10678-84 (1997), Roguska et al., Protein Eng. 9(10): 895-904 (1996), Couto et al., Cancer Res. 55 (23 Supp): 5973s-5977s (1995), Couto et al., Cancer Res. 55(8): 1717-22 (1995), Sandhu J S, Gene 150(2): 409-10 (1994), and Pedersen et al., J. Mol. Biol. 235(3): 959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323,)

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., migis epitope or immunogenic fragments thereof. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598. In addition, companies such as Abgenix, Inc. (Freemont, Calif.), Genpharm (San Jose, Calif.) and Medarex (Princeton, N.J.) can be engaged to provide human antibodies directed against a selected antigen using technology similar to that described above.

Further, the antibodies of the invention can, in turn, be utilized to generate anti-idiotype antibodies that "mimic" a migis epitope (e.g., cεmx.migis) using techniques well known to those skilled in the art. (See, e.g., Greenspan & Bona, 1989, FASEB J. 7(5): 437-444; and Nissinoff, 1991, J. Immunol. 147(8): 2429-2438). For example, antibodies of the invention which bind to and competitively inhibit the binding of a migis epitope (as determined by assays well known in the art and disclosed infra) to its ligands can be used to generate anti-idiotypes that "mimic" migis binding domains and, as a consequence, bind to and neutralize migis containing proteins and/or its ligands. Such neutralizing anti-idiotypes or Fab fragments of such anti-idiotypes can be used in therapeutic regimens to neutralize migis containing proteins. The invention provides methods employing the use of polynucleotides comprising a nucleotide sequence encoding an antibody of the invention or a fragment thereof.

In one embodiment, the nucleotide sequence encoding an antibody that specifically binds a migis epitope is obtained and used to generate the antibodies of the invention. The nucleotide sequence can be obtained, for example, from sequencing hybridoma clone DNA. If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers that hybridize to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, Or example, the techniques described in *Current Protocols in Molecular Biology*, F. M. Ausubel et al., ed., John Wiley & Sons (Chichester, England, 1998); *Molecular Cloning: A Laboratory Manual,* 3nd Edition, J. Sambrook et al., ed., Cold Spring Harbor Laboratory Press (Cold Spring Harbor, N.Y., 2001); *Antibodies: A Laboratory Manual,* E. Harlow and D. Lane, ed., Cold Spring Harbor Laboratory Press (Cold Spring Harbor, N.Y., 1988); and *Using Antibodies: A Laboratory Manual*, E. Harlow and D. Lane, ed., Cold Spring Harbor Laboratory (Cold Spring Harbor, N.Y., 1999)), to generate antibodies having a different amino acid sequence by, for example, introducing deletions, and/or insertions into desired regions of the antibodies.

In one embodiment, one or more substitutions are made within the Fc region (e.g. supra) of an antibody able to specifically bind a migis epitope. In another embodiment, the amino acid substitutions modify binding to one or more Fc ligand (e.g., FcγRs, C1q) and alter ADCC and/or CDC activity.

In a specific embodiment, one or more of the CDRs is inserted within framework regions using routine recombinant DNA techniques. The framework regions may be naturally occurring or consensus framework regions, specifically contemplated are human framework regions (see, e.g., Chothia et al., 1998, J. Mol. Biol. 278: 457-479 for a listing of human framework regions). In one embodiment, the polynucleotide generated by the combination of the framework regions and CDRs encodes an antibody that specifically binds to a migis epitope (e.g., cϵmx.migis). In another embodiment, as discussed supra, one or more amino acid substitutions may be made within the framework regions, it is contemplated that the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.4 Recombinant Expression of Antibodies

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody of the invention has been obtained, the vector for the production of the antibody or fusion protein molecule may be produced by recombinant DNA technology using techniques well known in the art. Thus, methods for preparing a protein by expressing a polynucleotide containing an antibody or fusion protein encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody of the invention, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody of the invention may be cloned into such a vector for expression of the full length antibody chain (e.g. heavy or light chain).

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In other embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody, are used for the expression of a recombinant antibody. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies that bind to the cϵmx.migis epitope is regulated by a constitutive promoter, inducible promoter or tissue specific promoter.

In bacterial systems, a number of expression vectors may be advantageously selected depending upon the use intended for the antibody being expressed. For example, when a large quantity of such a protein is to be produced, for the generation of pharmaceutical compositions of an antibody, vectors that direct the expression of high levels of fusion protein products that are readily purified may be desirable. Such vectors include, but are not limited to, the *E. coli* expression vector pUR278 (Ruther et al., 1983, EMBO 12:1791), in which the antibody or fusion protein coding sequence may be ligated individually into the vector in frame with the lac Z coding region so that a lac Z-fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of an antibody may be controlled by any promoter or enhancer element known in the art. Promoters which may be used to control the expression of the gene encoding an antibody or fusion protein include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (VIIIa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

Expression vectors containing inserts of a gene encoding an antibody can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide or protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding an antibody in the vector. For example, if the nucleotide sequence encoding the antibody is inserted within the marker gene sequence of the vector, recombinants containing the gene encoding the antibody insert can be identified by the absence of the marker gene function. In the third approach, recombinant expression vectors can be identified by assaying the gene product (e.g., antibody) expressed by the recombinant. Such assays can be based, for example, on the physical or functional properties of the antibody in in vitro assay systems, e.g., binding with anti-bioactive molecule.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines which stably express an antibody may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express an antibody of the invention that specifically binds to the cϵmx.migis epitope. Such engineered cell lines may be particularly useful in screening and evaluation of compounds that affect the activity of an that specifically binds to cϵmx.migis epitope.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell22:817) genes can be employed in tk−, hgprt− or aprt− cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once a peptide, polypeptide, protein, antibody of the invention has been produced by recombinant expression, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of antibodies.

The expression levels of an antibody can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody or fusion protein is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention. For example, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing, a fusion protein or both heavy and light chain polypeptides. The coding sequences for the fusion protein or heavy and light chains may comprise cDNA or genomic DNA.

5.5 Biological Assays

The binding specificity, affinity and functional activity of an antibody of the invention can be characterized in various in vitro binding and cell adhesion assays known in the art, including but limited to, ELISA Western Blot analysis, cell surface staining, inhibition of ligand-receptor interactions, flow cytometric analysis and those disclosed in International Publication Nos. WO 04/014292, WO 03/094859, WO 04/069264, WO 04/028551, WO 03/004057, WO 03/040304, WO 00/78815, WO 02/070007 and WO 03/075957, U.S. Pat. Nos. 5,795,734, 6,248,326 and 6,472,403, Pecheur et al., 2002, FASEB J. 16(10): 1266-1268; Almed et al., The Journal of Histochemistry & Cytochemistry 50:1371-1379 (2002). For example, the binding affinity, specificity and the off-rate of antibody of the invention can be determined by a competitive binding assay, by measuring the inhibitory activity of antibody of the invention on binding to a migis epitope. One example of a competitive binding assay is a radioimmunoassay comprising the incubation of labeled peptide comprising a migis epitope (e.g., 3H or 125I) with the antibody of the invention in the presence of increasing amounts of unlabeled peptide, and the detection of the antibody bound to the labeled peptide. The affinity of an Fc variant for a migis epitope and the binding off-rates can be determined from the data by scatchard plot analysis. Competition with a second antibody can also be determined using radioimmunoassays. In this case, a peptide comprising a migis epitope is incubated with an antibody of the invention conjugated to a labeled compound (e.g., 3H or 125I) in the presence of increasing amounts of a second unlabeled monoclonal antibody.

The kinetic parameters of an antibody of the invention may also be determined using any surface plasmon resonance (SPR) based assays known in the art. For a review of SPR-based technology see Mullet et al., 2000, Methods 22: 77-91;

Dong et al., 2002, Review in *Mol. Biotech.*, 82: 303-23; Fivash et al., 1998, *Current Opinion in Biotechnology* 9: 97-101; Rich et al., 2000, *Current Opinion in Biotechnology* 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention.

The binding specificity of antibody of the invention to a migis peptide can be assessed by any method known in the art including but not limited to, measuring binding to a migis epitope and its crossreactivity to other migis-containing peptides.

The ability of an antibody of the invention to bind to a migis epitope present on a mIg can be determined by methods well known in the art such as flow cytometric analysis and other cell staining techniques including but not limited to immunohistochemistry.

It is contemplated that the protocols and formulations of the invention are tested in vitro, and then in vivo, for the desired therapeutic or prophylactic activity, prior to use in humans. For example, assays which can be used to determine whether administration of a specific therapeutic protocol, formulation or combination therapy of the invention is indicated, include in vitro cell culture assays in which a target cell is grown in culture, and exposed to or otherwise contacted with a formulation of the invention, and the effect of such a formulation upon the tissue sample is observed.

In particular, the ability of any particular antibody to mediate lysis of the target cell by ADCC or CDC can be assayed. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, *J Exp Med* 166:1351-1361; Wilkinson et al., 2001, *J Immunol Methods* 258:183-191; Patel et al., 1995 *J Immunol Methods* 184:29-38 and herein (see Example 3). Alternatively, or additionally, ADCC activity of the antibody of interest may be assessed in vivo, e.g., in a animal model such as that disclosed in Clynes et al., 1998, PNAS USA 95:652-656. To assess the CDC activity of an antibody, a CDC assay, e.g. as described in Gazzano-Santoro et al., 1996, *J. Immunol. Methods,* 202:163, may be performed.

Prophylactic or therapeutic agents can be tested in suitable animal model systems prior to testing in humans, including but not limited to in rats, mice, chicken, cows, monkeys, rabbits, hamsters, etc. For example one of the most relevant animal systems for the study of asthma is the Rhesus Monkey Model. The rhesus monkey model make use of the fact that a small number of rhesus monkeys, which have been infected with the nematode *Ascaris suum*, develop sensitivity to extract of *ascaris*. When these sensitive monkeys are given spray containing *ascaris* antigen, they develop breathing problems resembling asthma. Patterson, R., J. Clini. Invest. 57: 586-593 (1976). The antibodies of this invention can be tested in the asthma/rhesus monkey model system. The *ascaris* sensitive monkeys are given the experimental treatment or control treatment and measurements are made to determine the clinical outcome of treatment. Measurements include quantification of one or more of the following indicators, asthma symptoms upon *ascaris* challenge, the level of circulating IgE, the of circulating IgE-bearing B cells and the IgE density on basophils.

5.6 Prophylactic and Therapeutic Uses

As discussed above, agents that immunospecifically bind a migis epitope can be utilized for the prevention, management, treatment or amelioration of B-cell mediated diseases and disorders including, those resulting from or associated with monoclonal expansion of B-cells, and in particular those mediated by IgE.

Diseases and disorders mediated by IgE include those associated with the binding of IgE to FceRI such as, for example, allergic disease caused by IgE antibodies and mast cell mediators including but not limited to atopic diseases such as allergic rhinitis, allergic asthma, including asthma associated with specific antigenic factors such as seasonal pollens (grass: rye, timothy, ragweed) and tree (birch), perennial allergens such as dust mite, animal danders, feathers and fungal spores and occupational antigens such as detergents and metals as well as asthma associated with non-antigen specific factors such as infection, irritants such as smoke, fumes, diesel exhaust particles and sulphur dioxide, asthma associated with airway cooling (exercise, cold air temperatures) and emotional stress; atopic dermatitis and allergic gastroenteropathy as well as anaphylactic diseases including systemic anaphylaxis and reactions to proteins in foods (e.g., peanut), venom, vaccines, hormones, antiserum, enzymes and latex, reactions to haptens including antibiotics, muscle relaxants, vitamins, cytotoxins and opiates and reactions to polysaccharides such as dextran, iron dextran and polygeline and other anaphylactic diseases or disorders such as urticaria-angioedema.

In addition, certain gastro-intestinal inflammatory disorders are known to be IgE-mediated. Such IgE-mediated gastro-intestinal inflammatory disorders can be broadly defined as intractable chronic response to a to a variety of insults, such as those caused by injury or infection which are characterized by, or results from pathology affected by IgE. Particular disorders included within the scope of IgE-mediated gastro-intestinal inflammatory disorders includes inflammatory bowel disease (e.g., Crohn's disease, ulcerative colitis, indeterminate colitis and infectious colitis), gastroenteropathy, enteritis, mucositis (e.g., oral mucositis, gastrointestinal mucositis, nasal mucositis and proctitis), necrotizing enterocolitis and esophagitis).

Diseases and disorders or associated with B-cell expansion diseases include, for example, hyper IgE syndrome (Job's disease), post transplant lymphoproliferative disorder (PTLD), monocolonal gammopath of unknown significance (MGUS), Waldenstrom Macroglubulinemia, neuropathy, nephropathy, myelomas, inflammatory and autoimmune diseases such as Rheumatoid arthritis and Lupus.

Diseases and disorders which can be prevented, treated or inhibited by administering an effective amount of one or more antibodies of the invention include, but are not limited to, asthma, autoimmune disorders (e.g., lupus, rheumatoid arthritis, multiple sclerosis, myasthenia gravis, Hashimoto's disease, and immunodeficiency syndrome), inflammatory disorders (e.g., asthma, allergic disorders, and rheumatoid arthritis), infectious diseases (e.g., AIDS), and proliferative disorders (e.g., leukemia, carcinoma, and lymphoma). In a specific embodiment, the subject antibodies will be used to treat asthma. In another embodiment, the subject antibodies will be used to treat diseases involving mucin production as a major component of pathology. Such diseases include cystic fibrosis, emphysema and COPD by way of example.

5.7 Formulations and Administration

As described above, the present invention relates to the use of agents that specifically bind a migis epitope for the prevention, management, treatment or amelioration of a B-cell mediated disease or disorder. Accordingly, the present invention provides formulations (e.g., a pharmaceutical composition) comprising one or more antibodies of the invention that specifically bind to a migis epitope (also referred to herein as "formulation(s) of the invention" or simply "formulation(s)"). In specific embodiments, the agent specifically binds a cεmx.migis epitope and inhibits IgE production. Accordingly, it is contemplated that formulation comprising an agent that specifically binds to a cεmx.migis epitope is useful for the prevention, management, treatment or amelioration of an IgE-mediated disease (e.g., allergies) or one or more symptoms thereof.

In one embodiment, formulations (e.g., a pharmaceutical composition) comprising one or more antibodies of the invention are liquid formulations (referred to herein as "liquid formulation(s)" which are specifically encompassed by the more generic terms "formulation(s) of the invention" and "formulation(s)"). In a specific embodiment, the liquid formulations are substantially free of surfactant and/or inorganic salts. In another specific embodiment, the liquid formulations have a pH ranging from about 5.0 to about 7.0, about 5.5 to about 6.5, or about 5.8 to about 6.2, or about 6.0. In another specific embodiment, the liquid formulations have a pH ranging from 5.0 to 7.0, 5.5 to 6.5, or 5.8 to 6.2, or 6.0. In yet another specific embodiment, the liquid formulations comprise histidine at a concentration ranging from about 1 mM to about 100 mM, or from about 5 mM to about 50 mM, or about 10 mM to about 25 mM. In still another specific embodiment, the liquid formulations comprise histidine at a concentration ranging from 1 mM to 100 mM, or from 5 mM to 50 mM, or 10 mM to 25 mM In another embodiment, the liquid formulations have a concentration of one or more antibodies of the invention that is about 50 mg/ml, about 75 mg/ml, about 100 mg/ml, about 125 mg/ml, about 150 mg/ml, about 175 mg/ml, about 200 mg/ml, about 225 mg/ml, about 250 mg/ml, about 275 mg/ml, or about 300 mg/ml. In another embodiment, the liquid formulations have a concentration of one or more antibodies of the invention that is 50 mg/ml, 75 mg/ml, 100 mg/ml, 125 mg/ml, 150 mg/ml, 175 mg/ml, 200 mg/ml, 225 mg/ml, 250 mg/ml, 275 mg/ml, or 300 mg/ml. In still another embodiment, the liquid formulations should exhibit one, or more of the following characteristics, stability, low to undetectable levels of antibody fragmentation and/or aggregation, very little to no loss of the biological activities of the antibodies or antibody fragments during manufacture, preparation, transportation, and storage. In certain embodiments the liquid formulations lose less than 50%, or less than 30%, or less than 20%, or less than 10% or even less than 5% or 1% of the antibody activity within 1 year storage under suitable conditions at about 4° C. The activity of an antibody can be determined by a suitable antigen-binding or effector function assay for the respective antibody. In yet another embodiment, the liquid formulations are of low viscosity and turbidity. In a particular embodiment, the liquid formulations have a viscosity of less than 10.00 cP at any temperature in the range of 1 to 26° C. Viscosity can be determined by numerous method well known in the art. For example, the viscosity of a polypeptide solution can be measured using a ViscoLab 4000 Viscometer System (Cambridge Applied Systems) equipped with a ViscoLab Piston (SN:7497, 0.3055", 1-20 cP) and S6S Reference Standard (Koehler Instrument Company, Inc.) and connected to a water bath to regulate the temperature of the samples being analyzed. The sample is loaded into the chamber at a desired starting temperature (e.g., 2° C.) and the piston lowered into the sample. After sample was equilibrated to the temperature of the chamber, measurement is initiated. The temperature is increased at a desired rate to the desired final temperature (e.g., $\geq 25°$ C.). And the viscosity over time is recorded.

It is contemplated that the liquid formulations may further comprise one or more excipients such as a saccharide, an amino acid (e.g. arginine, lysine, and methionine) and a polyol. Additional descriptions and methods of preparing and analyzed liquid formulations can be found, for example, in PCT publications WO 03/106644; WO 04/066957; WO 04/091658.

In one embodiment the formulations (e.g., liquid formulations) of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with monoclonal antibodies, it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

It will be apparent to one skilled in the art that a formulation comprising one or more antibodies of the invention to be administered to a subject (e.g., a human) in need thereof should be formulated in a pharmaceutically-acceptable excipient. Examples of formulations, pharmaceutical compositions in particular, of the invention include but are not limited to those disclosed in PCT publications WO 02/070007, WO 03/075957 and WO 04/066957. Briefly, the excipient that is included with the antibodies of the invention in these formulations (e.g., liquid formulations) can be selected based on the expected route of administration of the formulations in therapeutic applications. The route of administration of the formulations depends on the condition to be treated. For example, intravenous injection may be preferred for treatment of a systemic disorder such as a lymphatic cancer or a tumor which has metastasized. The dosage of the formulations to be administered can be determined by the skilled artisan without undue experimentation in conjunction with standard dose-response studies. Relevant circumstances to be considered in making those determinations include the condition or conditions to be treated, the choice of formulations to be administered, the age, weight, and response of the individual patient, and the severity of the patient's symptoms. For example, the actual patient body weight may be used to calculate the dose of the antibodies of the invention in these formulations in milliliters (mL) to be administered. There may be no downward adjustment to "ideal" weight. In such a situation, an appropriate dose may be calculated by the following formula:

$$\text{Dose (mL)} = [\text{patient weight (kg)} \times \text{dose level (mg/kg)} / \text{drug concentration (mg/mL)}]$$

Depending on the condition, the formulations can be administered orally, parenterally, intramuscularly, intranasally, vaginally, rectally, lingually, sublingually, buccally, intrabuccally, intravenously, cutaneously, subcutaneously and/or transdermally to the patient.

Accordingly, formulations designed for oral, parenteral, intramuscular, intranasal, vaginal, rectal, lingual, sublingual, buccal, intrabuccal, intravenous, cutaneous, subcutaneous and/or transdermal administration can be made without undue experimentation by means well known in the art, for example, with an inert diluent or with an edible carrier. The formulations may be enclosed in gelatin capsules or compressed into tablets. For the purpose of oral therapeutic administration, the formulations of the present invention may be incorporated with excipients and used in the form of tablets, troches, capsules, elixirs, suspensions, syrups, wafers, chewing gums, and the like.

Tablets, pills, capsules, troches and the like may also contain binders, recipients, disintegrating agent, lubricants, sweetening agents, and/or flavoring agents. Some examples of binders include microcrystalline cellulose, gum tragacanth and gelatin. Examples of excipients include starch and lactose. Some examples of disintegrating agents include alginic acid, cornstarch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various formulations should be pharmaceutically pure and non-toxic in the amounts used.

The formulations of the present invention can be administered parenterally, such as, for example, by intravenous, intramuscular, intrathecal and/or subcutaneous injection. Parenteral administration can be accomplished by incorporating the formulations of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfate, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic. Rectal administration includes administering the formulation into the rectum and/or large intestine. This can be accomplished using suppositories and/or enemas. Suppository formulations can be made by methods known in the art. Transdermal administration includes percutaneous absorption of the formulation through the skin. Transdermal formulations include patches, ointments, creams, gels, salves, and the like. The formulations of the present invention can be administered nasally to a patient. As used herein, nasally administering or nasal administration includes administering the formulations to the mucous membranes of the nasal passage and/or nasal cavity of the patient.

In certain embodiments, the formulations (e.g., liquid formulations) are administered to the mammal by subcutaneous (i.e., beneath the skin) administration. For such purposes, the formulations may be injected using a syringe. However, other devices for administration of the formulations are available such as injection devices (e.g. the Inject-ease_and Genject-_devices), injector pens (such as the GenPen™); auto-injector devices, needleless devices (e.g., MediJector and BioJector); and subcutaneous patch delivery systems.

In another aspect of the invention there is provided a slow release formulations. In a specific embodiment, a slow release formulation comprises a liquid formulation. Slow release formulations may be formulated from a number of agents including, but not limited to, polymeric nano or microparticles and gels (e.g., a hyaluronic acid gel). Besides convenience, slow release formulations offer other advantages for delivery of protein drugs including protecting the protein (e.g., antibody of the invention) over an extended period from degradation or elimination, and the ability to deliver the protein locally to a particular site or body compartment thereby lowering overall systemic exposure.

The present invention, for example, also contemplates injectable depot formulations in which the protein (e.g., antibody of the invention) is embedded in a biodegradable polymeric matrix. Polymers that may be used include, but are not limited to, the homo- and co-polymers of lactic and glycolic acid (PLGA). PLGA degrades by hydrolysis to ultimately give the acid monomers and is chemically unreactive under the conditions used to prepare, for example, microspheres and thus does not modify the protein. After subcutaneous or intramuscular injection, the protein is released by a combination of diffusion and polymer degradation. By using polymers of different composition and molecular weight, the hydrolysis rate can be varied thereby allowing release to last from days to months. In a further aspect the present invention provides a nasal spray formulation. In a specific embodiment, a nasal spray formulation comprises the liquid formulation of the present invention.

The formulations of the invention may be used in accordance with the methods of the invention for the prevention, management, treatment or amelioration of B-cell mediated diseases including but not limited to allergic diseases, myelomas, diseases caused by monoclonal expansion of B-cells, autoimmune and inflammatory diseases (in particular a IgE-mediated disease) or one or more symptoms thereof. In one embodiment, the formulations of the invention are sterile and in suitable form for a particular method of administration to a subject with a B-cell mediated diseases including but not limited to allergic diseases, myelomas, diseases caused by monoclonal expansion of B-cells, autoimmune and inflammatory diseases (in particular a IgE-mediated disease).

The formulations of the invention may comprise other active ingredients including, but are not limited to, one or more of inhaled asthma medication, such as but not limited to an asthma related therapeutic, a TNF antagonist, an antirheumatic, a muscle relaxant, a narcotic, an analgesic, an anesthetic, a sedative, a local anethetic, a neuromuscular blocker, an antimicrobial, an antpsoriatic, a corticosteriod, an anabolic steroid, an asthma related agent, a mineral, a nutritional, a thyroid agent, a vitamin, a calcium related hormone, an antidiarrheal, an antitussive, an antiemetic, an antiulcer, a laxative, an anticoagulant, an erythropieitin, a filgrastim, a sargramostim, an immunization, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha, a cytokine, or a cytokine antagonist.

In particular, asthma-related compositions of the invention can optionally further comprise at least one selected from an asthma-related therapeutic, a TNF antagonist (e.g., but not limited to a TNF Ig derived protein or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, an asthma related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, inhaled glucocorticosteroids, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable amounts and dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000).

The invention provides methods for preventing, managing, treating or ameliorating B-cell mediated diseases including but not limited to allergic diseases, myelomas, diseases caused by monoclonal expansion of B-cells, autoimmune and inflammatory diseases (in particular a IgE-mediated disease) or one or more symptoms thereof, said method comprising: (a) administering to a subject in need thereof a dose of a prophylactically or therapeutically effective amount of a formulation comprising one or more antibodies of the invention, that specifically bind to a migis epitope and (b) administering one or more subsequent doses of said formulation, to maintain a plasma concentration of the antibody of the invention at a desirable level (e.g., about 0.1 to about 100 µg/ml). In a specific embodiment, the plasma concentration of the antibody of the invention is maintained at 10 µg/ml, 15 µg/ml, 20 µg/ml, 25 µg/ml, 30 µg/ml, 35 µg/ml, 40 µg/ml, 45 µg/ml or 50 µg/ml. In a specific embodiment, said effective amount of the antibody of the invention to be administered is between at least 1 mg/kg and 100 mg/kg per dose. In another specific embodiment, said effective amount of the antibody of the invention to be administered is between at least 1 mg/kg and 20 mg/kg per dose. In another specific embodiment, said effective amount of the antibody of the invention to be administered is between at least 4 mg/kg and 10 mg/kg per dose. In yet another specific embodiment, said effective amount of the antibody of the invention to be administered is between 50 mg and 250 mg per dose. In still another specific embodiment, said effective amount of the antibody of the invention to be administered is between 100 mg and 200 mg per dose.

The present invention provides kits comprising one or more antibodies of the invention that specifically bind to a migis epitope conjugated or fused to a detectable agent, therapeutic agent or drug, in one or more containers, for use in the prevention, treatment, management, amelioration, detection, monitoring or diagnosis of B-cell mediated diseases including but not limited to allergic diseases, myelomas, diseases caused by monoclonal expansion of B-cells, autoimmune and inflammatory diseases, in particular a IgE-mediated disease or disorder. "IgE-mediated disorder" and "IgE mediated disease" means a condition or disease which is characterized by the overproduction and/or hypersensitivity to the immunoglobulin IgE. Specifically, IgE-mediated disorders include conditions associated with anaphylactic hypersensitivity and atopic allergies, including for example: asthma, allergic rhinitis and conjunctivitis (hay fever), eczema, urticaria and food allergies.

The invention also provides kits comprising one or more antibodies of the invention that specifically binds to a migis peptide in a first vial and one or more prophylactic or therapeutic agents, other than an antibody of the invention, in a second vial for use in the prevention, treatment, management, amelioration, detection, monitoring or diagnosis of B-cell mediated diseases including but not limited to allergic diseases, myelomas, diseases caused by monoclonal expansion of B-cells, autoimmune and inflammatory diseases, in particular a IgE-mediated disease. The invention also provides kits comprising one or more antibody of the invention that specifically binds to a migis peptide conjugated or fused to a therapeutic agent or drug in a first vial and one or more prophylactic or therapeutic agents, other than an antibody of the invention, in a second vial for use in the prevention, treatment, management, amelioration, detection, monitoring or diagnosis of B-cell mediated diseases including but not limited to allergic diseases, myelomas, diseases caused by monoclonal expansion of B-cells, autoimmune and inflammatory diseases, in particular a IgE-mediated disease. The kits may further comprise packaging materials and/or instructions.

TABLE 1

Legend for Sequence Listing

| SEQ ID NO: | Description |
|---|---|
| 1 | Human ε-migis amino acid sequence |
| 2 | Human µ-migis amino acid sequence |
| 3 | Human phosphoinositide binding protein epitope amino acid sequence |
| 4 | Human KIAA1227 epitope amino acid sequence |
| 5 | Human cεmx.migis peptide sequence |
| 6 | Portion of Human cεmx peptide sequence |
| 7 | D5 antibody $V_L$ nucleotide sequence |
| 8 | D5 antibody $V_H$ nucleotide sequence |
| 9 | D5 antibody $V_L$ amino acid sequence |
| 10 | D5 antibody $V_H$ amino acid sequence |

TABLE 1-continued

Legend for Sequence Listing

| SEQ ID NO: | Description |
|---|---|
| 11 | D5 $V_L$ CDR1 amino acid sequence |
| 12 | D5 $V_L$ CDR2 amino acid sequence |
| 13 | D5 $V_L$ CDR3 amino acid sequence |
| 14 | D5 $V_H$ CDR1 amino acid sequence |
| 15 | D5 $V_H$ CDR2 amino acid sequence |
| 16 | D5 $V_H$ CDR3 amino acid sequence |
| 17 | ADWPGPP*ELDVCVEEAEGEAPW* |
| 18 | DWPGPP*ELDVCVEEAEGEAPW* |
| 19 | WPGPP*ELDVCVEEAEGEAPW* |
| 20 | PGPP*ELDVCVEEAEGEAPW* |
| 21 | GPP*ELDVCVEEAEGEAPW* |
| 22 | PP*ELDVCVEEAEGEAPW* |
| 23 | P*ELDVCVEEAEGEAPW* |
| 24 | RADWPGPP*ELDVCVEEAEGEAP* |
| 25 | RADWPGPP*ELDVCVEEAEGEA* |
| 26 | RADWPGPP*ELDVCVEEAEGE* |
| 27 | RADWPGPP*ELDVCVEEAEG* |
| 28 | RADWPGPP*ELDVCVEEAE* |
| 29 | RADWPGPP*ELDVCVEEA* |
| 30 | RADWPGPP*ELDVCVEE* |
| 31 | RADWPGPP*ELDVCVE* |
| 32 | RADWPGPP*ELDVCV* |
| 33 | RADWPGPP*ELDVC* |
| 34 | RADWPGPP*ELDV* |
| 35 | RADWPGPP*ELD* |
| 36 | RADWPGPP*EL* |
| 37 | RADWPGPP*E* |
| 38 | ADWPGPP*ELDVCVEEAEGEAP* |
| 39 | DWPGPP*ELDVCVEEAEGEA* |
| 40 | GPP*ELD* |
| 41 | PGPP*ELDV* |
| 42 | PGPP*ELD* |
| 43 | GPP*ELDV* |
| 44 | WPGPP*ELDVC* |
| 45 | PGPP*ELDVC* |
| 46 | WPGPP*ELDV* |
| 47 | Human δ-migis amino acid sequence |
| 48 | Human γ-migis amino acid sequence |
| 49 | Human α-migis amino acid sequence |
| 50 | A1c antibody $V_L$ nucleotide sequence |
| 51 | A1c antibody $V_H$ nucleotide sequence |
| 52 | A1c antibody $V_L$ amino acid sequence |
| 53 | A1c antibody $V_H$ amino acid sequence |
| 54 | A1c $V_L$ CDR1 amino acid sequence |
| 55 | A1c $V_L$ CDR2 amino acid sequence |
| 56 | A1c $V_L$ CDR3 amino acid sequence |
| 57 | A1c $V_H$ CDR1 amino acid sequence |
| 58 | A1c $V_H$ CDR2 amino acid sequence |
| 59 | A1c $V_H$ CDR3 amino acid sequence |
| 60 | B1 antibody $V_L$ nucleotide sequence |
| 61 | B1 antibody $V_H$ nucleotide sequence |
| 62 | B1 antibody $V_L$ amino acid sequence |
| 63 | B1 antibody $V_H$ amino acid sequence |
| 64 | B1 $V_L$ CDR1 amino acid sequence |
| 65 | B1 $V_L$ CDR2 amino acid sequence |
| 66 | B1 $V_L$ CDR3 amino acid sequence |
| 67 | B1 $V_H$ CDR1 amino acid sequence |
| 68 | B1 $V_H$ CDR2 amino acid sequence |
| 69 | B1 $V_H$ CDR3 amino acid sequence |
| 70 | F4 antibody $V_L$ nucleotide sequence |
| 71 | F4 antibody $V_H$ nucleotide sequence |
| 72 | F4 antibody $V_L$ amino acid sequence |
| 73 | F4 antibody $V_H$ amino acid sequence |
| 74 | F4 $V_L$ CDR1 amino acid sequence |
| 75 | F4 $V_L$ CDR2 amino acid sequence |
| 76 | F4 $V_L$ CDR3 amino acid sequence |
| 77 | F4 $V_H$ CDR1 amino acid sequence |
| 78 | F4 $V_H$ CDR2 amino acid sequence |
| 79 | F4 $V_H$ CDR3 amino acid sequence |
| 80 | D9 antibody $V_H$ nucleotide sequence |
| 81 | D9 antibody $V_H$ amino acid sequence |
| 82 | D9 $V_H$ CDR1 amino acid sequence |
| 83 | D9 $V_H$ CDR2 amino acid sequence |
| 84 | D9 $V_H$ CDR3 amino acid sequence |

TABLE 1-continued

Legend for Sequence Listing

| SEQ ID NO: | Description |
|---|---|
| 85 | scrambled form of ε-migis |
| 86 | IgG migis peptide with 8 additional amino acids at N-terminus |
| 87 | IgM migis peptide with 8 additional amino acids at N-terminus |

ε-migis amino acid residues are underlined
cεmx amino acid residues are bolded

6. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

6.1 Example 1

Development of Human Anti ε-migis Antibodies 15 unique phage clones that bound the ε-migis peptide (SEQ ID NO.:1) were isolated from a naïve human Fab phage display library using standard soluble and immobilized antigen panning techniques. All of the isolated antibodies specifically bound the ε-migis peptide but not to a scrambled peptide by ELISA. However, only one antibody, designated "A1c," (see FIG. 13) bound to cells expressing membrane anchored IgE. Upon further investigation it was determined that A1c also bound to other cell types including membrane IgM, IgA expressing cells and T-cells (data not shown). Examination of the ε-migis amino acid sequence revealed that part of the epitope is shared by other proteins including phosphoinositide binding protein, recently found to be the receptor for anthrax PA (Lu Q, et al., *Proc Natl Acad Sci USA*. 2004, 101:17246-17251, and unknown hypothetical protein, KIAA1227 (see FIG. 1B). A peptide corresponding to the region of the phosphoinositide binding protein that is similar to ε-migis (peptide vi in "Materials and Methods") was synthesized and used in an ELISA assay for examining binding of the anti ε-migis antibody. As shown in FIG. 7A it was found that the anti ε-migis antibody A1c bound to this peptide nearly as efficiently as it did to ε-migis peptide. In contrast antibodies that bound to cεmx-migis (see below) did not bind to this peptide. Together, these results suggest that the ε-migis peptide may not be an effective target for mIgE specific antibody binding.

To obtain human antibody clones with greater specificity a second peptide, designated "cεmx.migis" (SEQ ID NO:5) containing an additional eight amino acids from the cεmx region (FIG. 2) of the long isoform of human membrane anchored ε-chain, was used for isolation of additional clones from the human antibody phage display library. After three rounds of panning, phage isolates from about 2500 individual bacterial colonies were screened by peptide ELISA. The binding characteristics of ~364 isolated clones positive for binding to the cεmx.migis peptide was examined ELISA studies demonstrated that roughly two thirds of the clones bound both the cεmx.migs and ε-migis peptides, the remaining third (~108) bound only the cεmx.migs peptide. These did not bind to ε-migis or other related peptides that were tested (data not shown). 20 were randomly chosen for further study and converted to full IgG. FACS analysis of the cεmx.migis specific clones revealed that like the ε-migis specific clones initially isolated the cεmx-migis antibodies fell into two categories. About 25% did not bind to cells expressing membrane anchored IgE while ~75% were not specific for cells expressing membrane anchored IgE (i.e., bound to all human cells tested irrespective of whether mIgE was expressed or not, similar to clone A1c).

Using standard screening methods both the ε-migis and the cεmx.migis peptide specific antibodies either bound to human cells irrespective of mIgE expression or did not bind to cells at all. Together, these studies indicate that one predominant epitope of the ε-migis peptide is shared by at least one widely expressed cell surface protein (designated "shared-epitope") and that an ε-migis-dependent epitope of the cεmx.migis peptide is either hidden or absent when the ε-chain is present on the cell surface (designated "hidden-epitope"). Using standard panning and screening methods the majority of clones isolated recognized these predominant epitopes. For example, A1c binds the shared-epitope while CP1-B1 (also designated "B1", see FIG. 14) binds the hidden-epitope.

Figure 6B:
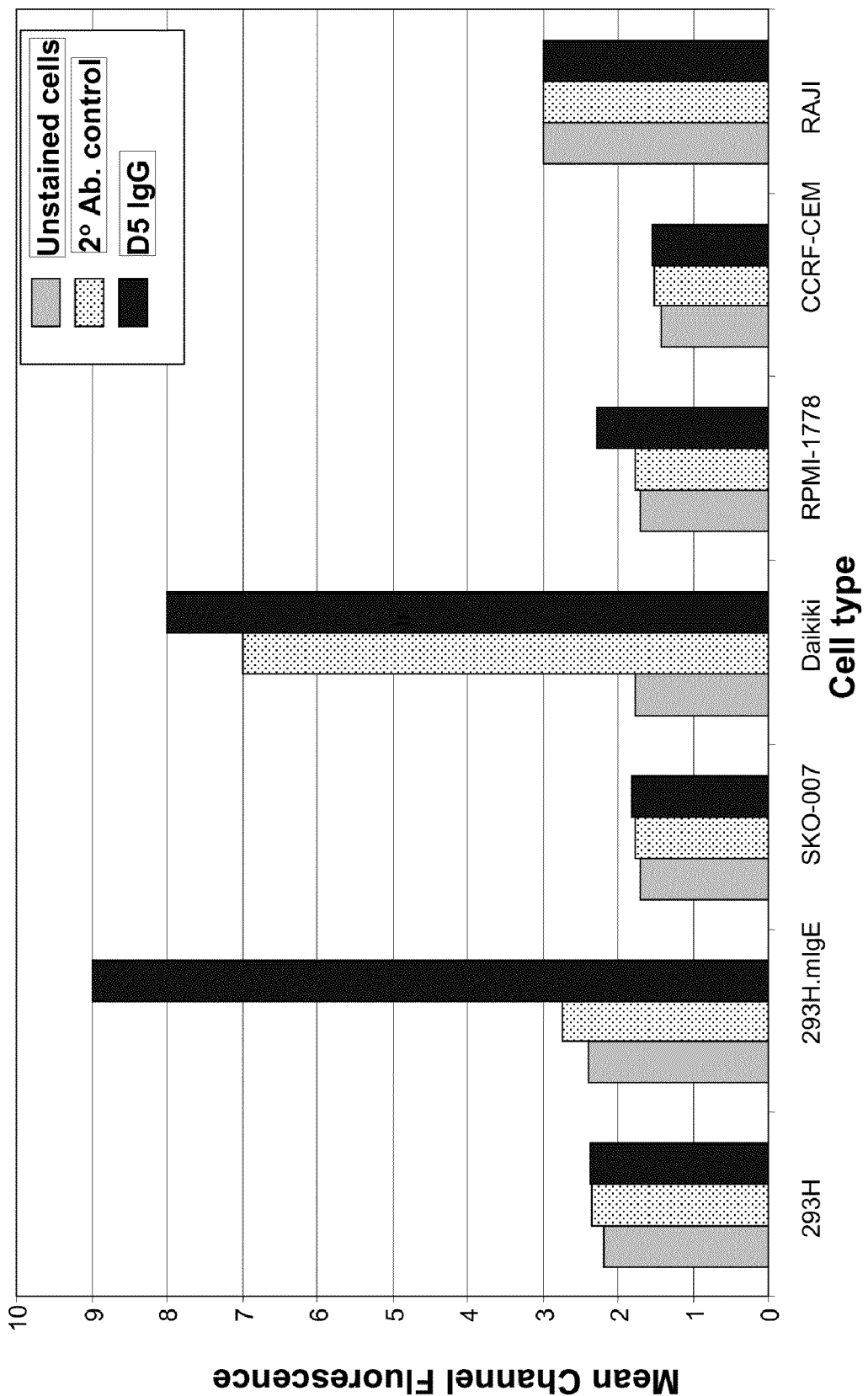

To obtain human antibody clones recognizing other epitopes present on the cεmx-migis peptide an inhibition ELISA technique was devised where antibodies specific for both the shared- and hidden-epitopes (A1c and B1, respectively) were used identify only the clones which may have a different epitope specificity. The unique clones isolated in the cεmx.migis screen were screened for those which were not inhibited by antibodies specific for the shared- and hidden-epitopes (see, for example, FIGS. 3 and 4). Several different profiles were seen, antibodies which were inhibited by either A1c or B1, antibodies which were NOT inhibited by either A1c or B1 (see, for example FIG. 4, open arrows) in addition, several antibodies were identified which were inhibited by both A1c and B1 (see, for example FIG. 4, solid arrows). About 25 clones were identified that were specific for cεmx.migis peptide which were not inhibited by either A1c or B1, suggesting that these clones probably bound to an epitope other than the A1c or B1 epitope, were selected for further screening. These selected Fab clones were converted to full length IgG with the exception of clone D9 which lacks a light chain. FACS analysis demonstrated that D5 antibody (also termed D5 IgG) specifically binds only cells expressing membrane anchored IgE (FIGS. 5, 6 and 8) and ELISA studies demonstrated that D5 specifically binds on the cεmx.migis peptide and not the shared epitope represented by the PIBP peptide (FIG. 7A). Two additional clones, F4 and D9, were also found to bind selectively to 293 transfectants that expressed mIgE but not untransfected cells (FIG. 8). As shown in FIG. 6B, the D5 antibody also did not bind to human B-cell lines RPMI 1788 which expresses mIgM, Daikiki which expresses human mIgA, RAJI cells which secrete IgG and to CCRF-CEM which is a T-cell line or to SKO-007 is a human B-lymphoid cell line that is reported to express mIgE but in practice we and others have consistently found that this expression is very weak and unstable (our unpublished data and Chen H Y, et al., *Int Arch Allergy Immunol.*, 2002, 128: 315-24). FIG. 8 demonstrates that D5, F4 and D9 antibodies only bind to cells expressing membrane anchored IgE. Thus, these antibodies represents fully human antibodies that specifically bind membrane anchored ε-chains and do not significantly cross react with other cell surface proteins. Further studies as described below were carried out with clone D5.

Clone D9 may be optimized as a heavy chain only antibody or used as a heavy chain partner to screen for a light chain partner with the appropriate binding specificity.

Materials and Methods

Peptides: Aminohexaminoic acid linker (Ahx) followed by a biotinylated lysine (K-biot) residue were attached to the C-terminal end of each peptide. The different peptides are summarized in Table 2. All peptides except (iii) and (iv) were dissolved in PBS, pH, 7.4. Peptides (iii) and (iv) were dissolved in 10% DMSO because they were not soluble in PBS.

TABLE 2

Peptides Used for Screening

| Peptide | Sequence | SEQ ID NO: |
|---|---|---|
| (i) ϵ-migis peptide | ELDVCVEEAEGEAPW-(Ahx)(K-Biot) | 1 |
| (ii) cϵmx.migis peptide | RADWPGPPELDVCVEEAEGEAPW-(Ahx)(K-Biot) | 5 |
| (iii) scrambled form of ϵ-migis | GEDWCEVALEPAEVE-(Ahx)(K-Biot) | 85 |
| (iv) IgG migis peptide | KSLSLSPELQLEESCAEAQDGELDG-(Ahx)(K-Biot) | 86 |
| (v) IgM migis peptide | ERTVDKSTEGEVSADEEGFEN-(Ahx)(K-Biot) | 87 |
| (vi) peptide from phosphoinositide binding protein | TQLLCVEAFEGEEPW-(Ahx)(K-Biot) | 3 |
| (vii) peptide from a human gene accession number K1AA1227 | VKEEPVEEAEEEAPE-(Ahx)(K-Biot) | 4 |

Recombinant Proteins: Three different recombinant proteins were used in the study. These were (i) IgE that lacks any membrane tethering portion, (ii) IgE with 52 amino acids corresponding to the cϵmx portion at the end of CH4 domain and (iii) IgE with 67 amino acids corresponding to the cϵmx and -migis portion of mIgE at the end of the CH4 domain. The only difference between the protein that lacks the carboxyl terminal extension and the ones with the cϵmx and cϵmx.migis portion is at the end of the CH4. IgE ends with the sequence SVNPGK. In other two proteins with the cϵmx and cϵmx.migis at the end of CH4 domain, the CH4 ends with SVNP. This difference corresponds with the difference seen between soluble IgE (sIgE) and mIgE. The vectors for these proteins were made by cloning the open reading frame coding for the heavy and light chains under CMV promoter in a mammalian expression vector designed for secretion of protein into the culture medium. Because the three proteins were expressed in exceeding low level they were not purified. Their presence in cell culture supernatant were monitored by a sandwich ELISA that involved capturing the protein with an anti-human IgE Fc specific antibody (5 µg/ml in PBS, 7.4) and detecting with anti-human kappa antibody conjugated with HRP (data not shown). In another experiment that was done to study the binding of these three different proteins by a cϵmx.migis specific antibody (referred later on as D5) the proteins were captured by D5 IgG (5 µg/ml in PBS, 7.4) immobilized on ELISA plates through anti-IgG-Fc antibodies and were detected with anti-human IgE Fc specific antibody conjugated with HRP (see, FIG. 7C). Synagis® which is a therapeutic monoclonal antibody that binds to the F-protein of respiratory syncytial virus was used as a negative control to show that binding by D5 IgG was specific.

Phage Library: The phage library used in these studies is called the FAB-310 Fab library obtained from Dyax Corp. The library is a fully human Fab library. The complexity of the library is over $10^{10}$ and has been shown to be an effective source of antibodies against a wide variety of human and non-human antigens (Hoet R M et al., Nature Biotechnology 2005, 23, 344-8).

ϵ-migis peptide Panning: (1) In solution: At each round the phage library was blocked with 3% BSA in TPBS (0.1% Tween 20 in PBS, pH 7.2) for 1 hour and then deselected on streptavidin coated magnetic beads for 2 hours. The library was then incubated with the ϵ-migis peptide biotinylated through a linker at the C-terminus. The peptide-phage complex (as well as free peptide) was captured on streptavidin coated magnetic beads. The beads were then washed 7 times each with TPBS and PBS, each wash being of 2' duration. Following the washes the phage was eluted using 100 mM Triethylamine in water for 15 minutes. The eluted phage was immediately neutralized with 0.5 M Tris, pH 8, titered and amplified by infecting E. coli for subsequent round of panning. Peptide concentrations of 2.0 µg/ml (~1 µM) were used for rounds 1 and 2 and 0.20 µg/ml (~0.1 µM) was used for round 3. (2) Immobilized: As described for the solution panning the phage library was blocked with 3% BSA in TPBS (0.1% Tween 20 in PBS, pH 7.2) and then deselected on Neutravidin coated immunotubes coated with 1 ml of 2 µg/ml of Neutravidin. In a separate tube the biotinylated ϵ-migis peptide was captured on a 5 µg/ml coated neutravidin surface and the deselected library was incubated on the captured peptide bed. The bed was washed 15 times each with TPBS and PBS and the phage were eluted with 100 mM Triethylamine in water for 15'. As described above the eluted phage was immediately neutralized, titered and amplified by infecting E. coli for subsequent round of panning. Peptide concentrations of 25 µg/ml (~13 µM) were used for rounds 1 and 2 and 2.5 µg/ml (~1.3 µM) was used for round 3. Approximately 500 clones were screened by ELISA for those that bound only to the ϵ-migis peptide and not to a scrambled peptide. There were a total of 51 (10%) ELISA positive clones representing 18 unique Fabs. These 18 clones were batch converted to IgG. Of the full IgG clones recovered 12 specifically bound ϵ-migis but not to a scrambled peptide. Only one clone, A1c, showed the ability to bind mIgE expressing cells but was subsequently found to bind cells even in the absence of mIgE and later determined to bind the shared epitope (see, FIG. 7A).

cϵmx.migis peptide Panning: Panning was performed essentially as described above for ϵ-migis peptide panning (1)

In solution: the blocked library was deselected on streptavidin coated magnetic beads then incubated with the cϵmx.migis peptide biotinylated through a linker at the C-terminus. The peptide-phage complex (as well as free peptide) was captured on streptavidin coated magnetic beads. The beads were then washed and the phage eluted. Peptide concentrations of 2.0 μg/ml were used for rounds 1 and 2 and 0.25 μg/ml was used for round 3. (2) Immobilized: the blocked library was deselected on Neutravidin coated immunotubes. The biotinylated cϵmx.migis peptide was captured on a neutravidin surface and the deselected library was incubated on the captured peptide bed. The bed was washed and eluted. Peptide concentrations of 25 μg/ml were used for rounds 1 and 2 and 2.5 μg/ml was used for round 3. Approximately 2500 isolated clones were then screened by ELISA for binding to the cϵmx.migis peptide, 364 were positive. The positive clones were then screened for binding to both the cϵmx.migis and the ϵ-migis peptides. 256 clones bound to both cϵmx.migis and the ϵ-migis peptides while 108 preferentially bound to cϵmx.migis. Of 190 clones sequence analyzed, 120 were unique. 8 randomly picked clones were initially converted to IgGs. However, none specifically bound to cell expressing mIgE. The 120 unique clones from panning on the cϵmx-migis peptide were screened by inhibition ELISA for those that were not strongly inhibited by A1c. The results from some representative clones screened against A1c are shown in FIG. 3. A total of 66 clones were selected. These clones were consolidated and screened by inhibition ELISA for those clones that were not inhibited by A1c or B1. FIG. 4 shows the results from some representative clones screened against both A1c and B1.

ELISA Screening: For screening studies phage particles from single bacterial colonies were rescued in 96-well formats as described in Chowdhury et al. (Mol Immunol. 1997 January; 34(1):9-20.). The bacterial culture was then cooled down to 4° C. and the cells were removed by centrifugation at 3000-5000×g for 15' at 4° C. The supernatant containing recombinant phage particles were used for screening assays. Biotinylated cϵmx-migs peptide was immobilized on Neutravidin coated ELISA plates that had been blocked with 3% BSA in TPBS. After blocking the wells bacterial culture supernatant containing individual phage clones were added to the ELISA wells. After incubation for 60' at ambient temperature the wells were washed and the bound phage were detected with anti-M13 antibody conjugated to HRP. ELISA plates were developed with TMB substrate solution from Pierce. The reaction was stopped with 2 N sulphuric acid and the intensity of the color produced was measured at 450 nm.

Inhibition ELISA Screening: Biotinylated cϵmx-migs peptide was immobilized on Neutravidin coated ELISA plates as described above. Bacterial cultures containing individual phage clones isolated by peptide panning were added to separate ELISA wells along with an irrelevant IgG isotype (specific towards the F-protein of Respiratory Syncytial Virus) control or A1c (anti-shared epitope antibody) or B1 (anti-hidden epitope antibody). After incubation for 60' at ambient temperature the wells were washed and the bound phage clones were detected using an anti-M13 antibody coupled to HRP as described above. Some representative ELISA data from the inhibition screening is shown in FIGS. 3 and 4. Several clones, namely A8, CP3-B1, C3, C11, D2, D5, D8, D9, F4 and E6 were selected for conversion to IgG and analyzed for binding to membrane IgE transfected cells (see below).

Conversion and Expression of Full Length IgGs: The Fab gene in the phage display vector consist of the entire light chain separated from the Fd fragment by a DNA piece that represent a bacterial ribosome entry site (RBS). To convert a Fab fragment selected from the phage library into full IgG the Fab cassette was isolated by using unique restriction enzymes, ApaLI and NheI and ligated into a mammalian expression vector such that the Fd fragment is ligated in frame with the rest of the constant domains of the heavy chain. After this the bacterial RBS was removed by two other restriction sites and replaced by an IRES sequence that works for mammalian expression systems. The final vector is thus monocistronic where the light and heavy chain are transcribed into one mRNA but translated as two different chains.

Conversion of the Fabs to full IgGs was followed by the expression of the IgGs in 293 cells by transient transfection. 293 cells were transfected (using Lipofectamine 2000 from Invitrogen following the manufacturer's instruction) with the mammalian expression vectors coding for the IgG and cultured for 72 hours in DMEM containing ultra low IgG containing 10% FBS from Invitrogen. The IgG concentration in the conditioned media were estimated by a sandwich ELISA in which anti-human kappa antibody from Sigma was used to capture the human IgG from the conditioned culture media and anti-human IgG Fc antibody conjugated to HRP was used to detect the captured IgG. The amount of IgG present in the conditioned media was estimated by using purified human IgG1-k as a control antigen to generate a standard curve in an experiment run in parallel. After normalizing for the IgG concentration the conditioned supernatants were screened by ELISA for peptide binding and then binding to mIgE expressing cells in a FACS based assay.

Cell Line Generation: Nucleoporation was used for generating transfected cell lines. 293 cells were co-transfected with (i) a linearized bi-cistronic mammalian expression vector coding for the mIgE heavy chain and a light chain that binds to the EphA2 antigen or with another mIgE heavy and light chain pair that binds to the F-protein of Respiratory Syncytial Virus (RSV) and (ii) a linearized bi-cistronic mammalian expression vector that coded for CD79a (Igα) and CD79b (Igβ) that are known to associate with membrane immunoglobulins to form the B-cell receptor complex (BCR). 24 hours after transfection cells were seeded at 500 cells/well of 96 well plates and subjected to double selection by 500 μg/ml neomycin (for the mIgE expressing plasmid) and 100 μg/ml hygromycin (for the CD79a and CD79b expressing plasmid) in Dulbecco's Modified Eagle's Medium (DMEM) (from Invitrogen, Carlsbad, Calif.). After 2-3 weeks colonies started to emerge. These were expanded and tested for expression of mIgE, CD79a and CD79b. The population with good expression of all three antigens was sorted by three color FACS into single cell/well giving rise to several clones with consistent expression of mIgE, CD79a and CD79b. These clones were then further sub-cloned by limited dilution cloning at 0.2 cell/well to ensure monoclonality. FIG. 17 is a bar graph of the FACS analysis of cell surface staining with anti-hu IgE, anti-Igα, anti-Igβ and a secondary antibody control demonstrating that clones 1, 2 and 5 stain for all three cell surface markers.

FACS Analysis: For FACS experiment all steps were carried out at 4° C. The 8 clones identified by competition ELISA were tested for their ability to bind mIgE. Briefly, cells transiently expressing mIgE (293-mIgE) were stained with anti-human κ, anti-human λ, anti-human IgG-Fc and antibodies derived from each of the clones described above (A8, CP3-B1, C3, C11, D2, D5, D8, and E6) as well as, A1c and B1 (shown as CP1-B1). Cells were then analyzed by FACS (see FIG. 5).

Cells expressing mIgE (293-mIgE), IgA (Daikiki), IgM (RPMI 1788) or no immunoglobulin (293 and CCRF-CEM)

were stained with, secondary antibody alone (goat anti-mouse (GtaMu) or Guinea pig anti-human (GaHu)) or primary (mouse anti-human IgE (MuαHuIgE) or D5) plus secondary or left unstained. Cells were then analyzed by FACS (see FIG. 6). Because the experiment was done with transiently transfected 293 cells both the percentage of cells showing staining and the change in mean fluorescence was plotted in FIG. 6A.

Similar experiments were performed using 2×10$^4$ 293 or 293 stably transfected with mIgE, CD79a and CD79b or other human B-cell lines such as RAJI, RPMI 1740, Daikiki or the T-cell line CCRF-CEM. The cells were first blocked with 2% BSA in PBS (blocker). They were then exposed to the conditioned media containing 2-5 μg human IgG in 200 μl blocker for 45'. Cells were washed three times using 5 ml blocker and centrifugation for 5' at 400 g. The cells were then stained with anti-human IgG1 Fc specific antibody labeled with Alexar 488 and analyzed in a Guava. IgGs of clones that showed binding were then studied further by doing the FACS staining both in the absence and presence of the migis or a scrambled peptide (20 ug/ml) (data not shown).

6.2 Example 2

Binding Characteristics of D5, a Human Anti-cϵmx.migis Antibody

To further characterize the binding specificity of the human anti cϵmx.migis antibody D5, a recombinant IgE antibody (rIgE), was generated and expressed in 293 cells. Several variants of soluble rIgE in which the cεmx region (52 amino acid residues) or the cεmx-migis region (67 amino acid residues) were fused to the CH4 end (designated rIgE.cεmx and rIgE.cεmx.migis, respectively) were also generated and expressed. ELISA analysis demonstrated that the D5 antibody binds only rIgE.cεmx.migis and not IgE or IgE.cεmx indicating that D5 does not significantly bind to the cεmx region alone. This suggests that the cεmx.migis specific D5 antibody does not bind to soluble IgE and binds IgE only when it has both the cεmx and the migis peptide at its C-terminus. These data also suggest that a portion of the ε-migis peptide is involved in forming the epitope recognized by D5 (FIG. 7B).

A second series of recombinant immunoglobulin molecules were also generated in which the cεmx region or the cεmx-migis region were fused to the CH3 end of an IgG (designated rIgG.cεmx and rIgG.cεmx.migis, respectively). ELISA analysis again demonstrated that the D5 antibody only binds rIgG.cεmx.migis (FIG. 7C). This data indicates that the confirmation of cεmx.migis region may be similar in the context of both IgE and IgG constant regions.

To further define the epitope recognized by D5 BIAcore analysis of binding to cεmx.migis and ε-migis peptides was performed. As shown in FIG. 9, D5 does not bind to the ε-migis peptide alone but rather binds to an epitope only present in the cεmx.migis peptide. This data confirms the ELISA studies described above indicating that both the cεmx and the ε-migis amino acid residues are involved in forming the epitope recognized by D5.

Materials and Methods

Generation of rIgE and rIgE variants: the variable region of the heavy chain of an irrelevant antibody was used to generate a recombinant IgE (rIgE). The entire cεmx region (52 residues total) or the combined cεmx.migis region (67 residues) was fused to the CH4 end of the rIgE construct to generate rIgE.cεmx and rIgE.cεmx.migis, respectively. All three constructs were transfected into 293 cells for expression and the relative level of protein expressed was determined by a sandwich ELISA. Briefly, the various rIgE constructs were captured with an anti-light chain antibody and detected with an anti-IgE Fc antibody conjugated to HRP.

rIgE Binding ELISA Assay: D5 or the isotype control antibody (cont.) were captured by an anti-IgG Fc antibody bound to an ELISA plate. Conditioned media from cells expressing the various rIgE constructs were added to the ELISA wells and binding was detected using an anti-IgE Fc antibody conjugated to HRP.

BIAcore Analysis: the interaction of D5 with streptavidin-captured cεmx.migis and ε-migis peptides was monitored by surface plasmon resonance detection using a BIAcore 3000 instrument (Pharmacia Biosensor, Uppsala, Sweden). Briefly, the peptides were captured on a streptavidin coated chip and the D5 antibody was passed over the surface.

6.3 Example 3

Biological Characteristics of D5, a Human Anti-cεmx.migis Antibody

D5 was tested in an ADCC assay to demonstrate that a human antibody against cεmx.migis was useful for depleting cell expressing membrane bound IgE. D5 was seen to mediate ADCC activity only against 293 cell that were transfected to express membrane bound IgE (FIGS. 10 and 11). The ability to mediate ADCC activity could be specifically inhibited by the addition of the cεmx.migis peptide (FIG. 11).

A variant of the D5 antibody was generated having an aspartate at position 239, a leucine at position 330 and a glutamate at position 332 in the Fc region of the antibody (the numbering system is that of the EU index as set forth in Kabat et al., 1991, NIH Publication 91-3242, National Technical Information Service, Springfield, Va.), this variant was designated "D53M". The presence of these amino acid residues at these positions in the Fc domain of IgG has been shown to enhance ADCC activity. As shown in FIGS. 10 and 11, an enhancement in ADCC activity is seen for the D53M Fc variant antibody. As seen for the D5 antibody, the ability of the D53M antibody to mediate ADCC is inhibited by the cεmx.migis peptide (FIG. 11).

Materials and Methods

Generation of D53M Fc variant: To generate the D53M variant the variable region of the D5 heavy chain was fused to an Fc region variant having the following non-wild type amino acid resides, 239D, 330L and 332E.

Preparation of Peripheral Blood Mononuclear Cells (Pbmcs): Human Blood samples were collected from several individual healthy volunteers using heparinized syringes, diluted with twice the volume of PBS buffer, layered onto a Lymphoprep gradient (ICN, Irvine, Calif.), and centrifuged at 400 g for 30 minutes at room temperature. Peripheral blood mononuclear cells (PBMCs) were harvested from the interface, washed 3 times with PBS.

ADCC: Antibody-dependent cell cytotoxicity (ADCC) was assayed in a non-radioactive lactate dehydrogenase (LDH) release assay (Promega Corporation, Madison, Wis.). Briefly, 293 or 293-mIgE target cells were distributed into 96-well plates and pre-incubated with serial dilution of antibodies (50 μl) for 20 min at 37° C. Human effector cells (100 μl) were then added at ratios from 25:1 to 50:1. Human effector cells were peripheral blood mononuclear cells (PBMC) purified from healthy donors using Lymphocyte Separation Medium (MP Biomedicals, Irvine, Calif.). After incubation, plates were centrifuged, and cell death was analyzed by measuring the release of LDH into the cell supernatant with a 30-minute coupled enzymatic assay. The percentage of specific lysis was calculated according to the formula:

% specific lysis=$100 \times (E_X - E_{spon} - T_{spon})/(T_{max} - T_{spon})$, where $E_X$ represents the release from experimental wells, $E_{spon}$ is the spontaneous release of effector cells alone, $T_{spon}$ is spontaneous release of target cells alone, and $T_{max}$ is the maximum release from lysed target cells.

Additional assays were performed using 293 cells and 293 cells expressing mIgE and CD79a and CD79b (FIG. 10C). The 293 cells and 293 cells expressing mIgE and CD79a and CD79b were harvested using cell dissociation buffer (from Invitrogen) and re-suspended in RPMI 1640 supplemented with 5% FBS (assay buffer) at a density of $2 \times 10^5$ cells/ml. These were then added to a 96-well round bottom tissue culture plate (BD Biosciences, Bedford, Mass.) at 50 μl/well along with various concentrations of antibody at 50 μl/well in assay buffer (see above) and pre-incubated at 37° C. for 30 minutes. PBMCs were resuspended at $5 \times 10^6$ cells/ml (for an Effector (E):Target (T) ratio of 50:1) and $2.5 \times 10^6$/ml (for an E:T ratio of 25:1) in assay buffer (see above) and added at 100 μl/well to the assay plate. 25 μl/well of 9% Triton X-100 (Promega, Madison, Wis.) was added as a control for complete lysis. The plates were centrifuged at 300 g for 3 minutes and incubation at 37° C. was continued for 4 hours. Plates were then centrifuged at 300 g for 10 minutes and 50 μl of supernatant from each well was transferred to MaxiSorp 96-well plates (BD Biosciences, Bedford, Mass.). 50 μl of reconstituted substrate mix (CytoTox 96 Non-Radioactive Cytotoxicity Assay kit, Promega, Madison, Wis.) was then added to all wells and incubated in the dark at room temperature for 30 minutes. 50 μl of stop solution (Promega, Madison, Wis.) was added to each well and lactate dehydrogenase (LDH) release was quantified by measuring the absorbance at 490 nm. % cytotoxicity was calculated as described above.

Whereas, particular embodiments of the invention have been described above for purposes of description, it will be appreciated by those skilled in the art that numerous variations of the details may be made without departing from the invention as described in the appended claims.

All publications, patents and patent applications cited herein are incorporated herein by reference in their entirety and for all purposes to the same extent as if each individual publication or patent or patent application was specifically and individually indicated to be incorporated by reference in its entirety for all purposes. In addition, U.S. Provisional Patent Application No. 60/721,525 filed Sep. 29, 2005 is incorporated by reference in its entirety for all purposes.

---

The invention claimed is:

1. An isolated antibody which specifically binds the peptide sequence of SEQ ID NO: 5, wherein said antibody does not bind the polypeptide of SEQ ID NO:1, SEQ ID NO:6, SEQ ID NO:3 and/or SEQ ID NO:4 and wherein said antibody comprises a substitution within the Fc region that enhances ADCC activity.

2. The isolated antibody of claim 1, wherein said antibody comprises:
   a light chain complementarity determining region 1 ($V_L$-CDR1) comprising the amino acid sequence of SEQ ID NO: 11;
   a light chain complementarity determining region 2 ($V_L$-CDR2) comprising the amino acid sequence of SEQ ID NO: 12;
   a light chain complementarity determining region 3 ($V_L$-CDR3) comprising the amino acid sequence of SEQ ID NO: 13;
   a heavy chain complementarity determining region 1 ($V_H$-CDR1) comprising the amino acid sequence of SEQ ID NO: 14;
   a heavy chain complementarity determining region 2 ($V_H$-CDR2) comprising the amino acid sequence of SEQ ID NO: 15; and
   a heavy chain complementarity determining region 3 ($V_H$-CDR3) comprising the amino acid sequence of SEQ ID NO: 16.

3. The isolated antibody of claim 1, wherein said antibody comprises:
   a light chain complementarity determining region 1 ($V_L$-CDR1) comprising the amino acid sequence of SEQ ID NO: 74;
   a light chain complementarity determining region 2 ($V_L$-CDR2) comprising the amino acid sequence of SEQ ID NO: 75;
   a light chain complementarity determining region 3 ($V_L$-CDR3) comprising the amino acid sequence of SEQ ID NO: 76;
   a heavy chain complementarity determining region 1 ($V_H$-CDR1) comprising the amino acid sequence of SEQ ID NO: 77;
   a heavy chain complementarity determining region 2 ($V_H$-CDR2) comprising the amino acid sequence of SEQ ID NO: 78; and
   a heavy chain complementarity determining region 3 ($V_H$-CDR3) comprising the amino acid sequence of SEQ ID NO: 79.

4. The isolated antibody of claim 1, wherein said antibody comprises:
   a heavy chain complementarity determining region 1 ($V_H$-CDR1) comprising the amino acid sequence of SEQ ID NO: 82;
   a heavy chain complementarity determining region 2 ($V_H$-CDR2) comprising the amino acid sequence of SEQ ID NO: 83; and
   a heavy chain complementarity determining region 3 ($V_H$-CDR3) comprising the amino acid sequence of SEQ ID NO: 84.

5. The isolated antibody of claim 1, wherein the substitution within the Fc region is an aspartate at position 239 and/or a leucine at position 330 and/or a glutamate at position 332, wherein the numbering system is that of the EU index as set forth in Kabat.

6. A method of ameliorating or treating and IgE-mediated disease in a human comprising administering to an individual in need of such amelioration or treatment an effective amount of the isolated antibody of claim 1.

7. An isolated antibody which specifically binds the peptide sequence of SEQ ID NO: 5, wherein said antibody does not bind the polypeptide of SEQ ID NO:1, SEQ ID NO:6, SEQ ID NO:3 and/or SEQ ID NO:4 and wherein said antibody has an altered glycosylation pattern that enhances ADCC activity.

8. The isolated antibody of claim 7, wherein said antibody comprises:
   a light chain complementarity determining region 1 ($V_L$-CDR1) comprising the amino acid sequence of SEQ ID NO: 11;
   a light chain complementarity determining region 2 ($V_L$-CDR2) comprising the amino acid sequence of SEQ ID NO: 12;
   a light chain complementarity determining region 3 ($V_L$-CDR3) comprising the amino acid sequence of SEQ ID NO: 13;
   a heavy chain complementarity determining region 1 ($V_H$-CDR1) comprising the amino acid sequence of SEQ ID NO: 14;
   a heavy chain complementarity determining region 2 ($V_H$-CDR2) comprising the amino acid sequence of SEQ ID NO: 15; and
   a heavy chain complementarity determining region 3 ($V_H$-CDR3) comprising the amino acid sequence of SEQ ID NO: 16.

9. The isolated antibody of claim 7, wherein said antibody comprises:
   a light chain complementarity determining region 1 ($V_L$-CDR1) comprising the amino acid sequence of SEQ ID NO: 74;
   a light chain complementarity determining region 2 ($V_L$-CDR2) comprising the amino acid sequence of SEQ ID NO: 75;
   a light chain complementarity determining region 3 ($V_L$-CDR3) comprising the amino acid sequence of SEQ ID NO: 76;
   a heavy chain complementarity determining region 1 ($V_H$-CDR1) comprising the amino acid sequence of SEQ ID NO: 77;
   a heavy chain complementarity determining region 2 ($V_H$-CDR2) comprising the amino acid sequence of SEQ ID NO: 78; and
   a heavy chain complementarity determining region 3 ($V_H$-CDR3) comprising the amino acid sequence of SEQ ID NO: 79.

10. The isolated antibody of claim 7, wherein said antibody comprises:
    a heavy chain complementarity determining region 1 ($V_H$-CDR1) comprising the amino acid sequence of SEQ ID NO: 82;
    a heavy chain complementarity determining region 2 ($V_H$-CDR2) comprising the amino acid sequence of SEQ ID NO: 83; and
    a heavy chain complementarity determining region 3 ($V_H$-CDR3) comprising the amino acid sequence of SEQ ID NO: 84.

11. The isolated antibody of claim 7, wherein the altered glycosylation pattern is hypofucosylation.

12. A method of ameliorating or treating and IgE-mediated disease in a human comprising administering to an individual in need of such amelioration or treatment an effective amount of the isolated antibody of claim 7.

13. A single-chain multi-functional polypeptide comprising (a) a first domain comprising an antigen binding-site of an isolated antibody or antibody fragment which specifically binds the peptide sequence of SEQ ID NO: 5, wherein said antibody or antibody thereof does not bind the polypeptide of SEQ ID NO:1, SEQ ID NO:6, SEQ ID NO:3 and/or SEQ ID NO:4; and (b) a second domain comprising an antigen binding site of an antibody or antibody fragment which specifically binds the CD3 antigen.

14. The single-chain multi-functional polypeptide of claim 13, wherein said first domain comprises:
    a light chain complementarity determining region 1 ($V_L$-CDR1) comprising the amino acid sequence of SEQ ID NO: 11;
    a light chain complementarity determining region 2 ($V_L$-CDR2) comprising the amino acid sequence of SEQ ID NO: 12;
    a light chain complementarity determining region 3 ($V_L$-CDR3) comprising the amino acid sequence of SEQ ID NO: 13;
    a heavy chain complementarity determining region 1 ($V_H$-CDR1) comprising the amino acid sequence of SEQ ID NO: 14;
    a heavy chain complementarity determining region 2 ($V_H$-CDR2) comprising the amino acid sequence of SEQ ID NO: 15; and
    a heavy chain complementarity determining region 3 ($V_H$-CDR3) comprising the amino acid sequence of SEQ ID NO: 16.

15. The single-chain multi-functional polypeptide of claim 13, wherein said first domain comprises:
    a light chain complementarity determining region 1 ($V_L$-CDR1) comprising the amino acid sequence of SEQ ID NO: 74;
    a light chain complementarity determining region 2 ($V_L$-CDR2) comprising the amino acid sequence of SEQ ID NO: 75;
    a light chain complementarity determining region 3 ($V_L$-CDR3) comprising the amino acid sequence of SEQ ID NO: 76;
    a heavy chain complementarity determining region 1 ($V_H$-CDR1) comprising the amino acid sequence of SEQ ID NO: 77;
    a heavy chain complementarity determining region 2 ($V_H$-CDR2) comprising the amino acid sequence of SEQ ID NO: 78; and
    a heavy chain complementarity determining region 3 ($V_H$-CDR3) comprising the amino acid sequence of SEQ ID NO: 79.

16. The single-chain multi-functional polypeptide of claim 13, wherein said first domain comprises:
    a heavy chain complementarity determining region 1 ($V_H$-CDR1) comprising the amino acid sequence of SEQ ID NO: 82;
    a heavy chain complementarity determining region 2 ($V_H$-CDR2) comprising the amino acid sequence of SEQ ID NO: 83; and
    a heavy chain complementarity determining region 3 ($V_H$-CDR3) comprising the amino acid sequence of SEQ ID NO: 84.

17. A method of ameliorating or treating and IgE-mediated disease in a human comprising administering to an individual in need of such amelioration or treatment an effective amount of the isolated antibody of claim 13.

* * * * *

SEQUENCE LISTING

```
<160> NUMBER OF SEQ ID NOS: 87

<210> SEQ ID NO 1
<211> LENGTH: 15
<212> TYPE: PRT
<213> ORGANISM: Homo sapiens

<400> SEQUENCE: 1

Glu Leu Asp Val Cys Val Glu Glu Ala Glu Gly Glu Ala Pro Trp
1               5                   10                  15

<210> SEQ ID NO 2
<211> LENGTH: 13
<212> TYPE: PRT
<213> ORGANISM: Homo sapiens

<400> SEQUENCE: 2

Glu Gly Glu Val Ser Ala Asp Glu Glu Gly Phe Glu Asn
1               5                   10

<210> SEQ ID NO 3
<211> LENGTH: 15
<212> TYPE: PRT
<213> ORGANISM: Homo sapiens

<400> SEQUENCE: 3

Thr Gln Leu Leu Cys Val Glu Ala Phe Glu Gly Glu Glu Pro Trp
1               5                   10                  15

<210> SEQ ID NO 4
<211> LENGTH: 15
<212> TYPE: PRT
<213> ORGANISM: Homo sapiens

<400> SEQUENCE: 4

Val Lys Glu Glu Pro Val Glu Glu Ala Glu Glu Glu Ala Pro Glu
1               5                   10                  15

<210> SEQ ID NO 5
<211> LENGTH: 23
```

```
<212> TYPE: PRT
<213> ORGANISM: Homo sapiens

<400> SEQUENCE: 5

Arg Ala Asp Trp Pro Gly Pro Pro Glu Leu Asp Val Cys Val Glu Glu
1               5                   10                  15

Ala Glu Gly Glu Ala Pro Trp
            20

<210> SEQ ID NO 6
<211> LENGTH: 8
<212> TYPE: PRT
<213> ORGANISM: Homo sapiens

<400> SEQUENCE: 6

Arg Ala Asp Trp Pro Gly Pro Pro
1               5

<210> SEQ ID NO 7
<211> LENGTH: 345
<212> TYPE: DNA
<213> ORGANISM: Homo sapiens

<400> SEQUENCE: 7
gcacaagaca tccagatgac ccagtctcca ctctccctgc ccgtcaccct tggacagccg      60
gcctccatct cctgcaagtc tagtcaaagc ctcgtataca gggatggcat aacctacttg     120
agctggtttc aacagaggcc aggccaatct ccaaggcgtc taattataaa ggtctctaat     180
cgagactctg ggtcccaga cagattcagc ggcagtgggt cagactctaa tttcacactg      240
aaaatcagca gtgtggaggc tgaggatgtt gggctttatt tctgcatgca aggttcacac     300
tggcctttca ctttcggccc tgggaccaaa gtggatatca aacga                     345

<210> SEQ ID NO 8
<211> LENGTH: 351
<212> TYPE: DNA
<213> ORGANISM: Homo sapiens

<400> SEQUENCE: 8
gaagttcaat tgttagagtc tggtggcggt cttgttcagc ctggtggttc tttacgtctt      60
tcttgcgctg cttccggatt cactttctct aagtaccata tggtttgggt cgccaagct     120 cctggtaaag gtttggagtg ggtttcttct atcggtcctt ctggtggcaa tacttattat     180
gctgactccg ttaaaggtcg cttcactatc tctagagaca actctaagaa tactctctac     240
ttgcagatga acagcttaag ggctgaggac acagccacat attactgtgc gagagccctc     300
ggagctacct ttgactactg gggccaggga accctggtca ccgtctcaag c              351

<210> SEQ ID NO 9
<211> LENGTH: 113
<212> TYPE: PRT
<213> ORGANISM: Homo sapiens

<400> SEQUENCE: 9

Asp Ile Gln Met Thr Gln Ser Pro Leu Ser Leu Pro Val Thr Leu Gly
1               5                   10                  15

Gln Pro Ala Ser Ile Ser Cys Lys Ser Ser Gln Ser Leu Val Tyr Arg
            20                  25                  30

Asp Gly Ile Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
```

```
            50                  55                  60
Asp Arg Phe Ser Gly Ser Gly Ser Asp Ser Asn Phe Thr Leu Lys Ile
 65                  70                  75                  80

Ser Ser Val Glu Ala Glu Asp Val Gly Leu Tyr Phe Cys Met Gln Gly
                 85                  90                  95

Ser His Trp Pro Phe Thr Phe Gly Pro Gly Thr Lys Val Asp Ile Lys
            100                 105                 110

Arg

<210> SEQ ID NO 10
<211> LENGTH: 117
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Lys Tyr
                20                  25                  30

His Met Val Trp Val Arg Gln Ala Pro Gly Lys Gly Leu Glu Trp Val
             35                  40                  45

Ser Ser Ile Gly Pro Ser Gly Gly Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Ala Leu Gly Ala Thr Phe Asp Tyr Trp Gly Gln Gly Thr Leu
            100                 105                 110

Val Thr Val Ser Ser
        115

<210> SEQ ID NO 11
<211> LENGTH: 16
<212> TYPE: PRT
<213> ORGANISM: Homo sapiens

<400> SEQUENCE: 11

Lys Ser Ser Gln Ser Leu Val Tyr Arg Asp Gly Ile Thr Tyr Leu Ser
 1               5                  10                  15

<210> SEQ ID NO 12
<211> LENGTH: 7
<212> TYPE: PRT
<213> ORGANISM: Homo sapiens

<400> SEQUENCE: 12

Lys Val Ser Asn Arg Asp Ser
 1               5

<210> SEQ ID NO 13
<211> LENGTH: 9
<212> TYPE: PRT
<213> ORGANISM: Homo sapiens

<400> SEQUENCE: 13

Met Gln Gly Ser His Trp Pro Phe Thr
 1               5

<210> SEQ ID NO 14
```

<211> LENGTH: 5
<212> TYPE: PRT
<213> ORGANISM: Homo sapiens

<400> SEQUENCE: 14

Lys Tyr His Met Val
1               5

<210> SEQ ID NO 15
<211> LENGTH: 17
<212> TYPE: PRT
<213> ORGANISM: Homo sapiens

<400> SEQUENCE: 15

Ser Ile Gly Pro Ser Gly Gly Asn Thr Tyr Tyr Ala Asp Ser Val Lys
1               5                   10                  15

Gly

<210> SEQ ID NO 16
<211> LENGTH: 8
<212> TYPE: PRT
<213> ORGANISM: Homo sapiens

<400> SEQUENCE: 16

Ala Leu Gly Ala Thr Phe Asp Tyr
1               5

<210> SEQ ID NO 17
<211> LENGTH: 22
<212> TYPE: PRT
<213> ORGANISM: Homo sapiens

<400> SEQUENCE: 17

Ala Asp Trp Pro Gly Pro Pro Glu Leu Asp Val Cys Val Glu Glu Ala
1               5                   10                  15

Glu Gly Glu Ala Pro Trp
            20

<210> SEQ ID NO 18
<211> LENGTH: 21
<212> TYPE: PRT
<213> ORGANISM: Homo sapiens

<400> SEQUENCE: 18

Asp Trp Pro Gly Pro Pro Glu Leu Asp Val Cys Val Glu Glu Ala Glu
1               5                   10                  15

Gly Glu Ala Pro Trp
            20

<210> SEQ ID NO 19
<211> LENGTH: 20
<212> TYPE: PRT
<213> ORGANISM: Homo sapiens

<400> SEQUENCE: 19

Trp Pro Gly Pro Pro Glu Leu Asp Val Cys Val Glu Glu Ala Glu Gly
1               5                   10                  15

Glu Ala Pro Trp
            20

<210> SEQ ID NO 20
<211> LENGTH: 19
<212> TYPE: PRT

```
<400> SEQUENCE: 20

Pro Gly Pro Pro Glu Leu Asp Val Cys Val Glu Glu Ala Glu Gly Glu
1               5                   10                  15

Ala Pro Trp

<210> SEQ ID NO 21
<211> LENGTH: 18
<212> TYPE: PRT
<213> ORGANISM: Homo sapiens

<400> SEQUENCE: 21

Gly Pro Pro Glu Leu Asp Val Cys Val Glu Glu Ala Glu Gly Glu Ala
1               5                   10                  15

Pro Trp

<210> SEQ ID NO 22
<211> LENGTH: 17
<212> TYPE: PRT
<213> ORGANISM: Homo sapiens

<400> SEQUENCE: 22

Pro Pro Glu Leu Asp Val Cys Val Glu Glu Ala Glu Gly Glu Ala Pro
1               5                   10                  15

Trp

<210> SEQ ID NO 23
<211> LENGTH: 16
<212> TYPE: PRT
<213> ORGANISM: Homo sapiens

<400> SEQUENCE: 23

Pro Glu Leu Asp Val Cys Val Glu Glu Ala Glu Gly Glu Ala Pro Trp
1               5                   10                  15

<210> SEQ ID NO 24
<211> LENGTH: 22
<212> TYPE: PRT
<213> ORGANISM: Homo sapiens

<400> SEQUENCE: 24

Arg Ala Asp Trp Pro Gly Pro Pro Glu Leu Asp Val Cys Val Glu Glu
1               5                   10                  15

Ala Glu Gly Glu Ala Pro
            20

<210> SEQ ID NO 25
<211> LENGTH: 21
<212> TYPE: PRT
<213> ORGANISM: Homo sapiens

<400> SEQUENCE: 25

Arg Ala Asp Trp Pro Gly Pro Pro Glu Leu Asp Val Cys Val Glu Glu
1               5                   10                  15

Ala Glu Gly Glu Ala
            20

<210> SEQ ID NO 26
<211> LENGTH: 20
<212> TYPE: PRT
<213> ORGANISM: Homo sapiens

<400> SEQUENCE: 26
```

```
Arg Ala Asp Trp Pro Gly Pro Pro Glu Leu Asp Val Cys Val Glu Glu
1               5                   10                  15

Ala Glu Gly Glu
            20

<210> SEQ ID NO 27
<211> LENGTH: 19
<212> TYPE: PRT
<213> ORGANISM: Homo sapiens

<400> SEQUENCE: 27

Arg Ala Asp Trp Pro Gly Pro Pro Glu Leu Asp Val Cys Val Glu Glu
1               5                   10                  15

Ala Glu Gly

<210> SEQ ID NO 28
<211> LENGTH: 18
<212> TYPE: PRT
<213> ORGANISM: Homo sapiens

<400> SEQUENCE: 28

Arg Ala Asp Trp Pro Gly Pro Pro Glu Leu Asp Val Cys Val Glu Glu
1               5                   10                  15

Ala Glu

<210> SEQ ID NO 29
<211> LENGTH: 17
<212> TYPE: PRT
<213> ORGANISM: Homo sapiens

<400> SEQUENCE: 29

Arg Ala Asp Trp Pro Gly Pro Pro Glu Leu Asp Val Cys Val Glu Glu
1               5                   10                  15

Ala

<210> SEQ ID NO 30
<211> LENGTH: 16
<212> TYPE: PRT
<213> ORGANISM: Homo sapiens

<400> SEQUENCE: 30

Arg Ala Asp Trp Pro Gly Pro Pro Glu Leu Asp Val Cys Val Glu Glu
1               5                   10                  15

<210> SEQ ID NO 31
<211> LENGTH: 15
<212> TYPE: PRT
<213> ORGANISM: Homo sapiens

<400> SEQUENCE: 31

Arg Ala Asp Trp Pro Gly Pro Pro Glu Leu Asp Val Cys Val Glu
1               5                   10                  15

<210> SEQ ID NO 32
<211> LENGTH: 14
<212> TYPE: PRT
<213> ORGANISM: Homo sapiens

<400> SEQUENCE: 32

Arg Ala Asp Trp Pro Gly Pro Pro Glu Leu Asp Val Cys Val
1               5                   10
```

```
<210> SEQ ID NO 33
<211> LENGTH: 13
<212> TYPE: PRT
<213> ORGANISM: Homo sapiens

<400> SEQUENCE: 33

Arg Ala Asp Trp Pro Gly Pro Pro Glu Leu Asp Val Cys
1               5                   10

<210> SEQ ID NO 34
<211> LENGTH: 12
<212> TYPE: PRT
<213> ORGANISM: Homo sapiens

<400> SEQUENCE: 34

Arg Ala Asp Trp Pro Gly Pro Pro Glu Leu Asp Val
1               5                   10

<210> SEQ ID NO 35
<211> LENGTH: 11
<212> TYPE: PRT
<213> ORGANISM: Homo sapiens

<400> SEQUENCE: 35

Arg Ala Asp Trp Pro Gly Pro Pro Glu Leu Asp
1               5                   10

<210> SEQ ID NO 36
<211> LENGTH: 10
<212> TYPE: PRT
<213> ORGANISM: Homo sapiens

<400> SEQUENCE: 36

Arg Ala Asp Trp Pro Gly Pro Pro Glu Leu
1               5                   10

<210> SEQ ID NO 37
<211> LENGTH: 9
<212> TYPE: PRT
<213> ORGANISM: Homo sapiens

<400> SEQUENCE: 37

Arg Ala Asp Trp Pro Gly Pro Pro Glu
1               5

<210> SEQ ID NO 38
<211> LENGTH: 21
<212> TYPE: PRT
<213> ORGANISM: Homo sapiens

<400> SEQUENCE: 38

Ala Asp Trp Pro Gly Pro Pro Glu Leu Asp Val Cys Val Glu Glu Ala
1               5                   10                  15

Glu Gly Glu Ala Pro
            20

<210> SEQ ID NO 39
<211> LENGTH: 19
<212> TYPE: PRT
<213> ORGANISM: Homo sapiens

<400> SEQUENCE: 39

Asp Trp Pro Gly Pro Pro Glu Leu Asp Val Cys Val Glu Glu Ala Glu
1               5                   10                  15

Gly Glu Ala
```

<210> SEQ ID NO 40
<211> LENGTH: 6
<212> TYPE: PRT
<213> ORGANISM: Homo sapiens

<400> SEQUENCE: 40

Gly Pro Pro Glu Leu Asp
1               5

<210> SEQ ID NO 41
<211> LENGTH: 8
<212> TYPE: PRT
<213> ORGANISM: Homo sapiens

<400> SEQUENCE: 41

Pro Gly Pro Pro Glu Leu Asp Val
1               5

<210> SEQ ID NO 42
<211> LENGTH: 7
<212> TYPE: PRT
<213> ORGANISM: Homo sapiens

<400> SEQUENCE: 42

Pro Gly Pro Pro Glu Leu Asp
1               5

<210> SEQ ID NO 43
<211> LENGTH: 7
<212> TYPE: PRT
<213> ORGANISM: Homo sapiens

<400> SEQUENCE: 43

Gly Pro Pro Glu Leu Asp Val
1               5

<210> SEQ ID NO 44
<211> LENGTH: 10
<212> TYPE: PRT
<213> ORGANISM: Homo sapiens

<400> SEQUENCE: 44

Trp Pro Gly Pro Pro Glu Leu Asp Val Cys
1               5                   10

<210> SEQ ID NO 45
<211> LENGTH: 9
<212> TYPE: PRT
<213> ORGANISM: Homo sapiens

<400> SEQUENCE: 45

Pro Gly Pro Pro Glu Leu Asp Val Cys
1               5

<210> SEQ ID NO 46
<211> LENGTH: 9
<212> TYPE: PRT
<213> ORGANISM: Homo sapiens

<400> SEQUENCE: 46

Trp Pro Gly Pro Pro Glu Leu Asp Val
1               5

<210> SEQ ID NO 47

-continued

```
<211> LENGTH: 27
<212> TYPE: PRT
<213> ORGANISM: Homo sapiens

<400> SEQUENCE: 47

Tyr Leu Ala Met Thr Pro Leu Ile Pro Gln Ser Lys Asp Glu Asn Ser
1               5                   10                  15

Asp Asp Tyr Thr Thr Phe Asp Asp Val Gly Ser
            20                  25

<210> SEQ ID NO 48
<211> LENGTH: 18
<212> TYPE: PRT
<213> ORGANISM: Homo sapiens

<400> SEQUENCE: 48

Glu Leu Gln Leu Glu Glu Ser Cys Ala Glu Ala Gln Asp Gly Glu Leu
1               5                   10                  15

Asp Gly

<210> SEQ ID NO 49
<211> LENGTH: 26
<212> TYPE: PRT
<213> ORGANISM: Homo sapiens

<400> SEQUENCE: 49

Asp Trp Gln Met Pro Pro Pro Tyr Val Val Leu Asp Leu Pro Gln Glu
1               5                   10                  15

Thr Leu Glu Glu Glu Thr Pro Gly Ala Asn
            20                  25

<210> SEQ ID NO 50
<211> LENGTH: 330
<212> TYPE: DNA
<213> ORGANISM: Homo sapiens

<400> SEQUENCE: 50
gcacaagaca tccagatgac ccagtctcct tccaccctgt ctgcatctat aggagacaga     60
gtcaccatca cttgccgggc cagtcagagt attaatagtt ggttggcctg gtatcagcag    120
aaaccaggga aaggccctga cctcctgatc tataaggcgt ctagtttaca aagtggggtc    180
ccatcaaggt tcagcggcag tggatctggg acagaattca ctctcaccat cagcagcctg    240
cagcctgatg attttgcaac ttattactgc caacagtata gtagttggcc cctcactttc    300
ggcggaggga ccaaggtgga gatcaaacga                                     330

<210> SEQ ID NO 51
<211> LENGTH: 363
<212> TYPE: DNA
<213> ORGANISM: Homo sapiens

<400> SEQUENCE: 51
gaagttcaat tgttagagtc tggtggcggt cttgttcagc ctggtggttc tttacgtctt     60
tcttgcgctg cttccggatt cactttctct ttttactcta tgctttgggt tcgccaagct    120
cctggtaaag gtttggagtg gtttcttat atcggtcctt ctggtggcaa gacttattat    180
gctgactccg ttaaaggtcg cttcactatc tctagagaca actctaagaa tactctctac    240
ttgcagatga acagcttaag ggctgaggac accgccatgt attactgtgc gagacgctat    300
tgtagtggtg gtagctgcta ctttgactac tggggccagg gcaccctggt caccgtctca    360
agc                                                                  363
```

<210> SEQ ID NO 52
<211> LENGTH: 110
<212> TYPE: PRT
<213> ORGANISM: Homo sapiens

<400> SEQUENCE: 52

Ala Gln Asp Ile Gln Met Thr Gln Ser Pro Ser Thr Leu Ser Ala Ser
1               5                   10                  15

Ile Gly Asp Arg Val Thr Ile Thr Cys Arg Ala Ser Gln Ser Ile Asn
            20                  25                  30

Ser Trp Leu Ala Trp Tyr Gln Gln Lys Pro Gly Lys Gly Pro Asp Leu
        35                  40                  45

Leu Ile Tyr Lys Ala Ser Ser Leu Gln Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Tyr Ser Ser Trp
                85                  90                  95

Pro Leu Thr Phe Gly Gly Gly Thr Lys Val Glu Ile Lys Arg
            100                 105                 110

<210> SEQ ID NO 53
<211> LENGTH: 121
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Ser Met Leu Trp Val Arg Gln Ala Pro Gly Lys Gly Leu Glu Trp Val
        35                  40                  45

Ser Tyr Ile Gly Pro Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Arg Tyr Cys Ser Gly Ser Cys Tyr Phe Asp Tyr Trp Gly
            100                 105                 110

Gln Gly Thr Leu Val Thr Val Ser Ser
        115                 120

<210> SEQ ID NO 54
<211> LENGTH: 11
<212> TYPE: PRT
<213> ORGANISM: Homo sapiens

<400> SEQUENCE: 54

Arg Ala Ser Gln Ser Ile Asn Ser Trp Leu Ala
1               5                   10

<210> SEQ ID NO 55
<211> LENGTH: 7
<212> TYPE: PRT
<213> ORGANISM: Homo sapiens

<400> SEQUENCE: 55

Lys Ala Ser Ser Leu Gln Ser
1               5

<210> SEQ ID NO 56
<211> LENGTH: 9
<212> TYPE: PRT
<213> ORGANISM: Homo sapiens

<400> SEQUENCE: 56

Gln Gln Tyr Ser Ser Trp Pro Leu Thr
1               5

<210> SEQ ID NO 57
<211> LENGTH: 5
<212> TYPE: PRT
<213> ORGANISM: Homo sapiens

<400> SEQUENCE: 57

Phe Tyr Ser Met Leu
1               5

<210> SEQ ID NO 58
<211> LENGTH: 17
<212> TYPE: PRT
<213> ORGANISM: Homo sapiens

<400> SEQUENCE: 58

Tyr Ile Gly Pro Ser Gly Gly Lys Thr Tyr Tyr Ala Asp Ser Val Lys
1               5                   10                  15

Gly

<210> SEQ ID NO 59
<211> LENGTH: 12
<212> TYPE: PRT
<213> ORGANISM: Homo sapiens

<400> SEQUENCE: 59

Arg Tyr Cys Ser Gly Gly Ser Cys Tyr Phe Asp Tyr
1               5                   10

<210> SEQ ID NO 60
<211> LENGTH: 345
<212> TYPE: DNA
<213> ORGANISM: Homo sapiens

<400> SEQUENCE: 60
gcacaagaca tccagatgac ccagtctcca gtctccctgc ccgtcactct tggacagccg     60
gcctccatct cctgcaggtc tagtcacagc ctcgtataca gtcatggggg cacctacttg    120
aattggtttc agcagaggcc aggccgatct ccaaggcgcc tgatttatca ggtttccaac    180
cgggactctg ggtcccaga cagattcagc ggcagtgggt cagacactga tttcacactg     240
caaatcagca gggtggaggc tgacgatatt gggatttatt actgcatgca atctacatat    300
tggccttacg cttttggcca ggggaccaag ctcgacatca aacga                   345

<210> SEQ ID NO 61
<211> LENGTH: 345
<212> TYPE: DNA
<213> ORGANISM: Homo sapiens

<400> SEQUENCE: 61
gaagttcaat tgttagagtc tggtggcggt cttgttcagc ctggtggttc tttacgtctt     60

```
tcttgcgctg cttccggatt cactttctct aagtacggta tgacttgggt tcgccaagct    120
cctggtaaag gtttggagtg ggtttcttct atctattctt ctggtggccc tactgagtat    180
gctgactccg ttaaaggtcg cttcactatc tctagagaca actctaagaa tactctctac    240
ttgcagatga acagcttaag ggctgaggac acggccgtgt attactgtgc gagaggtggg    300
ggtatggacg tctggggcca aggcaccctg gtcaccgtct caagc                     345
```

```
<210> SEQ ID NO 62
<211> LENGTH: 115
<212> TYPE: PRT
<213> ORGANISM: Homo sapiens

<400> SEQUENCE: 62
```

| Ala | Gln | Asp | Ile | Gln | Met | Thr | Gln | Ser | Pro | Val | Ser | Leu | Pro | Val | Thr |
|---|---|---|---|---|---|---|---|---|---|---|---|---|---|---|---|
| 1 | | | | 5 | | | | | 10 | | | | | 15 | |

Leu Gly Gln Pro Ala Ser Ile Ser Cys Arg Ser Ser His Ser Leu Val
            20                  25                  30

Tyr Ser His Gly Gly Thr Tyr Leu Asn Trp Phe Gln Arg Pro Gly
        35                  40                  45

Arg Ser Pro Arg Arg Leu Ile Tyr Gln Val Ser Asn Arg Asp Ser Gly
50                  55                  60

Val Pro Asp Arg Phe Ser Gly Ser Gly Ser Asp Thr Asp Phe Thr Leu
65                  70                  75                  80

Gln Ile Ser Arg Val Glu Ala Asp Asp Ile Gly Ile Tyr Tyr Cys Met
                85                  90                  95

Gln Ser Thr Tyr Trp Pro Tyr Ala Phe Gly Gln Gly Thr Lys Leu Asp
            100                 105                 110

Ile Lys Arg
        115

<210> SEQ ID NO 63
<211> LENGTH: 115
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Gly Met Thr Trp Val Arg Gln Ala Pro Gly Lys Gly Leu Glu Trp Val
        35                  40                  45

Ser Ser Ile Tyr Ser Ser Gly Gly Pro Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Met Asp Val Trp Gly Gln Gly Thr Leu Val Thr
            100                 105                 110

Val Ser Ser
        115

<210> SEQ ID NO 64
<211> LENGTH: 16
<212> TYPE: PRT
<213> ORGANISM: Homo sapiens

<400> SEQUENCE: 64

Arg Ser Ser His Ser Leu Val Tyr Ser His Gly Gly Thr Tyr Leu Asn
1               5                   10                  15

<210> SEQ ID NO 65
<211> LENGTH: 7
<212> TYPE: PRT
<213> ORGANISM: Homo sapiens

<400> SEQUENCE: 65

Gln Val Ser Asn Arg Asp Ser
1               5

<210> SEQ ID NO 66
<211> LENGTH: 9
<212> TYPE: PRT
<213> ORGANISM: Homo sapiens

<400> SEQUENCE: 66

Met Gln Ser Thr Tyr Trp Pro Tyr Ala
1               5

<210> SEQ ID NO 67
<211> LENGTH: 5
<212> TYPE: PRT
<213> ORGANISM: Homo sapiens

<400> SEQUENCE: 67

Lys Tyr Gly Met Thr
1               5

<210> SEQ ID NO 68
<211> LENGTH: 17
<212> TYPE: PRT
<213> ORGANISM: Homo sapiens

<400> SEQUENCE: 68

Ser Ile Tyr Ser Ser Gly Gly Pro Thr Glu Tyr Ala Asp Ser Val Lys
1               5                   10                  15

Gly

<210> SEQ ID NO 69
<211> LENGTH: 6
<212> TYPE: PRT
<213> ORGANISM: Homo sapiens

<400> SEQUENCE: 69

Gly Gly Gly Met Asp Val
1               5

<210> SEQ ID NO 70
<211> LENGTH: 330
<212> TYPE: DNA
<213> ORGANISM: Homo sapiens

<400> SEQUENCE: 70
gcacaagaca tccagatgac ccagtctcca tcctccctgt ctgcatctat aggcgacaga     60
gtcaccatca cttgccgcgg aagtcagaat attggtagat atttaaattg gtatcaacac    120
aaacctggga agcccctga tctcctcgtc tatgctgcct ccagtttgcg aagtggggtc    180
ccatcaagat tcagtggcag tggatctggg agagatttca ctctcaccat cagcagtctt    240
caacctggag attttgcaac ttactactgt cagcagagtt acagtgcccc gttcactttc    300

```
ggcgccggga ccaaggtgga tgtcaaacga                                     330
```

<210> SEQ ID NO 71
<211> LENGTH: 351
<212> TYPE: DNA
<213> ORGANISM: Homo sapiens

<400> SEQUENCE: 71

```
gaagttcaat tgttagagtc tggtggcggt cttgttcagc ctggtggttc tttacgtctt      60
tcttgcgctg cttccggatt cactttctct aattacggta tgttttgggt tcgccaagct     120
cctggtaaag gtttggagtg gtttcttct atctggcctt ctggtggcaa tactatgtat      180
gctgactccg ttaaaggtcg cttcactatc tctagagaca actctaagaa tactctctac     240
ttgcagatga acagcttaag ggctgaggac acggccgtgt attactgtgc gagagcttct     300
tactacggta tggacgtctg gggccaaggg accacggtca ccgtctcaag c              351
```

<210> SEQ ID NO 72
<211> LENGTH: 110
<212> TYPE: PRT
<213> ORGANISM: Homo sapiens

<400> SEQUENCE: 72

Ala Gln Asp Ile Gln Met Thr Gln Ser Pro Ser Ser Leu Ser Ala Ser
1               5                   10                  15
Ile Gly Asp Arg Val Thr Ile Thr Cys Arg Gly Ser Gln Asn Ile Gly
            20                  25                  30
Arg Tyr Leu Asn Trp Tyr Gln His Lys Pro Gly Lys Ala Pro Asp Leu
        35                  40                  45
Leu Val Tyr Ala Ala Ser Ser Leu Arg Ser Gly Val Pro Ser Arg Phe
    50                  55                  60
Ser Gly Ser Gly Ser Gly Arg Asp Phe Thr Leu Thr Ile Ser Ser Leu
65                  70                  75                  80
Gln Pro Gly Asp Phe Ala Thr Tyr Tyr Cys Gln Gln Ser Tyr Ser Ala
                85                  90                  95
Pro Phe Thr Phe Gly Ala Gly Thr Lys Val Asp Val Lys Arg
            100                 105                 110

<210> SEQ ID NO 73
<211> LENGTH: 117
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Phe Trp Val Arg Gln Ala Pro Gly Lys Gly Leu Glu Trp Val
        35                  40                  45
Ser Ser Ile Trp Pro Ser Gly Gly Asn Thr Met Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Ser Tyr Tyr Gly Met Asp Val Trp Gly Gln Gly Thr Thr
            100                 105                 110

Val Thr Val Ser Ser
        115

<210> SEQ ID NO 74
<211> LENGTH: 11
<212> TYPE: PRT
<213> ORGANISM: Homo sapiens

<400> SEQUENCE: 74

Arg Gly Ser Gln Asn Ile Gly Arg Tyr Leu Asn
1               5                   10

<210> SEQ ID NO 75
<211> LENGTH: 7
<212> TYPE: PRT
<213> ORGANISM: Homo sapiens

<400> SEQUENCE: 75

Ala Ala Ser Ser Leu Arg Ser
1               5

<210> SEQ ID NO 76
<211> LENGTH: 9
<212> TYPE: PRT
<213> ORGANISM: Homo sapiens

<400> SEQUENCE: 76

Gln Gln Ser Tyr Ser Ala Pro Phe Thr
1               5

<210> SEQ ID NO 77
<211> LENGTH: 5
<212> TYPE: PRT
<213> ORGANISM: Homo sapiens

<400> SEQUENCE: 77

Asn Tyr Gly Met Phe
1               5

<210> SEQ ID NO 78
<211> LENGTH: 17
<212> TYPE: PRT
<213> ORGANISM: Homo sapiens

<400> SEQUENCE: 78

Ser Ile Trp Pro Ser Gly Gly Asn Thr Met Tyr Ala Asp Ser Val Lys
1               5                   10                  15

Gly

<210> SEQ ID NO 79
<211> LENGTH: 8
<212> TYPE: PRT
<213> ORGANISM: Homo sapiens

<400> SEQUENCE: 79

Ala Ser Tyr Tyr Gly Met Asp Val
1               5

<210> SEQ ID NO 80
<211> LENGTH: 375
<212> TYPE: DNA
<213> ORGANISM: Homo sapiens

<400> SEQUENCE: 80
gaagttcaat tgttagagtc tggtggcggt cttgttcagc ctggtggttc tttacgtctt      60

```
tcttgcgctg cttccggatt cactttctct acttacgcta tgcgttgggt tcgccaagct      120
cctggtaaag gtttggagtg ggtttctggt atcggtcctt ctggtggcaa gacttcttat      180
gctgactccg ttaaaggtcg cttcactatc tctagagaca actctaagaa tactctctac      240
ttgcagatga acagcttaag ggctgaggac acggccgtgt attactgtgc gagagcgtct      300
ggtatagtgg gagcttattc gtacggtatg gacgtctggg gccaagggac cacggtcacc      360
gtctcaagcg cctcc                                                       375
```

<210> SEQ ID NO 81
<211> LENGTH: 125
<212> TYPE: PRT
<213> ORGANISM: Homo sapiens

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Arg Trp Val Arg Gln Ala Pro Gly Lys Gly Leu Glu Trp Val
        35                  40                  45

Ser Gly Ile Gly Pro Ser Gly Gly Lys Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Gly Ile Val Gly Ala Tyr Ser Tyr Gly Met Asp Val
            100                 105                 110

Trp Gly Gln Gly Thr Thr Val Thr Val Ser Ser Ala Ser
        115                 120                 125
```

<210> SEQ ID NO 82
<211> LENGTH: 5
<212> TYPE: PRT
<213> ORGANISM: Homo sapiens

<400> SEQUENCE: 82

```
Thr Tyr Ala Met Arg
1               5
```

<210> SEQ ID NO 83
<211> LENGTH: 17
<212> TYPE: PRT
<213> ORGANISM: Homo sapiens

<400> SEQUENCE: 83

```
Gly Ile Gly Pro Ser Gly Gly Lys Thr Ser Tyr Ala Asp Ser Val Lys
1               5                   10                  15

Gly
```

<210> SEQ ID NO 84
<211> LENGTH: 14
<212> TYPE: PRT
<213> ORGANISM: Homo sapiens

<400> SEQUENCE: 84

```
Ala Ser Gly Ile Val Gly Ala Tyr Ser Tyr Gly Met Asp Val
1               5                   10
```

```
<210> SEQ ID NO 85
<211> LENGTH: 15
<212> TYPE: PRT
<213> ORGANISM: Artificial
<220> FEATURE:
<223> OTHER INFORMATION: synthetic randomized migis peptide

<400> SEQUENCE: 85

Gly Glu Asp Trp Cys Glu Val Ala Leu Glu Pro Ala Glu Val Glu
1               5                   10                  15

<210> SEQ ID NO 86
<211> LENGTH: 25
<212> TYPE: PRT
<213> ORGANISM: Homo sapiens

<400> SEQUENCE: 86

Lys Ser Leu Ser Leu Ser Pro Glu Leu Gln Leu Glu Glu Ser Cys Ala
1               5                   10                  15

Glu Ala Gln Asp Gly Glu Leu Asp Gly
            20                  25

<210> SEQ ID NO 87
<211> LENGTH: 21
<212> TYPE: PRT
<213> ORGANISM: Homo sapiens

<400> SEQUENCE: 87

Glu Arg Thr Val Asp Lys Ser Thr Glu Gly Glu Val Ser Ala Asp Glu
1               5                   10                  15

Glu Gly Phe Glu Asn
            20
```